United States Patent
Lohse et al.

(10) Patent No.: US 10,180,426 B2
(45) Date of Patent: Jan. 15, 2019

(54) QUANTIFICATION OF SINGLE TARGET MOLECULES IN HISTOLOGICAL SAMPLES

(75) Inventors: Jesper Lohse, Herlev (DK); Galina Skladtchikova, Hellerup (DK)

(73) Assignee: DAKO DENMARK A/S, Glostrup (DK)

( * ) Notice: Subject to any disclaimer, the term of this patent is extended or adjusted under 35 U.S.C. 154(b) by 797 days.

(21) Appl. No.: 13/884,080

(22) PCT Filed: Nov. 8, 2011

(86) PCT No.: PCT/DK2011/000131
§ 371 (c)(1),
(2), (4) Date: Oct. 22, 2013

(87) PCT Pub. No.: WO2012/062318
PCT Pub. Date: May 18, 2012

(65) Prior Publication Data
US 2014/0038169 A1    Feb. 6, 2014

Related U.S. Application Data

(60) Provisional application No. 61/411,050, filed on Nov. 8, 2010.

(51) Int. Cl.
| | | |
|---|---|---|
| G01N 33/543 | (2006.01) | |
| G01N 33/58 | (2006.01) | |
| G01N 33/50 | (2006.01) | |
| G01N 33/532 | (2006.01) | |
| G01N 33/68 | (2006.01) | |

(52) U.S. Cl.
CPC ....... *G01N 33/543* (2013.01); *G01N 33/5088* (2013.01); *G01N 33/532* (2013.01); *G01N 33/58* (2013.01); *G01N 33/6893* (2013.01); *G01N 2800/50* (2013.01)

(58) Field of Classification Search
None
See application file for complete search history.

(56) References Cited

U.S. PATENT DOCUMENTS

| | | | | |
|---|---|---|---|---|
| 4,743,542 A | * | 5/1988 | Graham, Jr. ...... | G01N 33/54393 435/7.94 |
| 5,585,089 A | | 12/1996 | Queen et al. | |
| 8,435,735 B2 | * | 5/2013 | Lohse ................ | C08G 63/672 435/6.1 |
| 8,999,639 B2 | * | 4/2015 | Lohse ................ | C08G 63/672 435/6.1 |
| 9,091,691 B2 | * | 7/2015 | Lohse ................ | G01N 33/581 |
| 2008/0305497 A1 | | 12/2008 | Kosmeder et al. | |
| 2009/0053743 A1 | * | 2/2009 | Link ................ | G01N 33/54306 435/7.93 |
| 2014/0315218 A1 | * | 10/2014 | Lohse ................ | G01N 33/6854 435/7.9 |
| 2016/0370375 A1 | * | 12/2016 | Lohse ................ | C12Q 1/28 |

FOREIGN PATENT DOCUMENTS

| | | |
|---|---|---|
| CA | 2816472 | 5/2012 |
| CN | 102713626 | 10/2012 |
| CN | 103201627 | 7/2013 |
| EP | 0368684 A1 | 5/1990 |
| EP | 0589877 | 11/1996 |
| EP | 0436597 B1 | 4/1997 |
| EP | 0623679 | 6/2003 |
| EP | 2638392 B1 | 1/2016 |
| WO | WO 02/088376 | 11/2002 |
| WO | WO 2006/116628 | 11/2006 |
| WO | 2007015168 A2 | 2/2007 |
| WO | WO 2009/036760 | 3/2009 |
| WO | 2010094283 A1 | 8/2010 |
| WO | WO 2010/094284 * | 8/2010 |
| WO | 2011047680 A1 | 4/2011 |

OTHER PUBLICATIONS

Molecular Probes, Section 6.2, 2002, pp. 152-159.*
Lohse et al., "Improved Catalyzed Reporter Deposition, iCARD," Bioconjugate Chem., 2014, vol. 25, No. 6, pp. 1036-1042.*
Jensen et al., "A novel quantitative immunohistochemistry method for precise protein measurements directly in formalin-fixed, paraffin-embedded specimens: analytical performance measuring HER2," Modern Pathology, 2017, vol. 30, pp. 180-193; Published online Oct. 21, 2016.*
International Search Report of International Application No. PCT/DK2011/000131, dated Feb. 9, 2012.
Altschul, S et al., "Gapped BLAST and PSI-BLAST: A New Generation of Protein Database Search Programs", *Nucleic Acids Res.*, vol. 25, No. 17 1997, 3389-3402.
Good, N et al., "Hydrogen Ion Buffers for Biological Research", *Biochemistry*, vol. 5, No. 2 1966, 467-477.
Harlow, et al., "Antibodies: a Laboratory Manual", Cold Spring Harbor Press, Cold Spring Harbor, NY 1988.
Hicks, David G et al., "Routine Use of Controls for IHC Testing Laboratory Medicine", Assessment of HER2 Status by Immunohistochemisty, 42(8) 2011, 459-467.
Jones, R et al., "Cancer Risk Assessments in Light of Chernobyl", *Nature*, vol. 323 1986, 585-586.
Kang, S et al., "Linkage of recognition and replication functions by assembling combinatorial antibody Fab libraries along phage surfaces", *Proc. Nat/. Acad. Sci. USA*, vol. 88 May 1991, 4363-4366.
Marks, J et al., "By-Passing Immunization: Building High Affinity Human Antibodies by Chain Shuffling", *Bio/Technol.* vol. 10 Jul. 1992, 779-783.

(Continued)

*Primary Examiner* — Galina Yakovleva

(57) ABSTRACT

The present invention lies in the field of visualization and quantification of immobilized targets in samples using immunochemical means. The methods of the invention utilize an immunostaining system allowing visualizing single target units in samples as distinct dots. In particular, the invention relates to methods and reagents for visualization and quantification of molecular targets immunostained in histological samples and use of said method and reagents in medical diagnostic. However, the visualization and quantification methods of the invention are applicable to a variety of targets in different samples and allow precise quantifying both relative and absolute amounts thereof.

31 Claims, 7 Drawing Sheets

(56) References Cited

OTHER PUBLICATIONS

McCafferty, J et al., "Phage Antibodies: Filamentous Phage Displaying Antibody Variable Domains", *Nature*, vol. 348 1990, 552-554.
Nielson, et al., "Methods of making PNAs are known in the art", Current Opinion in Biotechnology 12:16 2001.
Phillips, Le et al., "Benzidine as a Substrate for Measuring Phenoloxidase Activity in Crude Cell-Free", Mycologia, 68 1976, 277-285.
Plou, FJ et al., "Laccases and their applications: a patent review", Recent Pat Biotechnol, 2(1) 2008, 10-24.
Rodriguez Couto, S et al., "Industrial and biotechnological applications of laccase:a review Biotechnol", 2006, 500-13.
Sorenson, et al., the binding agent may comprise a locked nucleic acid (LNA), Chem. Commun. 7(17) 2003, 2130.
Waterhouse, P et al., "Combinatorial Infection and In Vivo Recombination: A Strategy for Making Large Phage Antibody Repertoires", *Nucleic Acids Reas.*, vol. 21, No. 9 1993, 2265-2266.
Ausubel, et al., "Current Protocols in Molecular Biology," John Wiley & Sons, 2003, Table of Contents, 25 pages.
Sambrook, et al., "Molecular Cloning", 3rd Ed., Cold Spring Harbor Press, 2001, Table of Contents, 20 pages.

\* cited by examiner

QUANTIFICATION OF SINGLE TARGET MOLECULES IN HISTOLOGICAL SAMPLES

FIELD OF THE INVENTION

The present invention lies in the field of visualization and quantification of immobilized targets in samples using immunochemical means. In particular, the invention relates to methods and reagents for quantification of molecular targets in immunostained histological samples and use of said method and reagents in medical diagnostic.

BACKGROUND OF THE INVENTION

In the field of immunohistochemistry, IHC, biological targets of interest are typically stained with enzymatically generated dyes. However, most of today's IHC enzymatic systems have a limited usability of for target visualization due to restricted sensitivity: if a target is of very low abundance, the amount of deposited dye remains undetectable. Likewise, there is an upper detection limit above which a further dye deposition does not lead to detectably more intense stains. Using lower concentration of reagents, the upper detection limit may be compromised to allow differentiation between high and very high abundance targets; however this also leads to an increase of the lower detection limit, i.e. the loss in sensitivity of detection. Thus, most of the today's systems have a limited dynamic range of detection. Further, differences in sensitivity between different visualization systems from same or different vendors makes comparison the staining results difficult.

A further challenge is quantification of immunochemically stained targets due to the dye deposition is not a linear function of target concentration. Around the baseline of detection limit the intensity increases rapidly as a direct function of target concentration (as the going from no detectable signal to a signal, even of a low strength, represents an infinite increase. Conversely, close to the upper detection limit, even a large increase in target concentration will lead to virtually no perceptible increase in the already intense signal.

A further complication arises from the fact that no internationally recognized standards exist, and invariable reference samples are difficult to prepare. Even serial sections of the same tissue sample usually exhibit biological variation. Immortal cell lines might in principle provide the infinite reference material, however differences in cultivation conditions, cell cycle circles and biological variation will also in this case lead to some batch to batch variation in target expression. Glass slides chemically modified with peptides or proteins may be used as surrogate targets, however comparison to tissue samples is not straight forwards.

Thus there is a need for standardized quantitative detection of immobilized targets in biological samples.

Recently described method of immunochemical staining of single units of immobilized targets in biological samples, including histological samples, (PCT/DK2010/000137) provides a visualization system characterized by an extreme sensitivity (i.e. a single molecules can be visualized and detected) and a linear correlation between the amount of deposited dye and target expression within the whole dynamic range of target expression.

The present invention utilizes visualization potential of the system of PCT/DK2010/000137, and provides methods for a precise quantification of immobilized targets in samples, in particular biological samples, including evaluation of the absolute number of molecules of a particular target.

SUMMARY OF THE INVENTION

The present invention relates to methods for quantification of a target, e.g. a molecular target, in samples wherein the target is immobilized, e.g. histological samples, reagents to perform the methods, assays that utilize the method and reagents and application of the methods and assays in medical diagnostics and therapy.

One aspect of the present invention relates to a method for quantifying a target present in a sample, wherein said target is immobilized, comprising
(a) incubating a sample comprising a population of individual units of a target with one or more binding agents, wherein
(i) at least one of the binding agent is capable of specifically binding to a single individual unit of the target, and
(ii) at least one of the binding agents comprises an enzyme, and
(iii) the binding affinity of at least one of the binding agents of (i) or (ii) to its binding partner in the sample is known,
and thereby forming one or more discrete single target sites with a fractional sub-population of individual single units of the target, wherein each discrete single target site comprises a complex comprising a complex of one individual unit of said fractional sub-population of individual single units and one or more binding agent, wherein at least one binding agent comprises the enzyme;
(b) visualizing the discrete single target sites comprising the enzyme as visually distinct dots;
(c) quantifying the visually distinct dots,
evaluating the amount of the target in the sample.

In different embodiments the target sites may be formed with majority or minority of single individual units of the target present in the sample.

Another aspect of the present invention relates to a method for quantifying a target present in a sample, wherein said target is immobilized, comprising
(a) incubating a sample comprising a population of individual units of the target with one or more binding agents,
wherein
(i) at least one of the binding agent is capable of specifically binding to a single individual unit of the target, and
(ii) at least one of the binding agents comprises an enzyme,
and thereby forming one or more discrete single target sites with a predetermined fractional sub-population of individual single units of the target, wherein each discrete single target site comprises a complex comprising a complex of one individual unit of said fractional sub-population of individual single units and one or more binding agent, wherein at least one binding agent comprises the enzyme;
(b) visualizing the discrete single target sites comprising the enzyme as visually distinct dots;
(c) quantifying the visually distinct dots,
(d) evaluating the amount of the target in the sample
In some embodiments, the latter method may comprise the following steps:

(a) incubating the sample with a first binding agent, wherein
   (i) said first binding agent is capable of specifically binding to a single individual unit of the target and essentially saturate all binding sites in the sample, and
   (ii) a predetermined portion of said first binding agent comprises an enzyme,
   and thereby forming discrete single target sites, each target site comprising a single individual unit of the target and the binding agent, wherein a portion of said discrete single target sites comprises the first binding agent comprising enzyme;
(b) visualizing the discrete single target sites comprising the enzyme as visually distinct dots;
(c) quantifying the visually distinct dots,
(d) evaluating the amount of the target in the sample In other embodiments the method may comprise the following steps:
(a) incubating the sample with a first and a second binding agent,
   wherein
   (i) first binding agent is capable of specifically binding to a single individual unit of the target and essentially saturate all binding sites in the sample, and
   (ii) the second binding agent is capable of specifically binding to the first binding agent and a predetermined portion of said second binding agent comprises an enzyme,
   and thereby forming discrete single target sites, each target site comprising a single individual unit of the target, the first binding and the second binding agent, wherein a portion of said discrete single target sites comprises the binding agent comprising enzyme;
   (b) visualizing the discrete single target sites comprising the enzyme as visually distinct dots;
   (c) quantifying the visually distinct dots,
   (d) evaluating the amount of the target in the sample Visualizing the secrete target sites of the invention may be done according to a recently described method for visualization of single individual units of an immobilized target in a sample (see PCT/DK2010/000137) or as described herein.

Visualization methods of the invention allow identifying essentially every single unit of the target and, thus, make determining of the absolute or relative quantity of the target in the sample possible. Both absolute and relative quantity of the target may be determined as the number of single target units in the sample in total or relative to some marker.

The methods are applicable to any sample comprising a target that is detectable by a binding agent that has affinity to that target, wherein the target is immobilized in/on to a solid support. Thus, virtually any immobilized target, such as molecules, particles or microorganisms can be detected and precisely quantified by the methods of the invention.

Precise quantification of a target is secured in the methods of the invention by use of a particular target vitalization technique and use well-defined binding agents for target detection (the details of both are described below).

The methods of the invention are particular advantageous for precise target quantification in complex histological samples, e.g. for quantification of diagnostic or therapeutic targets such as growth factor receptors, e.g. Her2 or the like, and thus, their utility in diagnostic and therapeutic application cannot be overrated. Suitability of the methods for both manual and automatic evaluation of a precise quantity of a target in samples can be mentioned as an additional valuable feature of the methods.

Visualization system used in the present invention also allows visualizing two or more different targets in the same sample (see for details WO2011047680), accordingly, absolute or relative quantification two or more targets in one sample may be performed using the methods of the invention.

Furthermore, the methods of the invention may be applied to any system allowing visualizing single units of immobilized target in histological and other samples, wherein said system comprises a step of using binding agents which has specific affinity to their binding partners in the sample.

In the methods of the invention, it may be advantageous to use a kit-of-parts that is composed of reagents useful for visualization of immobilized target units in samples, in particular the invention relates to a kit-of parts comprising a binding agent capable of specifically binding to a binding partner, wherein a predetermined portion of said binding agent comprises an enzyme. Some non-limiting embodiments of the kit-of-parts of the invention include the binding agent which is a member of a specific binding pair, e.g. an antibody or a nucleic acid; the binding partner which is a target in a sample; the binding partner which is another binding agent, e.g. wherein the another binding agent is a binding agent that is capable of binding to a target in a sample; the target which is a biological or chemical target molecule, particle, molecular or cellular complex, molecular or cellular structure, virus or microorganism, or a fragment of said target molecule, particle, complex, structure, virus or microorganism; the enzyme which is an enzyme with oxidoreductase activity, e.g. and enzyme with peroxidase or phenoloxidase activity, such as Horseradish Peroxidase (HRP) or the like. In one embodiment, a kit-of-parts of the invention may comprises a reference sample, wherein the quantity of single units of a target is predetermined, e.g. a reference cell line expressing a particular protein, wherein the number of molecules of the protein is predetermined.

In one aspect, the invention relates to a method for diagnosing or predicting a disease, or for predicting efficacy of a therapeutic treatment in an individual, comprising a step of evaluating the amount of a biological marker relating to said disease or said therapeutic treatment in a sample obtained from said individual according to a method of the invention.

Diagnostic and therapeutic applications may include, but not limited to detecting and quantifying molecular targets that are biomarkers of diseases, e.g. knowing the levels of different growth factor receptors, such as e.g. Her2 FGFR, or the like, have been shown are essential for diagnostic and treatment of cancer, and determining a particular course of therapeutic treatment is now more and more based on the results of a disease biomarker quantification.

DETAILED DESCRIPTION OF THE INVENTION

Figure 1:
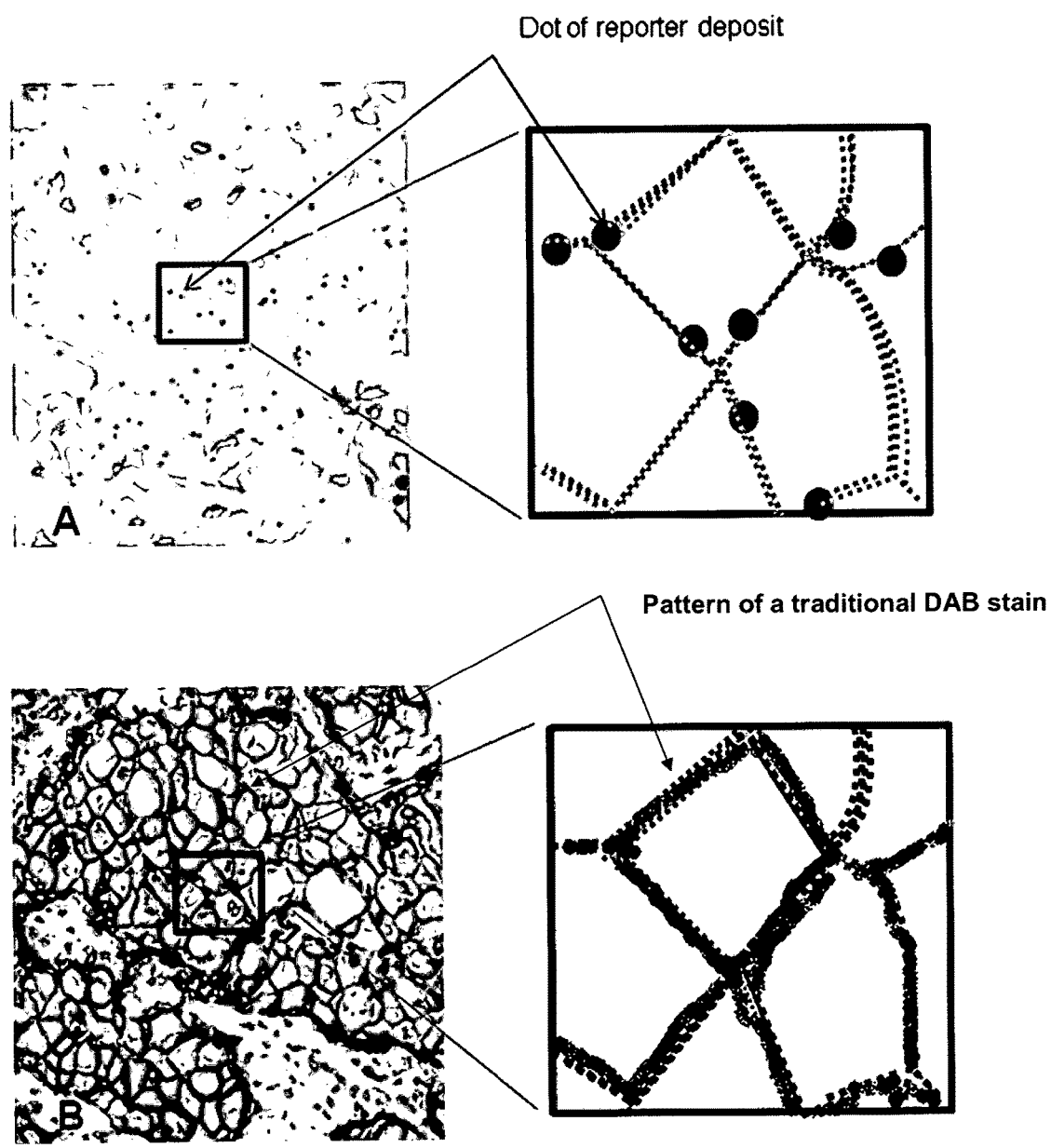
FIG. 1 shows an exemplary staining of histological slides according to a traditional HRP-DAB method (B) and according to the invention (A).
Figure 2:
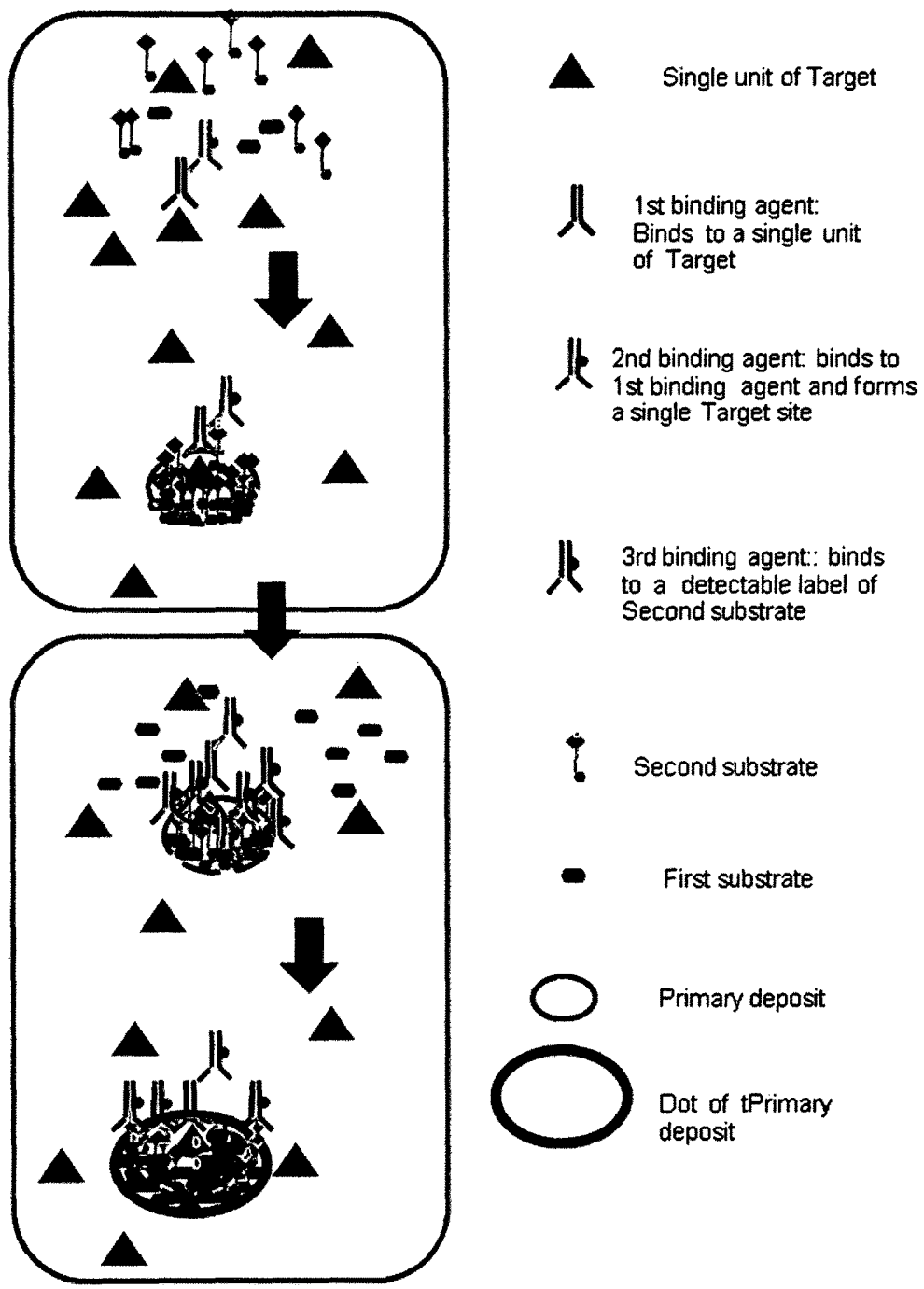
FIG. 2 shows a schematic presentation of formation of a visually distinct dot at the target site.

In general, the present invention relates to methods comprising detecting, visualizing and quantifying a target present in a sample, wherein the target is immobilized. In particular, the invention relates to methods for visualization of single molecular targets and quantification thereof in biological samples, however, the methods of the invention are not limited to biological samples or molecular targets, which is obvious from the discussion below.

One aspect of the present invention relates to a method for quantifying a target present in a sample, wherein said target is immobilized, comprising
(a) incubating a sample comprising a population of individual units of the target with one or more binding agents,
wherein
(i) at least one of the binding agent is capable of specifically binding to a single individual unit of the target, and
(ii) at least one of the binding agents comprises an enzyme, and
(iii) the binding affinity of at least one of the binding agents of (i) or (ii) to its binding partner in the sample is known,
and thereby forming one or more discrete single target sites with a fractional sub-population of individual single units of the target, wherein each discrete single target site comprises a complex of one individual unit of the target and one or more binding agent, wherein at least of the one binding agents comprises the enzyme;
(b) visualizing the discrete single target sites as visually distinct dots;
(c) quantifying the visually distinct dots,
(d) evaluating the amount of the target.

In indifferent embodiments the target sites may be formed with majority or minority of single individual units of the target present in the sample.

Another aspect of the present invention relates to a method for quantifying a target present in a sample, wherein said target is immobilized, comprising
(a) incubating a sample comprising a population of individual units of the target with one or more binding agents,
wherein
(i) at least one of the binding agent is capable of specifically binding to a single individual unit of the target, and
(i) at least one of the binding agents comprises an enzyme,
and thereby forming one or more discrete single target sites with a predetermined fractional sub-population of individual single units of the target, wherein each discrete single target site comprises a complex comprising a complex of one individual unit of said fractional sub-population of individual single units and one or more binding agent, wherein at least one binding agent comprises the enzyme;
(b) visualizing the discrete single target sites comprising the enzyme as visually distinct dots;
(c) quantifying the visually distinct dots,
(d) evaluating the amount of the target in the sample In some embodiments, the latter method may comprise the following steps:
(a) incubating the sample with a first binding agent, wherein
(i) said first binding agent is capable of specifically binding to a single individual unit of the target and essentially saturate all binding sites in the sample, and
(ii) a predetermined portion of said first binding agent comprises an enzyme,
and thereby forming discrete single target sites, each target site comprising a single individual unit of the target and the binding agent, wherein a portion of said discrete single target sites comprises the first binding agent comprising enzyme;
(b) visualizing the discrete single target sites comprising the enzyme as visually distinct dots;
(c) quantifying the visually distinct dots,
(d) evaluating the amount of the target in the sample In other embodiments the method may comprise the following steps:
(a) incubating the sample with a first and a second binding agent,
wherein
(i) first binding agent is capable of specifically binding to a single individual unit of the target and essentially saturate all binding sites in the sample, and
(ii) the second binding agent is capable of specifically binding to the first binding agent and a predetermined portion of said second binding agent comprises an enzyme,
and thereby forming discrete single target sites, each target site comprising a single individual unit of the target, the first binding and the second binding agent, wherein a portion of said discrete single target sites comprises the binding agent comprising enzyme;
(b) visualizing the discrete single target sites comprising the enzyme as visually distinct dots;
(c) quantifying the visually distinct dots,
(d) evaluating the amount of the target.

Using any of the methods of the invention, in different preferred embodiments the amount of the target may be evaluated as a fractional amount of the target in the sample (which corresponds to a fractional sub-population of individual single target units in the sample); as the total amount of the target (or the total amount of individual single target units) in the sample (termed herein also as "absolute amount"); as a relative amount of the target (a relative amount of the target or single units of the target to another target, reference marker, etc).

According to the invention, amount of the target in samples stained according to the invention may be evaluated manually, i.e. the dots may be counted by an observer using available microscopic optics. In other embodiments, images of the stained samples may be captured and processed automatically, using available in the art software. Some non-limiting examples of procession of the stained samples are described in EXAMPLES.

In one embodiment, a target in a sample may be visualized and amount of the target evaluated using a kit-of-parts of the invention.

A kit comprising parts for quantification of an immobilized target in samples is another aspect of the invention. In particular, a kit-of-parts of the invention, in one embodiment, may comprise a binding agent that is a mixture of binding molecules wherein a predetermined portion of said binding molecules is labeled with an enzyme. In other embodiments, a kit-of-parts of the invention may comprise any of the reagents included in claims and, optionally, instructions for use. In one embodiment, a kit-of-parts of the invention may comprises a reference sample, wherein the quantity of single units of a target is predetermined, e.g. a reference cell line expressing a particular protein, wherein the number of molecules of the protein is predetermined.

One aspect of the invention is a method for diagnosing or predicting a disease, or for predicting efficacy of a therapeutic treatment in an individual, wherein said method comprising a step of evaluating the amount of a biological marker relating to said disease or said therapeutic treatment in a sample obtained from said individual according to a method of the invention. Accordingly, a kit-of-parts of the invention may serve as part of a diagnostic kit.

Diagnostic and therapeutic applications may include, but not limited to detecting and quantifying molecular targets that are biomarkers of diseases, e.g. knowing the levels of different growth factor receptors, such as e.g. Her2 FGFR, or the like, have been shown are essential for diagnostic and treatment of cancer, and determining a particular course of therapeutic treatment is now more and more based on the results of a disease biomarker quantification. Accordingly, a kit-of-parts of the invention may comprise instructions teaching the user how to correlate the amounts of biomarkers defined in samples according to the methods of the invention to diagnosis, prognosis or treatment of the relevant disease.

The above and other aspects and non-limiting embodiments of the invention are discussed in detail below and in EXAMPLES.

Sample

The term "sample" means a representative part or a single item from a larger whole or group, an amount or portion of a matter or object that supposedly contain a target to be detected, e.g. a portion or amount of biological, chemical, environmental material comprising a target molecule, particle, structure to be analyzed, e.g. a biopsy sample, a food sample, a soil sample, etc. A typical sample shows what the rest of the matter or object is or should be like. In one embodiment a sample of the invention may be an environmental sample, e.g. a sample of a soil or a sample of a spillage. In another embodiment the sample may be a food sample. In another embodiment the sample may be a portion of a library of organic molecules. In another embodiment the sample may be a sample of warfare. In one preferred embodiment a sample of the invention is a biological sample.

A biological sample may be:
1. a sample comprising suspended cells and/or cells debris, e.g. blood sample, suspension of cloned cells, body tissue homogenate, etc;
2. a sample comprising of intact or damaged cells of an animal body, a body tissue, smear or fluid or a sample of a tumor, e.g. a biopsy sample; It may be a fresh tissue sample or preserved tissue sample, e.g. a formalin fixed paraffin embedded tissue sample;
3. a sample comprising a living organism, e.g. a sample of a medium comprising an animal, plant, bacterium, fungi, etc;
4. a sample comprising viral particles, debris thereof, or viral products, e.g., a body smear comprising viral nucleic acids, proteins, peptides, etc;
5. a sample comprising a cell organelle(s);
6. a sample comprising natural or recombinant biological molecules, e.g. blood plasma sample, conditioned cell culture media, etc.
7. a sample comprising plant cells or derbies thereof.

The above mentioned embodiments of biological samples are exemplary and for the purpose of illustration, but not limitation, of the invention.

Examples of chemical samples may be illustrated by and are not limited to samples of libraries of chemical compounds, e.g. peptide libraries. Examples of the environmental samples may be illustrated by and are not limited to soil, water or air samples and food samples.

The invention relates to samples (e.g. as any of the above) comprising an immobilized target, i.e. to samples, where the target is prevented from freedom of movement during a detection procedure of the present invention, e.g. samples, where the target motion is substantially reduced or eliminate by mechanical or chemical means, as e.g. in case of samples or targets attached to or within a certain support or medium. Thus, a sample comprising single individual units of a target of interest may in one embodiment be immobilized onto a solid support before the detection procedure, e.g. a solid body tissue sample immobilized on a glass slide. Examples of samples comprising immobilized targets of the invention include but not limited to body tissue samples immobilized on glass or plastic slides, or to samples comprising biological or chemical molecules immobilized onto membranes or ELISA plates, etc. A target of a sample in these embodiments may be immobilized either within the sample, e.g. a protein fixed within a tissue sample, or is immobilized on the surface or within certain material, such as e.g. a portion of a solid material or a gel such as a nitrocellulose membrane, etc. In one embodiment the solid support may be a three-dimensional structure, e.g. a collagen or agar block. In this embodiment a target, e.g. molecule or particle may be immobilized within the structure.

In one embodiment the invention relate to a sample that does not comprise the target, e.g. a control sample. In another embodiment, the invention relate to a sample that supposedly comprise the target, e.g. a sample with unknown content.

The term "solid support" mentioned above means a piece of any material that is insoluble under conditions of the procedures according to the invention, e.g. it may be a nitrocellulose membrane, glass slide etc. Examples of supports suitable for immobilizing samples and/or targets include but not limited to synthetic polymer supports, such as polystyrene, polypropylene, substituted polystyrene, e.g, aminated or carboxylated polystyrene; polyacrylamides; polyamides; polyvinylchloride; glass; agarose; nitrocellulose; nylon; polyvinylidenedifluoride; surface-modified nylon, etc. The invention relates to a solid support that is chemically inert under conditions described herein, i.e. the chosen support may not have any major influence on the results of detection by the method. Accordingly, any such inert support suitable for immobilizing a sample or target fitting the chosen assay format, e.g. for IHC, ELISA, blotting etc, may be selected Target The term "target" means in the present content an object of interest supposedly present in a sample that can be characterized by particular physical and/or functional features. It is understood that in the context of the invention the term "target" relates to the whole pool of substantially identical entities of that object, not to a single entity of that object in a sample; in samples where a target is represented by the only single unit, this only single target unit is to be understood as the target at whole and as the quantity of the target in the sample. The term "substantially identical" in the present context means that all or substantially all single entities of the total pool of a target in a sample possess one or more features that make them recognizable as the target. For example, the target may, be a particular protein including all molecules of that particular protein in a sample; another example of a target of the invention may be a particular molecular complex or structure including substantially all objects of the sample that comprise that particular molecular complex or molecular structure; another example of a target of the invention may be a viral particle or a bacterium, wherein total population of that viral particles or that bacteria of the sample is the target.

Biological objects such as molecules, molecular complexes, structures, particles or organisms which are associated with features that are characteristic for a particular cell type, tissue, cellular structure, physiological condition, etc., are often termed "biological markers" of that particular cell type, tissue, cellular structure, or physiological condition. Non-limited examples of such biological markers include but not-limited to particular nucleotide sequences, proteins or other biological molecules, e.g. carbohydrates or lipids, chromosomal or membrane structures, viruses, bacteria, microorganisms etc. In some embodiments of the invention, the term "target" is used interchangeable with the term "biological marker" and relates to a molecule, molecular complex, structure or particle that is characteristic for a particular cell type, tissue, physiologic condition, etc, wherein the total population of any of the latter biological markers in the test sample is considered to be the target.

In one embodiment, the target may be a protein, e.g. a cellular membrane receptor or a cytoplasmic protein, in another embodiment the target may be a nucleic acid, e.g. a cytoplasmic nucleic acid. Derivatives of any latter mentioned targets, e.g. fragments, precursors, mutants of target proteins or nucleic acids, etc. may also be targets in some embodiments of the invention.

Thus, in different embodiments of the invention the target may be a biological or chemical target molecule, or a particle, or a molecular or cellular complex, or molecular or cellular structure, or a virus, or a microorganism, or a fragment of said target molecule, particle, complex, structure, virus or microorganism. Among targets contained in chemical and environmental samples may be different pollutants, toxins, warfare substances, members of molecular libraries, industrial noxious waste compounds, etc.

In particular the invention relates to targets that may be represented in a sample by a plurality of independent substantially identical units, in particular the invention relates to single individual units of a target.

By the term "unit" is meant a single quantity of a target regarded as a whole in calculation and serving to perform one particular function. The term "individual" means that a unit is separable from the other units of the same kind or other components of the environment (by physical features of a function) and can be considered and counted separately. The term "individual unit" is interchangeably used with the term "single unit". The term "single" in the present content means a target unit is consisting of a separate whole, is consisting of only one in number, is consisting of one as opposed to or in contrast with many. For example a single/individual unit of a target protein means a single individual protein molecule of the target protein, i.e. one molecule of plurality molecules of the same kind. The term "substantially identical units" means that a plurality of single units of a target possesses one or more features that make these units be considered as the target. The term "independent" means that a single unit of a target exists as a distinct entity and do not depend on the existence of other distinct entities of the same kind in the sample.

The invention is some embodiments relate to a single unit being a single part of a molecule. The term "single part of molecule" relates to a part of a molecule that has particular properties that allow considering this part of the molecule separately from the other parts of the same molecule, e.g. a proteolytic fragment of a target protein, a part of a fusion protein, a particular domain of a target protein, a particular structure of a nucleic acid, an epitope, etc.

Thus, in one embodiment, the invention may relate to single/individual units of a target being single individual target molecules, i.e. to a plurality of single individual target molecules present in a sample, in another embodiment the invention may relates to single/individual units of a target being single individual parts of a molecule, e.g. a particular molecular structures that presents in a plurality target molecule in a sample, e.g. an epitope. In another embodiment the invention may relate to a plurality of single individual viral particles making a pool of viral particles present in a sample.

In different embodiments a plurality of single units of a target may be represented by single individual biological or chemical molecules, single individual single particles, single individual molecular or cellular complexes, single individual molecular or cellular structures, or single individual viruses or single individual microorganisms, or single individual fragments of said molecules, particles, complexes, structures viruses or microorganisms.

In one preferred embodiment, the target is a biological marker related to cancer, e.g. nucleic acids and polypeptides of hormones and growth factors and their receptors, cell adhesion molecules signal transduction molecules, cell cycle regulation molecules, etc, e.g. genes, RNAs and proteins of the group including growth factors PDGF, VEGF, TGF, HGF or EGF, their receptors and the pathway related molecules, genes and their products relating to signal transduction pathways, e.g. the JAK/STAT pathway or Akt1/PKB cell survival pathway, or 5-FU pathway, estrogen receptor ER and its gene (ERS1), etc. The methods of the invention allow a simple and rapid visualization and quantification of said biological markers.

The methods of the invention allow visualizing and quantifying single individual units of a target present in a sample in a broad dynamic range. Both very high amounts and very low amounts of a target may be visualized and quantified in one and the same sample, or they may be evaluated in separate samples. Two or more different targets may be visualized in one or the same sample, e.g. a protein target and nucleic acid target, or two or more different protein targets, or two or more different nucleic acid targets, etc.

In one embodiment, single units of a target may be distributed substantially homogeneously throughout a sample, in other embodiments, single units of a target may present more abundant in one part of a sample and less abundant in other parts thereof. In all the latter embodiments, single units of the target may be visualized and quantified in one and the same sample using methods of the present invention. In some embodiments, wherein a single target unit is associated with another target of interest, e.g.

present in a particular molecular association or a structure which said particular association or structure is a biomarker of a pathological condition. said another target of interest may be visualized and quantified by visualizing and quantifying single target units in the sample as well.

In one embodiment, the invention relate to a fractional sub-population of single target units present in a sample, such as a majority or a minority of the total number of single individual target units present in the sample. The term "fractional subpopulation" in the present context means a portion of the total population of single target units that is equal or less than 99.9%. e.g. equal or less than 98%, 97%, 95%, 94%, 93%, 92%, 91% or 90% of the total quantity of single units of the target in the sample, such as between 90% and 85%, less than 85%, e.g. 85%-80%, 80%-75% of the total quantity of units of the target in the sample, such as less than 75%, for example from 1% to 74% of the total quantity of single units of the target in the sample, such as from 1% to 60%, 1% to 50%, 1% to 40%, 1% to 30% or 25% of the total quantity of units of the target in the sample, etc. A fractional sub-population single target units that is represented by 50%-99.9% of the total population is defined according to the invention as a majority of single target units present in the sample. A fractional sub-population is represented by less than 50% of the total population of single target units in a sample is defined according to the invention as a minority of single target units present in the sample In one embodiment, a majority of individual single target units may be involved in formation of discrete single target sites of the invention; in another embodiment, a minority of individual single target units may be involved in formation of discrete single target sites of the invention. In one embodiment, it may be preferred that substantially all individual single units of a target are involved in formation of complexes with one or more binding agents, wherein only a fractional sub-population of said complexes is involved in formation of discrete single binding sites of the invention.

Binding Agent

Methods of the invention comprise a step wherein a sample presumably comprising a target is incubated with one or more binding agents.

The term "binding agent" designates a molecule that is capable of directly or indirectly specifically binding to a single unit of a target, e.g. an individual molecule of a target .protein. The term "specifically" means that the binding agent has a particular affinity to the target, e.g. affinity to a target molecule, or particular affinity to an agent that is bound to the target, e.g. affinity to a primary antibody bound to a target protein, affinity to a hapten conjugated with a primary antibody, etc. The term "directly" means that a binding agent having a specific affinity to a single individual unit of target interacts and forms an immediate bond with this single individual unit upon interaction, e.g. a primary antibody binds directly to a single individual target molecule that was used as an antigen for raising said primary antibody. The term "indirectly" in the present context relates to a binding agent, wherein said binding agent has no specific affinity to a single individual unit of the target, but wherein said binding agent has a specific affinity to another substance that is capable of specifically binding to that single individual unit, e.g. a primary antibody, or wherein said binding agent has a specific affinity to a substance that is associated or linked to said single individual unit, e.g. to a hapten; said binding agent directly interacts with the latter substances and forms a bond with said substance, and thereby the binding agent becomes indirectly bound to the single unit of the target.

A binding agent which is capable of directly specifically binding to a single unit of target is typically represented herein by a first binding agent. A binding agent which is capable of indirectly specifically binding to a single unit of target is typically represented by a second binding agent. However, a detection system according to the invention may comprise further binding agents that can be indirectly bound to the single unit of the target, e.g. third, fourth, and further binding agents.

Typically, a first binding agent or, in some embodiments, a second or third binding agent, is used to contact the sample to recognize the target, bind to it and form a complex with it. Second, third and further binding agents may be used in further steps of methods according to the invention, e.g. for recognition of deposits of detectable molecules at target sites described below. In some embodiments, second, third and further binding agents are used to amplify a signal associated with a target. These binding agents are also useful to add flexibility to the detection system, e.g. to change the original signal associated with the target, e.g. a red fluorescent signal to green, etc, Binding agents of the invention may be members of different specific binding pairs.

A number of different specific binding pairs are known in the art, these are the pairs of two different molecules which are capable of specific binding to each other. Members of specific binding pairs suitable for use in practicing the invention may be of the immune or non-immune type.

Non-immune specific binding pairs include systems wherein the two components share a natural affinity for each other but are not antibodies. Exemplary non-immune binding pairs are biotin-avidin or biotin-streptavidin, folic acid-folate binding protein, complementary nucleic acids, receptor-ligand, etc. The invention also includes non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino)benzoic acid (DMAB), etc.

Immune specific binding pairs may be exemplified by antibody-antibody systems or hapten-anti-hapten systems. In one embodiment the immune specific binding pair of the invention may be an antibody-antibody binding pair comprising two or more antibody molecules having affinity to each other, for example a primary antibody and secondary antibody pair, wherein the primary antibody represents the first binding agent and the secondary antibody represents the second binding agent; Antibody systems comprising 3 or 4, or more antibody members may be used in another embodiment. In other embodiments of the invention the immune binding pair may be represented by a hapten-anti-hapten system. In such embodiments the first binding agent may be represented by a conjugate comprising a molecule having affinity to the target and a hapten, e.g. a primary antibody or nucleic acid sequence linked to a hapten, and the second binding agent may be represented by an anti-hapten antibody.

The term "hapten" designates a small molecule which can be considered as an isolated epitope to which an antibody can be made, although the hapten alone will not induce an immune response if injected into an animal, it must be conjugated to a carrier (usually a protein). As haptens are small molecules, multiple copies of a hapten may be attached to a large molecule, e.g. a polymer molecule, such as protein, nucleotide sequence, dextran, etc. Haptens may serve as convenient label molecules for assay formats where it is necessary or advantageous to amplify a signal. Thus, the bound multiple copies of a hapten provide for enhanced sensitivity, e.g. increased signal strength. Non-limited examples of suitable haptens include Fluorescein (FITC), 2,4-Dinitrophenol (DNP), myc Digoxigenin (DIG), tyrosine, nitrotyrosine biotin and dyes. e.g. tetramethylrhodamine, Texas Red, dansyl, Alexa Fluor 488, BODIPY FL, lucifer yellow and Alexa Fluor 405/Cascade Blue fluorophores, Haptens are described in US20080305497 may also be used for the purposes of the invention.

The term "antibody", as used herein, designates an immunoglobulin or a part thereof, and includes any polypeptide comprising an antigen binding site regardless of the source, method of production, and other characteristics. The term includes for example, polyclonal, monoclonal, monospecific, polyspecific, humanized, single chain, chimeric, synthetic, recombinant, hybrid, mutated, and CDR-grafted antibodies. A part of an antibody can include any fragment which can still bind antigen, for example, an Fab, F(ab')$_2$, Fv, scFv. The origin of the antibody is defined by the genomic sequence irrespective of the method of production.

Primary antibody, in context of the present invention, refers to an antibody binding agent, e.g. a whole antibody molecule, a fragment or a derivative of said molecule, e.g. a conjugate comprising an antibody or a polymerized antibody, that specifically binds to a target, more specifically to a single unit of a target of a sample, e.g. to a single target molecule. In some embodiments, a primary antibody may be a bivalent antibody which is capable of binding to two (or more) single individual units of different targets, e.g. an antibody that is capable of binding to a receptor dimer, e.g. Her2/Her3 dimer. In this embodiment the single unit of a target according to the invention is a single Her2/Her3 dimer, and the target is a population of Her2/her3 dimers in a sample including all said dimers of the sample. Primary antibodies may be derived from any warm blooded species, e.g. mammals, birds.

Secondary antibody, in context of the present invention, refers to an antibody binding agent, e.g. a whole antibody molecule, a fragment or a derivative of said molecule, e.g. a conjugate comprising an antibody or a polymerized antibody, that has an antigen binding domain that specifically binds to the primary antibody, or a hapten deposited in the target site, or hapten linked directly or indirectly to a primary antibody or another binding agent.

Tertiary antibody, in context of the present invention, refers to an antibody binging agent, e.g. a whole antibody molecule, a fragment or a derivative of said molecule, e.g. a conjugate comprising an antibody or a polymerized antibody that comprise an antigen binding domain that specifically binds to a secondary antibody or a hapten linked to a secondary antibody or a hapten linked to polymer conjugated to a secondary antibody, or hapten deposited in the target site.

Sometimes an antibody may function both as a secondary and a tertiary antibody.

Antibodies used in the invention, including primary antibodies, secondary antibodies and tertiary antibodies, may be derived from any mammal species, e.g., a rat, a mouse, a goat, a guinea pig, a donkey, a rabbit, horse, lama, camel, or any avian species e.g., chicken, duck. Derived from any mammal or avian species, as used herein, means that at least a part of the nucleic acid sequence encoding a particular antibody originated from the genomic sequence of a specific mammal, e.g., a rat, a mouse, a goat, or a rabbit or a specific bird e.g., chicken, duck. The antibody may be of any isotype, e.g., IgG, IgM, IgA, IgD, IgE or any subclass, e.g., IgG1, IgG2, IgG3, IgG4.

In certain embodiments a primary antibody contains an antigen binding region which can specifically bind to a biological marker, in particular to a single individual unit of said biological marker, expressed by cells of a biological sample. The marker may be expressed on the cell surface or within the cell membrane, i.e., on the interior of the cell, e.g., within the cytoplasm, within the endoplasmic reticulum, etc. In some embodiments the biological marker may be extracted from the cell and thus it is present in a cell-free medium, e.g. in an aqueous solution, or it is a soluble molecule present in a cell culture media, blood plasma, cerebrospinal fluid, etc. Examples of the corresponding samples are described above.

In certain embodiments, a secondary antibody contains an antigen binding region which specifically binds to a primary antibody, e.g., to the constant region of the primary antibody. In certain embodiments, a secondary antibody may be conjugated to a polymer. In some embodiments, 2-20 secondary antibodies, such as 5-15 secondary antibodies may be conjugated with a polymer. In other embodiments, a polymer may be conjugated with 1-10 secondary antibodies, such as 1, 2, 3, 4, 5, 6, 7, 8, 9 or 10 secondary antibodies.

In certain embodiments, a tertiary antibody may contain an antigen binding region which specifically binds to a secondary antibody, e.g., to a constant region of a secondary antibody, or to a hapten linked to a secondary antibody, or to a polymer conjugated with a secondary antibody. In certain embodiments, a tertiary antibody is conjugated to a polymer. In some embodiments, 1-20 tertiary antibodies may be conjugated a polymer. In other embodiments, 1-5 tertiary antibodies, such as 1, 2, 3, 4 or 5 tertiary antibodies may be conjugated with a polymer.

In some embodiments, polymers comprising a single binding unit of a binding agent, e.g. a polymer conjugated with one molecule of primary, secondary or tertiary antibody, may be preferred.

Antibodies that may be used for the purposes of the invention include monoclonal and polyclonal antibodies, engineered antibodies including chimeric, CDR-grafted and artificially selected antibodies produced using phage display or alternative techniques.

Antibody binding agents of the invention may be produced by any of numerous methods well-known in the art e.g., according to Harlow and Lane, *Antibodies: a Laboratory Manual*, (1988) (Cold Spring Harbor Press, Cold Spring Harbor, N.Y.). Techniques for the preparation of recombinant antibody molecules are described in the above reference and a number of other references, e.g., EP 0623679; EP 0368684; and EP 0436597. Nucleic acids encoding antibodies may be isolated from a cDNA library. Nucleic acids encoding antibodies may be isolated from a phage library (see e.g. McCafferty et al. 1990, *Nature* 348:552, Kang et al. 1991, *Proc. Natl. Acad. Sci. USA* 88:4363; EP 0 589 877 B1). Nucleic acids encoding antibodies can be obtained by gene shuffling of known sequences (Mark et al. 1992, *Bio/Technol.* 10:779). Nucleic acids encoding antibodies can be isolated by in vivo recombination (Waterhouse et al. 1993, *Nucl. Acid Res.* 21:2265). The antibodies used in the methods of the invention include humanized immunoglobulins (see U.S. Pat. No. 5,585,089, Jones et al. 1986, *Nature* 332:323). Antibodies of the invention may be altered any possible way, presuming that they retain their binding affinity, e.g, they may fused with an effector protein, toxin, label, etc. Methods of conjugation of antibody with different agents are also well known in the and described in exemplary embodiment of the invention below.

In one embodiment of the invention, an antibody binding agent is represented by the Fab region.

In one embodiment an antibody binding agent may be a composition comprising two or more different antibody binding agents, e.g., a composition comprising a first antibody binding agent and a second antibody binding agent, wherein the two or more different antibody agents are of different immune binding pairs. In one embodiment, in the composition, at least one of two or more different antibody binding agents of is an antibody that is capable of specifically binding to a target and at least one another is an antibody which comprises a an enzyme.

In another embodiment, the invention relates to binding agents that are members of non-immune specific binding pairs, such as complementary nucleotide sequences, or nucleic acid analog molecules.

A binding agent comprising a nucleic acid or nucleic acid analog molecule, e.g., a DNA molecule, an RNA molecule, a PNA molecule, may be useful for the visualization and quantification of single individual units of nucleic acid targets.

Nucleic acid sequences used as binding agents for the purposes of the invention may be synthesized chemically or produced in recombinant cells. Both modes of production are well known in ht eart (see e.g. Sambrook et al. (1989) *Molecular Cloning: A Laboratory Manual*, 2nd ed. Cold Spring Harbor Press). In some embodiments, a nucleic acid binding agent may comprise a peptide nucleic acid (PNA). A peptide nucleic acid is a nucleic acid molecule in which the deoxyribose or ribose sugar backbone, usually present in DNA and RNA is replaced with a peptide backbone. Methods of making PNAs are known in the art (see e.g. Nielson, 2001, *Current Opinion in Biotechnology* 12:16) (hereby incorporated by reference). In other embodiments, the binding agent may comprise a locked nucleic acid (LNA) (Sorenson et al. 2003, *Chem. Commun.* 7(17):2130).

A nucleic acid binding agent, in some embodiments, may comprise at least one oligo- or at least one polynucleotide sequence that specifically hybridizes to a single unit of a target sequence in a biological sample, e.g. a single mRNA sequence, under specific conditions of stringency. The term "hybridization under stringent conditions," is used herein to describe conditions for hybridization under which nucleotide sequences that are significantly complementary to each other, such as at least 70%, at least 80%, at least 85-90% complementary, remain bound to each other. The percent complementary is determined as described in Altschul et al. (1997) *Nucleic Acids Res.* 25:3389-3402 (hereby incorporated by reference).

Specified conditions of stringency are known in the art and can be found in *Current Protocols in Molecular Biology*, John Wiley & Sons, Inc. (Ausubel et al. 1995 eds.), sections 2, 4, and 6 (hereby incorporated by reference). Additionally, specified stringent conditions are described in Sambrook et al. (1989) *Molecular Cloning: A Laboratory Manual*, 2nd ed. Cold Spring Harbor Press, chapters 7, 9, and 11 (hereby incorporated by reference). In some embodiments, the hybridization conditions are high stringency conditions. An example of high stringency hybridization conditions is hybridization in 4× sodium chloride/sodium citrate (SSC) at 65-70° C. or hybridization in 4×SSC plus 50% formamide at 42-50° C., followed by one or more washes in 1×SSC, at 65-70° C. It will be understood that additional reagents may be added to hybridization and/or wash buffers, e.g., blocking agents (BSA or salmon sperm DNA), detergents (SDS), chelating agents (EDTA), Ficoll, PVP, etc.

In some embodiments, the binding agents may hybridize to a target sequence in a sample under moderately stringent conditions. Moderate stringency, as used herein, include conditions that can be readily determined by those having ordinary skill in the art based on, for example, the length of the DNA. Exemplified conditions are set forth by Sambrook et al. *Molecular Cloning: A Laboratory Manual*, 2d ed. Vol. 1, pp. 1.101-104, Cold Spring Harbor Laboratory Press (1989) (hereby incorporated by reference), and include use of a prewashing solution of 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

In some embodiments, the binding agents hybridize to a target sequence in a sample under low stringent conditions. Low stringency conditions may include, as used herein, conditions that can be readily determined by those having ordinary skill in the art based on, for example, the length of the DNA. Low stringency may include, for example, pretreating the DNA for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5-20×10$^6$CPM binding agent is used. Samples are incubated in hybridization mixture for 18-20 hours at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C.

In other embodiments the invention may relate to binding agents that are peptide sequences or comprise peptide sequences that are derived from non-antibody proteins, e.g. peptide sequences derived from nucleic acid binding domains of different proteins, ligands of different cellular and nuclear receptors and their derivatives. Some non-limiting examples of such binding agents may be c1q protein of the classical pathway of the complement cascade which can bind to an antibody constant region, a MHC molecule, e.g., MHC class I and MHC class II and non conventional MHC, a molecule having a specific binding partner, such as molecules involved in cellular signaling pathways such as molecules having leucine zipper domains, e.g., fos/jun, myc, GCN4, molecules having SH1 or SH2 domains, such as Src or Grb-2; an immunoglobulin receptor, e.g., an Fc receptor; a chimeric protein, i.e., a protein engineered to combine the features of two or more specific binding partners, e.g., a leucine zipper could be engineered into a Fc region of an antibody, an SH2 domain could be engineered to be expressed in a Fc region of an antibody. In other embodiments, fusion proteins can be engineered comprising an Fc portion of an antibody with a substituted variable domain.

The binding agent may also be small molecules which can bind specifically to certain structural units of large biological molecules.

In some embodiments binding agents may comprises a detectable label, e.g. a fluorescent substance, hapten, enzyme, etc. In one embodiment, the invention relates to labeled binding agents, i.e. labeled first, second, third or further binding agents, that are capable of specifically binding to their binding partners in the sample, e.g. units of the target, other binding agents, deposited detectable molecules.

Such binding agents may be used for visualization target units in the sample or target sites of the invention. In one embodiment, the invention relates to a binding agent comprising a label which is an enzyme. Non-limiting examples of suitable enzyme labels may be horseradish peroxidase (HRP), alkaline phosphatase (AP), beta-galactosidase (GAL), glucose-6-phosphate dehydrogenase, beta-N-acetyl-glucosaminidase, β-glucuronidase, invertase, xanthine oxidase, firefly luciferase, glucose oxidase (GO). In one preferred embodiment a binding agent may comprise HRP as a label. In another preferred embodiment, a binding agent may comprise AP as a label. Other preferred enzyme embodiments are discussed below.

Amounts of binding agents necessary for forming target sites of the invention may vary depending on different factors, e.g. sample species, target species, binding agent species, binding affinity of binding agents, etc. Using common general knowledge the skilled in the art can select an appropriate binding agent and determine the amount needed for every particular embodiment. In some embodiments it is preferred that the amounts of binding agents used for forming the target sites are adjusted so that not all single units of a target present in the sample, but a fractional sub-population thereof is involved in formation of the target sites, e.g. these embodiments may relate to a sample comprising a target in abundant amounts, or a target present in a broad dynamic concentration range. In other embodiments, it may be preferred that all or substantially all single units of a target are involved in formation of target sites of the invention, e.g. in case of samples with a very low target expression of a target or single units of a target. In the latter embodiments, it may be preferred to use binding agents in amounts that will secure formation of binding sites with a substantial majority of individual single units of the sample, i.e. a substantial majority of single units of a target present will be involved in formation the target sites.

In one embodiment, a binding agent may be a mixture of unlabelled and labeled binding molecules of the same species that have affinity to the same binding partner, e.g. a mixture of labeled and unlabelled primary antibody to a particular target protein, or a mixture of labeled and unlabelled secondary antibody against a particular species of primary antibodies, or the like. According to the invention, using the latter mixtures of binding molecules, wherein a portion of the labeled binding molecules is predetermined, the target sites formed (and then visualized as visually distinct dots) with a certain fractional sub-population of single target units that is predetermined by the portion of the labeled binding agent. This allow determining the precise quantity of single target units in the sample, and, thus, the quantity of the target, including a relative and total amount of the target in the sample. This and other methods of quantifying the target in a histological sample are discussed in detail in EXAMPLES.

In some embodiments, the invention relates to a binding agent, e.g. a member of a specific binding pair, which binding affinity to its specific binding partner is known, e.g. predetermined, binding affinity to its binding partner in the sample, e.g. to a target or another binding agent.

The affinity between members of specific binding pairs is commonly described by the dissociation constant, e.g. ligand and receptor, antibody and antigen, and the like, i.e. how tightly one binding partner (BP1) binds to another binding partner (BP2) of the pair.

The formation of a complex between the binding partners (BP1:BP2) can be described by a two-state process:
BP1:BP2<=>BP1+BP2;
the corresponding dissociation constant is defined $$Kd = \frac{[BP1][BP2]}{[BP1:BP2]}$$

where [BP1], [BP2] and [BP1:BP2] represent molar concentrations of the BP1, BP1 and complex of BP1 and BP2, respectively.

The dissociation constant has molar units (M), which correspond to the concentration of BP1 at which the binding site on BP2 is half occupied, i.e. the concentration of BP1, at which the concentration of BP2 with BP2 bound [BP1:BP2], equals the concentration of BP2 with no ligand bound [BP2]. The smaller the dissociation constant, the more tightly bound the BP1 is, or the higher the affinity between BP1 and BP2. For example, a BP1 with a nanomolar (nM) dissociation constant binds more tightly to a BP2 than a BP1 with a micromolar (μM) dissociation constant.

The dissociation constant for a particular BP1 to BP2 interaction can change significantly with solution conditions (e.g. temperature, pH and salt concentration). The effect of different solution conditions is to effectively modify the strength of any intermolecular interactions holding a particular BP1:BP2 complex together. Conditions of media relevant to formation of BP1:BP2 complex for the purposes of the present invention are discussed in further sections below.

In the specific case of antibodies (Ab) binding to antigen (Ag), usually the affinity constant (Ka) is used. It is the inverted dissociation constant.

$$Ab + Ag <= > Ab:Ag;$$

$$Ka = \frac{[Ab:Ag]}{[Ab][Ag]} = \frac{1}{Kd}.$$

This chemical equilibrium is also the ratio of the on-rate ($k_{forward}$) and off-rate ($k_{back}$) constants. Two antibodies can have the same affinity, but one may have both a high on- and off-rate constant, while the other may have both a low on- and off-rate constant.

$$Ka = \frac{K_{forward}}{K_{back}} = \frac{\text{on-rate}}{\text{off-rate}}.$$

A binding agent with known Kd or Ka may be obtained from a commercial provider, or Kd and/or Ka may be predetermined be any technique known to the skilled in the art. A method of determining Kd of a first and second binding agent in a histological sample using a visualization system of the invention, and use this determination for quantifying a target in a histological sample is described in the EXAMPLES.

Enzyme

According to the invention a sample comprising one or more individual unit of a target According to the invention at least one binding agent comprising an enzyme binds, directly or indirectly, a single unit of the target and forms a complex with said unit.

A preferred enzyme according to the invention is an enzyme with oxidoreductase activity (interchangeably termed herein as "oxidoreductase" or "enzyme of the invention").

By the term "enzyme with oxidoreductase activity" is meant an enzyme classified as EC 1 in the EC number classification of enzymes that catalyzes the transfer of electrons from one molecule (the reductant, also called the hydrogen or electron donor) to another (the oxidant, also called the hydrogen or electron acceptor). In some preferred embodiments, the invention relates to oxidoreductases classified as E 1.10. (phenoloxidases) and E 1.11. (peroxidases).

In one preferred embodiment the invention relates to phenoloxidases, in particular to the family of copper-containing oxidase enzymes, laccases (E 1.10.3.2). Laccases act on phenols and similar molecules, performing one-electron oxidation. Laccases play a role in the formation of lignin by promoting the oxidative coupling of lignols, a family of naturally occurring phenols. A laccase suitable for the purposes of the invention may be for example an enzyme described by Phillips L E and Leonard T J (Benzidine as a Substrate for Measuring Phenoloxidase Activity in Crude Cell-Free Extracts of Schizophyllum commune. Mycologia 1976, 68: 277-285,), or Kunamneni A, Plou F J, Ballesteros A, Alcalde M. (Laccases and their applications: a patent review. Recent Pat Biotechnol. 2008, 2(1):10-24), or Rodriguez Couto S, Toca Herrera J L (Industrial and biotechnological applications of laccases: a review. Biotechnol Adv. 2006, 24(5):500-13.)

The term "laccase" is used herein to designate an enzyme with phenoloxidase activity of, the invention, however it is understood then laccase is one of many embodiments of penoloxidase that are suitable for the purposes of the invention.

In another preferred embodiment, the invention relates to a peroxidase enzymatic activity catalyzing a reaction of the form:

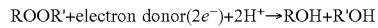

ROOR'+electron donor(2e⁻)+2H⁺→ROH+R'OH

In one preferred embodiment of the invention, the enzyme with peroxidase activity is horseradish peroxidase (HRP). In another embodiment of the invention, the enzyme with peroxidase activity is soyabean peroxidase (SP).

For some peroxidases the optimal substrate is hydrogen peroxide, some others are more active with organic hydroperoxides such as organic peroxides. The nature of the electron donor is very dependent on the structure of the enzyme, e.g. horseradish peroxidase (HRP) can use a variety of organic compounds both as electron donors and acceptors. HRP has an accessible active site, and many compounds can reach the site of the reaction.

The enzymatic activity, i.e. oxidireductase activity, e.g. phenoloxidase or peroxidase activity, may be represented by a full-length molecule of an enzyme which is directly or indirectly linked to the molecule of a binding agent, or a fragment of the enzyme conflated with the enzymatic activity, e.g. 51% to 99.9% of the full size of the enzyme molecule, or less than 51%, e.g. 40%, 30% or less.

A binding agent of the invention may be directly or indirectly conjugated with one or more enzyme moieties, (the term "moiety" in the present content means a part of molecule of the enzyme that is capable of oxidoreductase activity, it includes both entire or substantially entire enzyme molecule and portions of said molecule that are capable of oxidoreductase enzymatic activity). Molecules of both or either first and/or second binging agents may be conjugated with one or several functionally active moieties of an oxidoreductase. In one embodiment at least one molecule of a first binding agent may be conjugated with one or more enzymatic moieties capable of oxidoreductase activity; in another embodiment at least one molecule of a second binding agent may be conjugated with one or more such moieties. Molecules of third and further binding agents may also be conjugated with an oxidoreductase. The term "directly conjugated" means that an enzyme moiety is linked to a molecule of a binding agent via a chemical bond. The term "indirectly conjugated" means that a moiety of an enzyme is linked to the molecule of a binding agent via a linking molecule, which has one chemical bond with binding agent and another chemical bond with the enzyme. Methods of conjugating biological molecules and linker molecules are well-known in the art and exemplified below.

In one embodiment the moiety of oxidoreductase is a moiety of HRP, e.g. the whole HRP molecule a fragment thereof that is capable of the HRP enzymatic activity, it may also be a recombinant protein comprising the part of HRP that possesses the enzymatic activity, etc. In another embodiment the moiety of oxidoreductase may be a moiety of soybean peroxidase (SP). In another embodiment the moiety of oxidoreductase may be a moiety of laccase.

Non-limiting examples of binding agents which comprise an enzyme with oxidoreductase activity may be antibody molecules or derivatives thereof, e.g. a Fab, conjugated with one or more moieties of HRP, and nucleic acid binding agents conjugated with HRP. Such binding agents may bind directly or indirectly to single target units, e.g. single target molecules, and form thereby complexes, wherein a single such complex comprises a single individual unit of the target and one or more of binding agents wherein one or more of the binding agents comprise an enzyme with oxidoreductase activity.

In one embodiment the binding agent is a conjugate comprising one, or two or more moieties of a peroxidase wherein said moieties are directly linked to the binding agent, e.g. an antibody molecule directly conjugated with one or more moieties of HRP. In another embodiment the binding agent may be a conjugate that comprises two or more enzymes with peroxidase activity, e.g. two or more moieties of HRP, that are linked to the binding agent indirectly, e.g. a conjugate wherein one or more molecules of an antibody and one or more HRP moieties independently linked to a backbone polymer, i.e. the enzyme with peroxidase activity is indirectly linked to the binding agent, i.e. to the antibody.

The number of HRP per molecule of binding agent may vary, from being 1 enzyme moiety per a binding agent 20-50 per a binding agent or be even higher. In some embodiments it may be preferred to use binding agents wherein the number of HRP moieties is at least two, preferably from two to twenty-twenty five enzyme moieties per binding agent, e.g. between three and twenty, such as 4, 5, 6, 7, 8, 9, 10 etc. It has surprisingly been found that, using binding agents, wherein the number of the enzyme moieties per binding agent is more than one, preferably more than two per binding agent, preferably more than tree per binding agent. In some embodiments it may be preferred to use binding agents comprising more than four enzyme moieties per binding agent per binding agent, preferably between 5 and 20, for example from 5 to 15. Binding agents with more than four enzyme moieties are favorable for formation of target sites which can be visualized as substantially identical in size dots. In some embodiments, it may be even preferred that each binding agent molecule comprising the enzyme of a pool of such binding molecules comprises approximately the same number of enzyme moieties, e.g. 4-6 per binding agents of a pool, 5-7, 6-8, 7-9, 8-10, etc moieties of enzyme per binding agent molecule, e.g. 5-6 or 6-7 HRP moieties per an antibody molecule, e.g. per primary or per secondary antibody molecule. The latter mentioned binding agent constructs comprising multiple moieties of HRP are exemplary. To achieve the mentioned effect, a binding agent may comprises multiple moieties of any enzymes with oxidoreductase activity of the invention discussed above. The binding agent may also comprise a combination of multiple moieties of different oxidoreductase enzymes.

In some other embodiments, relatively small conjugate molecules of binding agents, e.g. single antibody molecules or isolated Fab regions of antibodies that are conjugated with one, or two, or more moieties of an enzyme, e.g. HRP, may be preferred. Such binding agents are relatively compact molecules and this may be advantageous for detecting individual units of targets that are "hidden" or masked in a target or in a sample, e.g. individual single target molecules may be masked by other molecules of the surroundings, single target structures can be hidden in a target molecule, or single viral particles may be hard to reach in complicated biological samples comprising cells.

In some other embodiments, large conjugates comprising a binding agent and tens to hundreds enzyme moieties may be preferred. Such binding agents may be advantageous e.g. in cases where very fast target detection is concerned or obtaining large deposits per individual target site is desirable.

A single unit of a target bound (directly or indirectly) to a binding agent comprising an enzyme with oxidoreductase activity, e.g. peroxidase activity, constitutes a single target site of the invention.

In one embodiment, a single target site of the invention comprises a single target unit of a target, at least one primary antibody, or a derivative thereof, and at least one secondary antibody, or a derivative thereof, conjugated with one, two or more enzymes with peroxidase activity, e.g. HRP.

In another embodiment, a single target site may comprise a single unit of a target, at least one primary antibody molecule conjugated with a hapten and an antibody against hapten which are conjugated with one, two or more enzymes with peroxidase activity, e.g. HRP.

In another embodiment, a target site may comprise a single unit of a target, one or more first nucleic acid/nucleic acid analog binding agents specific for the target, and one or more second nucleic acid/nucleic acid analog binding agents specific for the first nucleic acid/nucleic acid analog binding agents.

The above embodiments are not limiting. The invention in other embodiments may relate to any combination of a single unit of any target discussed above with any binding agents discussed above making a target site of the invention.

A single target site of the invention in one embodiment may be a single site of a solid support comprising a single unit of a target labeled with enzymatic activity of the invention, i.e. conjugated directly or indirectly with an enzyme with oxidoreductase activity, or a single unit of recombinant fusion molecule comprising a an enzyme with oxidoreductase activity. In one embodiment an oxidoreductase enzyme may the target per se. correspondingly, a target site in this embodiment may comprises just a single unit of an oxidoreductase enzyme, such as an immobilized moiety of an oxidoreductase enzyme, e.g. HRP or laccase which is immobilized on or within a solid support.

Enzyme Substrates

After incubation with one or more binding agents and formation of target sites of the invention described above, a sample comprising one or more single target sites according to the invention is incubated in an aqueous solution (i). An aqueous solution (i) according to the invention comprises a first substrate of an enzyme associated with a single target site of the invention, wherein said first substrate is a water soluble electron rich organic compound which is (1) capable of generating a stable radical upon a reaction with the enzyme; and (2) capable of cross-linking molecules of a second substrate of said enzyme in the presence of both the enzyme and a peroxide compound, thereby producing a water insoluble polymeric product of said second substrate. An aqueous solution (i) according to the invention also comprises a second substrate of an enzyme associated with a single target site of the invention, wherein said second substrate is a conjugate molecule comprising at least two compounds that are capable of serving as substrates of said enzyme and a detectable label, wherein the detectable label is selected from the group consisting of a fluorescent, luminescent, radioactive or chromogenic matter or a member of a specific binding pair.

First Substrate

A first substrate of an enzyme associated with a single target site of the invention (also termed hereafter as "first substrate") is a substrate of an enzyme with oxidoreductase activity. This substrate (1) is a water soluble electron rich organic compound, (2) is capable of generating a radical upon a reaction with said enzyme, and (3) is capable of cross-linking water soluble molecules of a second substrate of said enzyme (in the presence of said enzyme and a peroxide compound) producing thereby a water insoluble polymeric product of said second substrate.

By the term "water soluble" is meant that molecules of the first substrate are soluble in water and water containing solutions. By the term "electron rich compound" is in the present content means an organic compound that comprises a conjugated system of connected p-orbitals including compounds with alternating single and multiple bonds. Lone pairs and radicals may be part of the system. The compound may be cylic, acyclic or both. By "conjugated" is meant that there is an overlap of one p-orbital with another across an intervening sigma bond (in larger atoms d-orbitals can be involved). A conjugated system has a region of overlapping p-orbitals, bridging the interjacent single bonds. They allow a delocalization of pi electrons across all the adjacent aligned p-orbitals, which in general may lower the overall energy of the molecule and increase stability. The pi electrons of a conjugated system do not belong to a single bond or atom, but rather to a group of atoms.

The group of enzymes with oxidoreductase activity of the invention includes diverse enzymes that can utilize a great number of substrates. Among these substrates, the substrates of the invention are those compounds that are water soluble organic electron-rich organic compounds comprising a conjugated pi-system, which are capable of generating radicals, preferably stable radicals, upon a reaction with an enzyme with oxidoreductase activity of the invention. The term "stable radical" in the present context means that under conditions of the present invention, e.g. in an aqueous solution (A) (described below), a radical of the first substrate has a life time of at least 20 seconds, preferably from about 1 minute to about 15 minutes, or longer e.g. 2, 3, 4, or 5 minutes, between 5 and 10 minutes, etc. Further, radicals of compounds that make up the group of the first substrates of the invention are capable of cross-linking water soluble molecules of the second substrate of the invention and thereby converting said water soluble molecules into a water insoluble polymeric product.

In particular, in one embodiment the invention relates to the first substrate which is represented a group of a water soluble organic electron-rich compounds that comprise a group of interconnected carbon atoms, wherein every second bond is a double bond, preferably compounds that comprise a chain of at least three (C—C═) repeats, or compounds comprising an aromatic ring structure.

In one embodiment, the first substrate may be represented by a compound comprising a structure of formula (I):

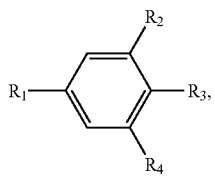

wherein
R1 is an aryl or vinyl,
R2, R3 and R4 is independently H, N—(X)$_2$, O—(X)$_2$, wherein X is an alkyl, vinyl or aryl, or H, and wherein R2, R3 and R4 are not simultaneously H,
wherein.
N is nitrogen,
H is hydrogen;
O is oxygen.
wherein Non-limiting examples of compounds of above formula that have capacity as the first substrate of an enzyme with oxidoreductase activity of the invention may be 3'3'-diaminobenzidine, ferulic acid, hydroxycinnamic acid and derivatives thereof.

In one preferred embodiment the invention relates to 3'3'-diaminobenzidine (DAB) as the first substrate.

The present invention utilizes the capacity of DAB to form a stable radical which can cross-link molecules of the second substrate in the presence of an enzyme with oxidoreductase activity, i.e. horse radish peroxidase (HRP), and a peroxide compound, i.e. hydrogen peroxide, and deposit the cross-linked molecules of the second substrate discretely at single target sites.

In another preferred embodiment, the invention relates to ferulic acid as the first substrate.

Ferulic acid is capable of cross-linking molecules of second substrates of the invention in the presence of an enzyme with oxidoreductase activity, i.e. horse radish peroxidase (HRP), and a peroxide compound, i.e. hydrogen peroxide, and deposit said second substrate discretely at single target sites of the invention. Ferulic acid as the first substrate is particular useful in embodiments where larger deposits of the second substrate at target sites are desirable, e.g. dots of more than 2 micrometer in diameter.

In some other preferred embodiments the invention may relate to derivatives of 3'3'-diaminobenzidine or ferulic acid. The term "derivative" means in the present content a compound that is derived from 3'3'-diaminobenzidine, ferulic acid or a compound that can be imagined to arise from 3'3'-diaminobenzidine, ferulic acid, if one atom in the latter molecules is replaced with another atom or group of atoms. The invention relates to derivatives of 3'3'-diaminobenzidine and ferulic acid that meet the requirements for the first substrate of the invention discussed above, e.g alpha-cyano-4-hydroxy-cinnamic acid as derivative of ferulic acid.

In another preferred embodiment, the invention relates to 4-hydroxy-cinnamic acid and derivatives thereof as the first substrate, e.g. alpha-cyano-4-hydroxycinnamic acid. Alpha-cyano-4-hydroxycinnamic acid as the first substrate is in particular useful in embodiments when small and compact deposits of the second substrate are desirable, e.g. dots around 2 micrometers and smaller.

For the purposes of the present invention, i.e. to produce deposits of the second substrate under conditions of the invention that are larger than 0.4 micrometer in diameter, such around 1 micrometer, 1.5 micrometers, 2 micrometer, 3 micrometer or 4 micrometer, the amount of a first substrate in the aqueous media (A) and/or aqueous media (B) may vary from around 0.05 mM to around 15 mM, depending on the structure of the compound representing the first substrate.

For example, the amount of a ferulic acid or a derivative thereof as the first substrate in the aqueous media (A) may vary between 0.5 mM and 5 mM, such as for example, around 0.5 mM, around 1 mM, around 1.5 mM, around 2 mM, around 2.5 mM, around 3 mM. The term "around" means a deviation of 1-25% from the indicated value.

Derivatives of hydroxycinnamic acid, such as Alpha-cyano-4-hydroxycinnamic acid, as the first substrate are preferably used in the range from about 1.5 mM to about 15 mM, e.g around 1.5 mM, around 1.75 mM, around 2 mM, around 2.5 mM, around 3 mM, between 3 mM and 4 mM, between 4 mM and 5 mM, between 5 mM and 6 mM, between 6 mM and 7 mM, between 7 and 8 mM, between 8 mM and 9 mM, between 9 and 10 mM, between 10 mM and 11 mM, between 11 mM and 12 mM, between 12 mM and 13 mM, between 13 mM and 14 mM, between 14 mM and 15 mM (including both end points of all mentioned intervals and all values within).

When DAB is used as the first substrate, its amount in an aqueous solution (A) is preferably less than 1 mM, preferably within the range of 0.05 mM to 1 mM, such as between 0.05 mM and 0.08 mM, e.g. around 0.07 mM, i.e. from 0.066 mM to 0.074 mM, or between 0.08 mM to 0.1. mM, e.g. around 0.09 mM, or between 0.1. mM and 0.3 mM, e.g. around 0.15 mM, around 0.2 mM, around 0.25 mM, or between 0.3 mM and 0.6 mM, e.g. around 0.35 mM, around 0.4 mM, around 0.45 mM, around 0.5 mM, around 0.55 mM, or between 0.6 mM and 1 mM, e.g. around 0.7 mM, around 0.75 mM, around 0.8 mM, between 0.8 mM and 1 mM.

Second Substrate

According to the invention the second substrate of an enzyme of the invention (also termed herein as "second substrate") is a conjugate molecule comprising at least two compounds that are capable of serving as substrates of said enzyme and a detectable label, wherein the detectable label is selected from the group consisting of a fluorescent, luminescent, radioactive or chromogenic matter or a member of a specific binding pair.

In some preferred embodiments the invention relates to a large group of conjugate molecules as second substrates that share the following features:
1. The conjugate molecules are water soluble molecules comprising two or more substances that can serve as substrates of the enzyme of the invention, preferably as substrates of HRP, and one or more labels wherein the substrates and labels are linked together via a water soluble linker compound (termed hereafter "linker");
2. The enzyme substrate moieties are "concentrated" in the conjugate molecule in one part of said molecule and the labels are "concentrated in another part of said molecule, wherein the label(s) are distanced away from the substrates by approximately 30 consecutively interconnected atoms or more, i.e. separated approximately by 2.5 nm or more, preferably by more than 3 nm
3. The enzyme substrates are separated from each other by a distance that is less than 2.5 nm, e.g. separated within molecule of the conjugate by less than 30 interconnected carbon or heretoatoms, such as carbon, nitrogen, sulphur and/or oxygen atoms or less, preferably not more than 5-20 atoms;
4. The linker is a compound which comprises at least 30 consecutively connected atoms;
5. The conjugates do not precipitate from an aqueous solution (ii) containing a peroxide compound and a first substrate of the invention in the absence in the environment of an enzyme with oxidoreductase activity.
6. The conjugates do not precipitate from an aqueous solution (ii) containing a peroxide compound in the presence of an enzyme with oxidoreductase activity and in the absence the first substrate of said enzyme in the environment.
7. The conjugates precipitate from an aqueous solution (ii) containing a peroxide compound and the first substrate of an enzyme with oxidoreductase activity of the invention in the presence of said enzyme in the environment.

Deposits of the second substrate may be directly detectable by visual means because they, in some embodiments, may comprise a chomogenic, fluorescent or luminescent label. In other embodiments the precipitated second substrate may be "stained" in steps following the deposition to be visible. In both cases, the deposits of the second substrate will "report" to the observer the presence a single target site of the invention in the surroundings. The molecules of second substrate of the invention are thus interchangeably termed herein "reporter" molecules.

Non-limiting embodiments of second substrate molecules suitable for the purposed of the present invention are described in detail below and in EXAMPLES.

In one embodiment the invention relates to a second substrate which is a water soluble conjugate molecule that comprises
(i) one or more detectable substances (termed interchangeably "label")
(ii) at least two substances, which are capable of serving as substrates of the enzyme of the invention, and
(iii) a linker
wherein
said linker is a compound comprising at least one linear chain consisting of at least 30 consecutively connected atoms that contains at least two branching points, wherein said brunching points are separated by a molecular distance of at least 30 consecutively connected atoms;
wherein
the labels (i) and oxidoreductase substrate moieties (ii) are attached to the linker at its two branching points that are separated by a distance of at least 30 consecutively connected atoms, and
wherein
any two neighboring enzyme substrates are separated from each other by a molecular distance that is less than 30 consecutively interconnected atoms The term "detectable substance" means that the substance can give off a detectable chromogenic, fluorescent, luminescent or radioactive signal be detected by visual means, or it can be detected using its specific binding partner, e.g. an antibody, nucleic acid sequence, nucleic sequence analog sequence, hapten, antigen, receptor, receptor ligand, enzyme, etc.

In some embodiments a water soluble conjugate molecule of the invention may additionally comprise moieties that may enhance its features, e.g. improve its capacity as the label or enzyme substrate, or increase/reduce its water solubility.

In one embodiment, conjugate molecules of the invention may be selected from a group of compounds of formula (II):

(Y)$n$-L-(Z)$m$, wherein
Y is a moiety capable of serving as substrate of an enzyme with oxidoreductase activity;
Z is a detectable label;
L is a linker compound
wherein
n is an integer from 2 to 150, and
m is an integer from 1 to 150

In one preferred embodiment Y is selected from compounds of the following formula (II):

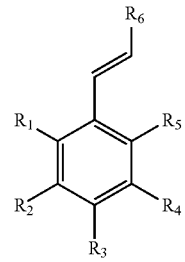

wherein
R1 is —H, —O—X, N(X)$_2$ or —S—X;
R2 is —H, —O—X, —N(X)$_2$, or —S—X,
R3 is —H, —OH, —NH$_2$ or —SH;
R4 is —H, —O—X, —N(X)$_2$, or —S—X,
R5 is —H, —O—X, N(X)$_2$, or —S—X,
R6 is —CON(X)$_2$, or CO—X,
wherein
H is hydrogen;
O is oxygen
S is sulphur
N is nitrogen, and
X is H, alkyl or aryl.

In one embodiment at least one of the compounds that are capable of serving as substrate of an enzyme with oxidoreductase activity is a compound of formula (II).

In one embodiment at least two of the compounds that are capable of serving as substrate of an enzyme with oxidoreductase activity in the conjugate molecule are compound of formula (II).

In one embodiment at least two of the compounds that are capable of serving as substrate of an enzyme with oxidoreductase activity in the conjugate molecule are identical compounds of formula (II).

In one embodiment at least two of the compounds that are capable of serving as substrate of an enzyme with oxidoreductase activity in the conjugate molecule are different compounds of formula (ii).

In one embodiment all compounds that are capable of serving as substrate of an enzyme with oxidoreductase activity in the conjugate molecule are defined by formula (II). In one embodiment these are identical compounds, in another embodiment the conjugate molecule comprises any combination of different compounds defined by formula (II).

In one preferred embodiment Y may be a residue of cinnamic acid; in another preferred embodiment Y may be a residue of ferulic acid. In another preferred embodiment Y may be a residue of caffeic acid; in another preferred embodiment Y may be a residue of amino cinnamic acid. In another preferred embodiment Y may be a residue of sinapinic acid. In another preferred embodiment, Y may be a derivative of ferulic acid, cinnamic acid, caffeic acid, amino cinnamic acid or sinappinic acid.

Preferably a residue Y defined by the formula (II) is connected to a linker L via group R6.

In one preferred embodiment the conjugate comprises two to four identical residues Y. In another preferred embodiment the conjugate comprises a combination of two to four different residues Y. In one preferred embodiment the two to four residues Y are compounds defined the formula (II).

In one preferred embodiment, the conjugate may comprise two to four residues ferulic acid or residues of derivatives thereof, in another embodiment the conjugate may comprise two to four residues cinnamic acid or residues of derivatives thereof; in another embodiment the conjugate may comprise two to four residues of caffeic acid or residues of derivatives thereof; in another embodiment the conjugate may comprise two to four residues amino cinnamic acid; in another embodiment the conjugate may comprise two to four residues sinapinic acid or residues of derivatives thereof. The two to four derivatives of the latter compounds may be the same compound or may be different compounds.

In one preferred embodiment a conjugate molecule may comprise two Y compounds of formula (II), or two derivatives thereof, e.g. two ferulic acid residues, or two cinnamic acid residues, or two amino cinnamic acid residues, or two caffeic acid residues, or two sinapinic acid residues, etc. and one or more detectable labels; in another embodiment the conjugate may comprise three molecules of formula (II) or three derivatives thereof, such as three ferulic acid, cinnamic acid, caffeic acid, amino cinnamic acid, sinapinic acid, etc., and one or more detectable label; in another embodiment the conjugate may comprise four compounds of formula (II) or four derivatives thereof, e.g. four ferulic acid, cinnamic acid, caffeic acid, amino cinnamic acid, sinapinic acid, or four derivatives the latter, and one or more detectable labels.

In some embodiments the number of Y compounds may be higher than 4, e.g. such as 5-10, 10-15, 15-20, 20-50, 50-100, or 100-150 compounds. Non-limiting examples of such conjugate molecules are described in Examples. In some preferred embodiments such conjugates may comprise more than one linear chain of at least 30 consecutively connected atoms, e.g. 30-150 atoms, wherein two to four Y compounds are attached to each linear chain at first and the same branching point of the chain, and several of such linear chains are linked to another water soluble linker molecule, e.g. a dextran, via a second (another) branching point of said linear chains.

In one preferred embodiment, a conjugate molecule may comprise a combination of two or four different compounds of formula (II), or a combination of two or four derivatives thereof, e.g. two ferulic acid residues and one cinnamic acid residue, two sinapinic acid residues and two caffeic acid residues, etc.

In one preferred embodiment Y may be a residue of amino acid tyrosine or residue of a derivative thereof. A conjugate may comprise 2 to 4 or more such residues.

In one embodiment conjugate molecule may comprise a combination of substrates of the enzyme with oxidoreductase activity, wherein at least one of said substrates is tyrosine. In one embodiment the conjugate molecule comprises at least one tyrosine residue and at least one compound of formula (II), or a derivative thereof, and at least one another is a compound of formula (II) a derivative thereof, e.g. one tyrosine residues and two residues of sinapinic acid or derivatives thereof.

In some embodiments it may be preferred that the conjugate comprises 4 to 6 residues Y, wherein Y is represented by any compound or a combination of any compounds as described above.

According to the invention, Y compounds are located in a conjugate molecule as a group, preferably grouped as two to four Y compounds per group, (i.e. a conjugate comprising more than four Y compounds may comprise several groups of two to four Y compounds, wherein said groups are separated in the conjugate molecule by a group of atoms, e.g. by a molecular distance corresponding to 30 connected atoms or more). Preferably, the two to four Y compounds in such groups are linked together via a spacer compound that provides a distance between two neighboring Y residues which is not longer than 5-15 interconnected atoms, e.g. 5-10, 6-12, 7-13, 8-14, 9-15, etc., For example, 2-4 Y compounds may be attached to amino acids making up a peptide chain comprising 2 to 4 amino acid residues, e.g. residues of lysine, serine, cystein, etc., wherein the Y compounds are attached to reactive groups of the amino acid residues of the peptide, e.g. to the epsilon amino groups of lysine residues. Two to four compounds Y may also be connected to each other via other short polymers which comprise a number of brunching points, wherein a molecular distance between these branching points corresponds to a chain of not more than 3-7 atoms, preferably 3-5 atoms, wherein the Y compounds may be directly indirectly linked to said branching points. Two to four compounds Y may also be grouped together being conjugated to a non-polimeric molecule that have two to four reactive groups allowing attaching any two to four Y compounds. Such grouped location of Y compound is termed thereafter "Y-head" of the conjugate molecule.

In one preferred embodiment, the Y-head comprises two to four Y-residues linked via a short polymer, e.g. a short PNA molecule or a short peptide, wherein the peptide, preferably, comprises lysine, serine glutamate and/or cystein residues. However, any other polymeric or non-polimeric water soluble molecules that comprise 15 or less atoms that can be conjugated with at least two Y-residues and a linker L may be suitable.

In one embodiment one Y-head comprising two to four compounds Y may be linked to a polymer comprising two or more repeats of the following formula (III)

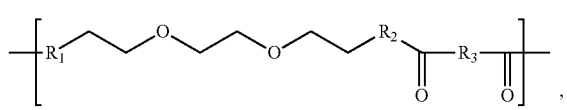

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups. The resulting conjugate may be further conjugated with one (or more) detectable label, or it may be conjugated with another water soluble molecule which comprises one or more reactive groups allowing attaching one or several such conjugates. One non-limiting example of such water soluble molecule may be a dextran polymer.

Close spacing of Y compounds in conjugate molecules has influence on functional capacity of the conjugates as second substrates of the invention, namely the conjugates remain soluble in aqueous solutions containing a peroxide compound and the first substrate of an enzyme with oxidoreductase activity (as described above), in the absence of the enzyme in the environment, but rapidly and efficiently precipitates from such solutions when an enzyme with oxidoreductase activity presents in the environment (compared to conjugates that comprise only one Y compound or comprise several Y compounds that are not "concentrated" in the conjugate molecule in form of an Y-head, i.e. molecular space between two neighboring Y residues is larger than the discussed above distance. Such compounds are not efficient to form discrete deposits at single target sites of the invention).

The detectable label of a conjugate molecule may be any substance which can be visually detected, e.g. a fluorescent or luminescent substance, or any substance that can be detected by using some detecting means, e.g. a radioactive label, a member of a specific binding pair, e.g. a nucleic acid sequence, hapten, etc.

Any fluorescent, luminescent, bioluminescent or radioactive molecules may be used as the labels. Many of them are commercially available, for example fluorescent stains Alexa Fluors (Molecular Probes) and DyLight Fluors (Thermo Fisher Scientific). Other non-limited examples of fluorescent labels may be the following molecules: 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, Cy2, Cy3, Cy5, AMCA, PerCP, R-phycoerythrin (RPE) allophycoerythrin (APC), Texas Red, Princeton Red, Green fluorescent protein (GFP) coated CdSe nanocrystallites, ruthenium derivatives, luminol, isoluminol, acridinium esters, 1,2-dioxetanes and pyridopyridazines, radioactive isotopes of hydrogen, carbon, sulfur, iodide, cobalt, selenium, tritium, or phosphor.

In some embodiments the detectable label may be an enzyme. Non-limiting examples of suitable enzyme labels may be alkaline phosphatase (AP), beta-galactosidase (GAL), glucose-6-phosphate dehydrogenase, beta-N-acetyl-glucosaminidase, β-glucuronidase, invertase, xanthine oxidase, firefly luciferase, glucose oxidase (GO).

In other embodiments, the detectable label may be a member of a specific binding pair, e.g. a hapten. As non-limiting examples of suitable haptens may be mentioned 2,4-dinitrophenol (DNP), digoxiginin, fluorescein, Texas Red, tetra methyl rhodamine, nitrotyrosine, acetylamino-flurene, mercury trintrophonol, estradiol, bromodeoxy uridine, dimethylaminonaphthalene sulfonate (dansyl), amino acids tyrosine, serine, etc. As examples of suitable specific binding pairs may also be mentioned biotin, streptavidin, complementary natural and non-natural oligonucleotide sequences, zinc fingers binding domain pairs, etc. Other examples are discussed above.

In one preferred embodiment the label is a hapten. In another preferred embodiment, the label is a fluorescent substance. In another preferred embodiment, the label is a member of a specific binding pair. Other labels may be preferred in other embodiments.

The number or detectable labels per conjugate molecule (as any of the described above) may vary. In some embodiments the number of labels may be from 1 to 3, for example 1, 2 or 3 labels per conjugate molecules. In some other embodiments, the conjugate may comprise more from 4 to 150 labels per conjugate molecule.

In one preferred embodiment a conjugate (as any of the described above) comprises one detectable label. In one preferred embodiment a conjugate molecule may comprise one Y-head (as any of the discussed above) and one label.

According to the invention, in a conjugate molecule the detectable substance (a single label or a plurality thereof) is separated from the compounds that are substrates of an enzyme with oxidoreductase activity, e.g. from an Y-head, by a molecular distance of more than 2.5 nm, e.g. separated by a chain of at least 30 consecutive atoms, e.g. 30-150 or more consecutive atoms. In embodiments where the conjugate comprises one chain of connected atoms as L linker between an Y-head and 1 (or more) labels, the Y-head and the label(s) are linked to said chain at branching points located at least 30 atoms apart from each other, e.g. on the opposite ends of a chain of 30 connected atoms.

In some embodiments, when a conjugate comprises more than 1 label, it is preferred that the labels are grouped so that there is a molecular distance between the labels, that correspond to a chain of at least 30 consecutively connected atoms (termed "spacer"), preferably 60 consecutively atoms or more, e.g. 90 consecutively interconnected atoms. It is preferred that the spacer between the labels is a hydrophilic compound. The latter group of labels is then attached to a linker compound linking said labels and enzyme substrate moieties in a conjugate molecule in the way described above, i.e. a label of the group that is positioned closest to the Y-head is distanced away from any of the enzyme substrates of the Y-head by at least 30 interconnected atoms, i.e. by at least 2.5 nm distance. Such arrangement of multiple labels in a conjugate molecule is termed thereafter "Z-tail".

Preferably, a spacer of at least 30 consecutive atoms between labels of a Z-tail is a polymeric compound comprising two or more repeats of the following formula (III)

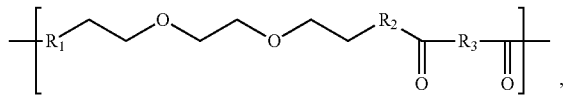

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups.

Multiple labels attached to and separated by the above spacer may be conjugated with one Y-head or several Y-heads via any suitable linker, e.g. water soluble polymers allowing multiple attachments, e.g. dextran. In some embodiments several Y-heads may be conjugated with several Z-tails via such polymer.

In one embodiment multiple labels of a conjugate molecule of the invention may be same detectable substances, in another embodiment the labels may be different detectable substances.

The Z-tail arrangement of labels has advantages in that (1) conjugates comprising multiple hydrophobic labels remain good solubility in water solutions, and (2) the labels are better accessible for binding agents, when binding agents are used to detect the deposited conjugates.

The linker between the oxidoreductase substrates and labels (e.g. between Y head and Z tail), L, is according to the invention a molecule that comprises a chain of at least 30 contiguous atoms, such as 30-150 atoms or more, e.g. 30, 45, 60, 90, 150, 300, 500 atoms or more. In one preferred embodiment preferably, L comprises 150 contiguous atoms. In some embodiments, a linker molecule comprises a linear chain of atoms wherein every two connected carbon atoms are followed by an atom of oxygen or nitrogen.

In one preferred embodiment L may be a single linear polymer molecule; in another preferred embodiment L may be a conjugate molecule which may comprise several different polymers conjugated together.

In one preferred embodiment L is a linear polymer that comprises a chain of atoms wherein two consecutive carbon atoms are followed by a heteroatom selected from oxygen or nitrogen, e.g. such as a linker comprising described below, or polyethylene glycol, etc.

In another preferred embodiment the linker is a compound comprising two or more repeats of the following formula (III)

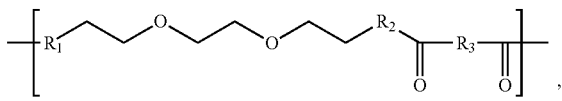

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups.

Preferably, L comprises at least two repeats of the above formula wherein both R1 and $R_2$ are NH and $R_3$ is $CH_2OCH_2$. Preferably, L comprises one or more repeats of the following formula (IV)

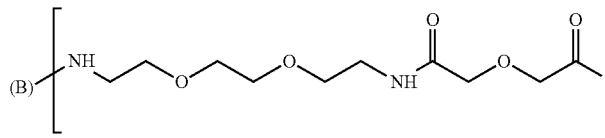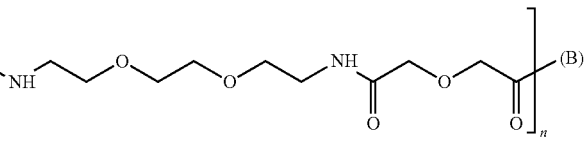

wherein n is an integer from 1 to 10, and (B) is a branching point. The L molecules of this formula and their synthesis are in detail described in WO2007/015168, which is incorporated herein by reference.

By the term "branching point" is meant a point in a polymer molecule wherein a branch, e.g. a side chain of the same polymer, or other molecules may be attached. The branching point may be an atom, a group of atoms, or a functional group via which compounds Y and Z may be directly or indirectly conjugated to L.

There is a great variety of polymer molecules that may be used as linker L. Examples include polysaccharides such as dextrans, carboxy methyl dextran, dextran polyaldehyde, carboxymethyl dextran lactone, and cyclodextrins; pullulans, schizophyllan, scleroglucan, xanthan, gellan, O-ethylamino guaran, chitins and chitosans such as 6-O-carboxymethyl chitin and N-carboxymethyl chitosan; derivatized cellolosics such as carboxymethyl cellulose, carboxymethyl hydroxyethyl cellulose, hydroxyethyl cellulose, 6-amino-6-deoxy cellulose and O-ethylamine cellulose; hydroxylated starch, hydroxypropyl starch, hydroxyethyl starch, carrageenans, alginates, and agarose; synthetic polysaccharides such as ficoll and carboxymethylated ficoll; vinyl polymers including poly(acrylic acid), poly(acryl amides), poly (acrylic esters), poly(2-hydroxy ethyl methacrylate), poly (methyl methacrylate), poly(maleic acid), poly(maleic anhydride), poly(acrylamide), poly(ethyl-co-vinyl acetate), poly (methacrylic acid), poly(vinylalcohol), poly(vinyl alcohol-co-vinyl chloroacetate), aminated poly(vinyl alcohol), and co block polymers thereof; poly ethylene glycol (PEG) or polypropylene glycol or poly(ethylene oxide-co-propylene oxides) containing polymer backbones including linear, comb-shaped or hyperbranched polymers and dendrimers, including branched PAMAM-dendrimers; poly amino acids including polylysines, polyglutamic acid, polyurethanes, poly(ethylene imines), pluriol; proteins including albumins, immunoglobulins, and virus-like proteins (VLP), and polynucleotides, DNA, PNA, LNA, oligonucleotides and oligonucleotide dendrimer constructs; mixed polymers, i.e., polymers comprised of one or more of the preceding examples of polymers, co-block polymers and random co-polymers.

Properties of the chosen polymer can be modified to optimize performance, e.g. the length or branching can be optimized. Furthermore, the polymer may be chemically modified to carry various substituents. The substituents may be further chemically protected and/or activated, allowing the polymer to be derivatized further.

In one preferred embodiment the linker compound between oxidoreductase substrates and labels is a dextran polymer or a conjugate molecule comprising a dextran polymer.

Methods of conjugating polymers with different chemical substances, e.g. labels, are well known in the art and can be used to make conjugates of the invention. For example, the polymer may be activated with vinylsulfon and mixed with a detectable label and a molecule of formula (II) to form the polymer conjugate. In other embodiments, aldehydes can used to activate a polymer, e.g. dextran, which is then mixed with a detectable label and a molecule of formula (II). Yet another method of preparing polymeric conjugates is by using so called chemo selective coupling schemes for coupling the components together, e.g. molecules can be derivatized with thiol reactive maleimide groups before being covalent coupled to an thiol modified polymeric backbone. In some other embodiments, a molecule for formula (I) and a detectable label can be attached to the polymer via a linking compound. Examples of this method include the use of homobifunctional linker compounds such as glutaric dialdehyde, hexan di isocyanate, dimethylapimidate, 1,5-difluoro-2,4-dinitrobenzene, heterobifunctional cross binders like e.g. N-gamma-maleimidobytyroloxy succinimide ester, and zero length cross binders such as 1-ethyl-3-(3-dimethylaminopropyl)cabodiimide.

Methods of derivatization of polymers comprising one or more repeats of formula (III) (termed hereafter "L30") are described in detail in WO2007/015168, which is incorporated herein by reference.

Exemplary conjugates comprising linkers that are polymers comprising various number of repeats of formula (III), such as a polymer comprising two L30 repeats, (termed L60), such as a polymer comprising three L30 repeats (termed L90), such as a polymer comprising five L30 repeats (termed L150) are described in EXAMPLES.

The amount of the second substrate in the aqueous media (ii) may vary from about $10^{-10}$ M to about $10^{-4}$ M, for example, in case a conjugate (as any of the described above) comprises a radioactive label, the applicable amount may be from about $10^{-10}$ M to about $10^{-6}$ M, and from about $10^{-9}$ M to about $10^{-4}$ M, in case a conjugate comprises a fluorescent label or a label which is a member of a specific binding pair.

Incubation Media

In one embodiment a sample comprising single units of a target is incubated during a visualization procedure according to the invention in different aqueous media (collectively termed herein "incubation media").

The term "incubation media" means in the present context an aqueous solution where the sample is maintained during a certain period of time (termed herein "incubation time") in order to achieve results of a desirable reaction.

Time for maintaining/incubating the sample in an incubation medium, i.e. incubating time, may vary depending on the technical effect which is desired to be achieved following the incubation. In different embodiments an incubation may lasts from approximately 3 seconds to approximately 3 min, e.g. around 10 seconds, 20 seconds, 30 seconds, 1 minute, 2 minutes, 5 minutes, 10 minutes, or longer, e.g. one-two hours, overnight. In one embodiment, incubating time at all steps of the method may have the same duration, i.e. every incubating may lasts 5 to 10 minutes, etc. In another sample in an aqueous solution comprising a binding agent (termed hereafter "binding agent solution/media" or "BAM") may lasts 1-3 minutes, incubating in an aqueous media (i) and/or aqueous solution (ii) media may lasts 10 minutes.

Incubating may be performed at various temperatures, depending on the type of target, binding agent, etc. The procedures according to the invention are substantially temperature independent and can be performed at a temperature from around +4 C.° to around +40 C.°, however, if desired, the temperature may be used for extending or reducing duration of an incubation, e.g. lower temperatures may be used to prolong the incubating time, and, vice versa, higher temperatures may be used to shorten the time for incubating.

Non-limiting embodiments of compositions of incubation media are discussed below.

Binding Agent Media

On step (a) of the methods of the invention a sample is incubated with one or more binding agents (such as described above). Accordingly, in one embodiment, the invention relates to an aqueous solution comprising a binding agent, such as e.g. a binding agent comprising an enzyme with oxidoreductase activity. This medium is termed herein "binding agent medium".

One desired technical effect to be achieved due to incubation of the sample in such media is to form target sites according to the invention. Accordingly, the binding agent medium is an aqueous medium, in which the chosen binding agent is soluble and is capable of binding to a single target unit. Basically, the binding agent medium is a buffered aqueous solution of one or more binding agents that has pH in the range from 4 to 9. In some embodiments the binding agent medium may comprise an organic or inorganic salt. The inorganic salt may be selected form e.g. sodium chloride, magnesium chloride, potassium chloride, calcium chloride, sodium phosphate, or ammonium sulfate. The organic salt may be selected from e.g. sodium acetate, ammonium acetate or imidazole salts, e.g. imidazole hydrochloride, etc.

The amount of salt in binding agent media may range from approximately $10^{-3}$ M to saturation, e.g. from approximately 20 mM to approximately 200 mM, or from approximately 50 mM to approximately 500 mM. In one preferred embodiment, the media may comprise salt in the amount from approximately 10 mM to 500 mM. In another preferred embodiment the medium may be free of salt.

As mentioned, typically, the pH value of binding agent media may vary from about 4 to about 9, such as between pH 3.5 and pH 9.5, e.g. between pH 5 and pH 7, between pH 5.5 and pH 6.5 or between pH 6.5 and 7.5, or between pH 7 and pH 8, or between pH 7.5 and pH 8.5, or pH 8 and pH 9. Any buffer with a suitable buffer capacity may be used, e.g. phosphate buffered saline (PBS) and imidazole buffer. Other suitable buffers may be found in Good, Nebr., et al (1966) Hydrogen ion buffers for biological research. Biochem. 5(2), 467-477. The pH value of the media may be essential for binding of binding agent to the target; it may be optimized depending on the nature of the binding agent and the target.

In some embodiments binding agent media may comprise an organic modifier (by the term "organic modifier" is meant any non water solvent), e.g. N-Methyl pyrolidone (NMP), dimethylsulphoxide (DMSO), mono- and diethylene glycol, sulpholane, N,N-dimethylformamide (DMF), polyethylene glycol (PEG), propylene glycol, etc. The amount of the organic modifier may vary from around 1% to around 20% (v/v or w/v), or, in some embodiments, be higher than 20%.

In some embodiments binding agent media may comprise a detergent, e.g. polyethylenglycol-p-isooctyphenyl ether (NP-40)) or a surfactant (e.g. selected from the surfactants based on polyoxyethylene sorbitanmonolaurate (Tween), or a surfactant based on block copolymers (pluronic etc.), etc. The amount of the detergent may vary from about 0.001% to about 5%/v/v or w/v).

In some embodiments binding agent media may comprise a binding agent stabilizing agent, e.g. bovine serum albumin or dextran. The amount of the stabilizing agent may vary from 0.01% to 20% (w/v).

In some embodiments binding agent media may comprise an ion chelator (e.g. ethylene diamine tetra acetic acid (EDTA) or ethylene diamine hydroxyl phenylacetic acid type chelator (EDHPA), etc.). The amount of the chelator may vary from about $10^{-9}$ M to about $10^{-6}$ M.

In some embodiments, binding agent media may comprise one or more blocking agents for saturating non-specific binding sites, i.e. sites of the solid support that do not comprise the target. Some non-limiting examples of blocking agents suitable for different embodiments may be the Denhard's solution, bovine serum albumin, skimmed milk, etc.

As discussed above, the invention contemplates a great variety of species of targets, binding agents and assay formats, accordingly, composition of the binding agent medium may vary and should be adjusted for every particular embodiment using the knowledge of the art. Some non-limited examples of binding agent media are described in EXAMPLES.

Amounts of a binding agent in binding agent media may vary depending on the species of the biding agent, sample, target, composition of the media, etc. For example, in one embodiment, when a sample comprise a target that present in a low concentration range, it may be preferred to use relatively high amounts of binding agents in a binding agent media which composition (e.g. pH, salt concentration, etc) and incubation conditions (e.g. duration of incubation with the sample, temperature) are optimized to facilitate interaction between the binding agents and the target (or other binding partners). Optimization of binding between partners of specific binding pairs is a routine procedure for most of binding agents used for the purposes of the invention, so that a skilled in the art can do it by following guidelines of the art. Such optimization sometimes is necessary to secure binding of a binding agent to the maximal possible number of single units of the target or to another binding agent (e.g. a binding agent bound to the target) in the sample.

In one preferred embodiment, the quantity of a binding agent in the binding media may be adjusted to bind all or a fractional sub-population of single target units present in the sample. In another embodiment, a quantity of binding agent is adjusted to bind all or a fractional sub-population of complexes of single target units with another binding agent of the sample. In one embodiment, the fractional subpopulation corresponds to a majority of single target units of the sample. In another embodiment, the fractional subpopulation corresponds to a minority single target units of the sample. In such embodiments, the composition of binding agent media, e.g. pH, salt content, etc., or incubating conditions, such as temperature, duration etc, may be adjusted so that the affinity of the binding agent to its partner in the sample will be diminished or enhanced and the binding agent will therefore form the binding complexes with a larger or smaller fractional subpopulation of single units of the target present in the sample. In one preferred embodiment, the amount of a binding agent that is capable of specifically binding to its partner in the sample, e.g. a first binding agent, second binding agent and/or amount of binding molecules in a first or second binding agent mixture (see below), is relatively high to saturate all available binding sites in the sample even in conditions that do not favor the partner binding.

The term "fractional subpopulation" in the present context means a portion of the total population of the binding agent partner units in the sample that is equal or less than 99.9%, e.g. equal or less than 99%, 98%, 97% etc, e.g. 75-80%, less than 75%, less than 60%, etc, for example from 1% to 50%, such as from 1% to 25%, etc. In some embodiments the fractional subpopulation may be less than 1% of the total quantity of units of the binding agent partner present in the sample.

In some preferred embodiments, a detectable fractional sub-population of a binding partner of a binging agent in the sample may be predetermined. This may be done by using a mixture of binding molecules of the binding agent, wherein the binding molecules of the mixture are all of the same species and have essentially the same affinity to the (common for all said binding molecules) binding partner in the sample ("essentially" in the present context means that +/−10% difference in the affinity is included), and wherein a portion of said binding molecules is detectably labeled and a portion of said binding molecules is unlabeled, and the both portions are predetermined. The term "labeled binding molecules" means that said binding molecules are associated/linked to a detectable label, e.g. a fluorescent label or enzyme. In one preferred embodiment, the label is an enzyme; in one preferred embodiment the enzyme is an oxidoreductase enzyme, (such as a described above, e.g. HRP). The unlabelled binding molecules do not comprise any detectable label.

In one such embodiment, the binding agent may be a first binding agent that is capable of binding to a single unit of the target and form a complex with said single unit. In another such embodiment, the binding agent may be a second binding agent that has affinity to the first binding agent bound to single target unit in the sample. In some embodiments, the binding agent may be a third binding agent that is capable of binding to the second binding agent, or to a label linked to the second binding agent, or to a reporter deposit at a target site.

Using the binding agent (as any of the mentioned) comprising a predefined ration of labeled and unlabeled binding molecules, it is possible to quantify the amount of a target in the sample precisely by quantifying the target sites (visualized as dots) formed with the labeled binding agent. Methods of quantification of the target in histological samples using mixtures of labeled and unlabelled binding molecules are described in detail in EXAMPLES.

Aqueous Solution (A)

Following the incubation in a binding agent medium, the sample is incubated in an aqueous solution (A) (also termed herein as "reporter deposition media" or "RDM") comprising a first substrate of the enzyme with oxidoreductase activity and, a second substrate of the enzyme with oxidoreductase activity and a peroxide compound.

Optionally, before the incubation in the aqueous solution (A), the sample may be incubated in an aqueous solution (B), which composition is as of an aqueous solution (A) without the second substrate.

Accordingly, in one embodiment the invention relates to incubation media which is in an aqueous solution (A) and in another embodiment the invention relates to incubation media which is an aqueous solution (B).

Both aqueous solution (A) and aqueous solution (B) may be an aqueous buffered solution with a suitable buffer capacity, e.g. phosphate buffered saline (PBS) and imidazole buffer. Other suitable buffers may be found in Good, N E., et al (1966) Hydrogen ion buffers for biological research. Biochem. 5(2), 467-477. The pH value of the solutions may be adjusted in order to achieve the technical effect of the incubation, namely formation of discrete deposits of the second substrate of an enzyme with oxidoreductase activity at discrete single target sites of the invention, for example adjusted to pH ranging from about 4 to about 9. However, pH of the aqueous solutions (A) and (B) is of minor importance for the technical effect of the incubation.

Both aqueous solution (A) and aqueous solution (B) may further comprise an organic or inorganic salt.

The inorganic salt may be selected form e.g. sodium chloride, magnesium chloride, potassium chloride, calcium chloride, sodium phosphate, or ammonium sulfate, etc.

The organic salt may be selected form e.g. sodium acetate, ammonium acetate or imidazole salts, e.g. imidazole hydrochloride, etc.

The amount of salt in an aqueous solution (A) and aqueous solution (B) may range from approximately $10^{-3}$ M to saturation, e.g. from approximately 20 mM to approximately 200 mM, or from approximately 50 mM to approximately 500 mM. In one preferred embodiment, the media may comprise salt in the amount from approximately 10 mM to 500 mM. In another preferred embodiment the medium may be free of salt.

Both aqueous solutions (A) and aqueous solutions (B) may in different embodiments further comprise:
  (i) an organic modifier and/or
  (ii) an enzyme enhancer, and/or
  (iii) an iron chelator, and/or
  (iv) a detergent, and/or
  (v) an anti-microbial agent The organic modifier may be present in the media in the amount from around 1% to around 20% (v/v or w/v), however, in some embodiments higher concentrations of the organic modifier may be required. The organic modifier may for example be polyethylene glycol (PEG). Other examples include but not limited to organic modifiers selected from the group essentially consisting of C1-C4, i.e. lower, alcohols, N-Methyl pyrolidone (NMP), dimethylsulphoxide (DMSO), mono- and diethylene glycol, sulpholane, N,N-dimethylformamide (DMF). In some embodiments it may be advantageous to use polyethylene glycol (PEG), e.g. PEG2000, or propylene glycol. The amount of polyethylene glycol in the media in these cases may vary from about 0.1% (v/v) to about 20% (v/v), for example from about 1% (v/v) to about 15%, such as 5-10% (v/v).

By the term "enzyme enhancer" is meant any compound which enhances the catalytic activity of peroxidase. Such enzyme enhancer may be selected from the group essentially consisting of phenylboronic acid derivatives and divalent metal ions such as nickel or calcium. The amount of the enzyme enhancer may vary from about $10^{-7}$ to about $10^{-3}$ M.

The iron chelator may be ethylene diamine tetra acetic acid (EDTA) or ethylene diamine hydroxyl phenylacetic acid type chelator (EDHPA). Concentration of the iron chelator may vary from about $10^{-9}$ to about $10^{-6}$ M.

The detergent may be selected from polyethylenglycol-p-isooctyphenyl ether (NP-40), a surfactant selected from the surfactants based on polyoxyethylene sorbitanmonolaurate (Tween), or a surfactant based on block copolymers (pluronic etc.). Concentration of the detergent may vary from about 0.001% to about 5%.

Essential components of an aqueous solution (A) are a first substrate of an enzyme with oxidoreductase activity, a second substrate of said enzyme and a peroxide compound.

Embodiments of the first substrate and the second substrates are discussed in detail above.

In one preferred embodiment the first substrate may be 3, 3'-diaminobenzidine (DAB) or a derivative thereof. In another preferred embodiment, the first substrate may be ferulic acid or a derivative thereof.

The amount of the first substrate in an aqueous solution (A) may vary depending on the compound chosen as the first substrate (see discussion above). For example, in embodiments, when DAB is chosen as the first substrate, the amount of DAB in an aqueous solution (A) and in aqueous solution (B) is less than 1.4 mM, preferable less than 1.2 mM, preferably less than 1 mM, such as from around 0.005 mM to around 0.5 mM, for example around 0.3 mM, or around 0.2 mM, such as around 0.15 mM, etc. In embodiments when ferulic acid is used as the first substrate, the amount of said compound is less than 2.5 mM, preferably less than 2 mM, e.g. around 1.5. mM. The term "around" in the present context means +/-0.05-0.5 mM.

Amounts of the other first substrates of the invention in the aqueous solutions (A) or (B) are discussed in the previous sections.

The aqueous solution (i) may comprise various amounts of the second substrate of the enzyme, such as from about $10^{-10}$ M to about $10^{-4}$ M. For example, in embodiments when the second substrate (as any of the described above) comprises a radioactive label, an applicable amount may be in the range from about $10^{-10}$ M to about $10^{-6}$ M. In other embodiments, e.g. when the second substrate comprises a fluorescent label or a label which is a member of a specific binding pair, the amount may be in the range from about $10^{-9}$ M to about $10^{-4}$ M.

In one embodiment, an aqueous solution (A) may comprise a population of identical conjugate molecules of second substrate. In another embodiment, an aqueous solution (i) may comprise a population of different conjugate molecules of second substrate.

A preferred peroxide compound of the invention is hydrogen peroxide, however, other peroxide compounds may also be used in different embodiment, e.g. in some embodiments it may be preferred an organic peroxide such as e.g. tert-butyl peroxide, ditert-butyl peroxide, peracetic acid, etc, or in some embodiments it may be an adduct of hydrogen peroxide, such as hydrogen peroxide urea adduct.

The amount of a peroxide compound in an aqueous solution (i) and an aqueous solution (ii) may not be higher than 5 mM, preferably less than 5 mM, preferably in the range of 0.1 mM to 5 mM, e.g. between 0.1 mM and 1 mM, between 1 mM and 2 mM, between 2 mM and 3 mM, or between 3 mM and 4 mM, preferably in the range between from around 1 mM to around 2 mM, such as around 1.5 mM. The term "around" in the present context means +/-0.05-0.5 mM An aqueous solution (A) comprising a first substrate of enzyme with oxidoreductase activity, a second substrate of said enzyme and a peroxide compound is termed herein "deposition medium".

An aqueous solution (B) may comprise the same compounds in the same amounts as an aqueous solution (A), with the exception that the aqueous solution (ii) does not comprise the second substrate of enzyme with oxidoreductase activity.

In some embodiment a sample comprising single target sites may be initially incubated in an aqueous solution (B) and sequentially in an aqueous media (A).

In another embodiment a sample comprising single target sites is incubated an aqueous solution (A), without preincubation in an aqueous solution (B).

According to the invention the deposition media is a stable solution, i.e. no precipitation of the solved compounds occurs for a relatively long period of times, such as at least 5 hours. To prolong the shelf-life of the media it may be useful to store the media at temperatures below +20° C., e.g. at +4-+10° C., and/or to add to the media an anti-microbial compound. The anti-microbial compound may be any anti-microbial compound commonly used for such purpose, e.g. sodium azid, Proclin™ or Bronidox®.

Detection Media

In one embodiment the invention relates to a method comprising one or more steps following the step (b) which comprise detection of discrete single deposits of the second substrate at single target sites, e.g. a sample comprising discrete deposits of the second substrate may be incubated in incubation media comprising a binding agent capable of specifically binding to a detectable label of the deposited molecules of second substrate.

An incubation medium comprising a binding agent capable of specifically binding to a detectable label of the deposited molecules of second substrate will typically have a similar or the same composition as the binding agent medium discussed above.

The binding agent bound to a detectable label of the deposited second substrate may in one embodiment comprise an enzyme, e.g. horse radish peroxidase (HRP) or alkaline phosphotase (AP). Such binding agent can be detected using a standard visualization system employing chromogenic substrates of the enzymes, e.g. an enzyme substrate solution or a color developing solution. This kind of media may be any suitable media known in the art which is to be selected depending on available means for visualization and following the common general knowledge of the art concerning the nature of the detectable label of the deposits.

Alternatively, in case the binding agent comprises HRP, the visualization method of the invention may comprise a further step of incubation of a sample comprising discrete deposits of the second substrate bound to said binding agent in the deposition media described above. Such further step may be advantageous in some embodiments when a signal associated with the deposited second substrate may weak, or the size of the primary deposit is relatively small. The additional deposition step allows further amplification of the signal associated with the deposit and it may also increase the size of detectable deposits at single target sites. Further, the step also allows modifying the character of the detectable signal, e.g. changing spectral characteristics of the signal, e.g. the initial label detectable as a red signal may be substituted for a label detectable as a green signal by using conjugate molecules comprising said green label for this additional deposition instead of conjugate molecules comprising a red label used for the initial deposition (at step (b) of the method). Such flexibility of the method of the invention, however do not add an extra complexity to reagents used in additional steps of detection, as all embodiments of incubation media of steps (a) and (b) (discussed above) of the method may be successfully used without substantial modifications in these addition steps.

In one embodiment the invention relates to washing media, i.e. media for removing the rests of compounds (of incubation medium) from the sample after the technical effect of the incubation has taken place. The method of the invention may comprise one or more washing steps typically following a step of incubation of the sample in media described above, e.g. between steps (a) and (b), etc. Typically, a washing medium will be the same medium that has been used for incubating of the sample in a step preceding the washing step without the essential compounds of the incubation media, i.e. without binding agent, substrates of the enzyme, etc.

In one embodiment, the invention relates to a media for quenching the endogenous oxidoreductase activity. This type of media may be any media of such kind that is routinely used for the purpose in the art, for example a solution of hydrogen peroxide. This medium may be used before step (a) of the method. It can also be used after step (b) and before additional steps of detection of the deposited second substrate. Application of this medium at this stage of the procedure may used for quenching the residual oxidoreductase activity in the sample.

Discrete Deposits of the Second Substrate and Visually Distinct Dots

It is surprisingly found that using particular conditions of deposition media comprising particular conjugate molecules of the second substrate of enzyme with oxidoreductase activity and relatively low amounts of the first substrate of enzyme with oxidoreductase activity a peroxide compound, such as DAB and hydrogen peroxide, it is possible to form discrete deposits of said conjugate molecules at single target sites of the invention that have distinct physical features, namely round-shaped deposits larger than 0.4 micrometer in diameter, which can be directly observed using a regular microscopic optics or visualized as distinct dots. Using a similar amplification system (that employs the HRP-DAB mediated deposition of detectable conjugate molecules, see for details WO2009036760, WO2010094283 and WO2010094284) it has been possible to improve the traditional HRP-DAB IHC staining in that the homogeneous color pattern of target staining has become more crisp improving thereby the intracellular resolution of cellular structures, e.g. membrane, cytoplasm, and nucleus. The present visualization system provides instead a dotted pattern of target staining, wherein one single dot correspond to one individual target unit, such as one individual target molecule, allowing thereby the intracellular resolution of individual single target units such as single target molecules.

The deposits of detectable conjugate molecules of the invention produced by the method of the invention are three dimensional and have a substantially spherical shape, which in a two dimensional field, e.g. a microscopic field, are observed as distinct substantially rounded dots. Accordingly, the term "rounded dot" (interchangeably used herein with terms "dot" and "distinct dot")" designates in the present context a spherical deposit of detectable conjugate molecules of the invention observed in a two-dimensional field as a distinct substantially rounded dot. The term "distinct" in the present context means that a dot of the invention is distinguishable to the eye or mind as discrete The term "substantially rounded" means that a distinct dot of the invention has eccentricity that is around or less than 0.65. A dot according to the invention has a diameter of around or greater than 0.4 microns. The term "around" in the present context means +/−0.05-0.5 micrometer. In comparison, a "dot" of a deposit of the DAB stain by the traditional DAB-HRP method, or a single deposit of the stain at target sites obtained by the methods of WO2009036760, WO2010094283 and WO2010094284, or biotinyl- and fluorescyl-tyramide deposits by the CARD method has a size that is under the resolution limits of the regular microscopic optics (such as 4× or 10× magnification bright field or fluorescent optics), i.g. less than 0.1 microns. Accordingly, it is impossible to directly observe individual single target units visualized by the latter methods in a low magnification microscopic field (such as. 4× or 10×). The method described herein allows detecting and visualizing single deposits of detectable conjugate molecules of the invention at single target sites and thereby observe immobilized single units of targets in samples using low-magnification optics.

The term "one single deposit of the second substrate" (of enzyme with oxidoreductase activity) or "one single deposit of detectable conjugate molecules" (of the invention) relates to a single accumulation of a plurality of conjugate molecules of the second substrate. According to the invention, one distinct deposit of second substrate the invention may comprises from about 1000 and up to 1000000 conjugate molecules or more.

As discussed above, the second substrate deposited at a single target site may comprise visually identifiable molecules, e.g. molecules that comprise a visually detectable label, e.g. a fluorescent label. Accordingly, in one embodiment, a dot of deposit of such second substrate may be detected by a microscopist by using a conventional fluorescence microscope straight after the deposit has been formed. Deposits of reporter molecules that comprise labels that are not directly observable by standard microscopic optics, e.g. a member of a specific binding pair, are to be visualized according to the invention using at least one an additional step detection step, e.g. an additional step (c) described above.

The number of dots, their size and visual appearance can be controlled. For example, in different embodiments dots of a particular size and particular appearance (e.g. particular color) may be produced.

In one embodiment, the size of deposit and the dot size may be varied by using binding agents involved in formation of target sites of the invention comprising different number of enzyme moieties (the terms "enzyme moieties" or "enzyme" is in the present context mean an enzyme with oxidoreductase activity), e.g. the number of HRP per binding agent. In another embodiment the dot size may be controlled by duration the deposition process. In another embodiment, the dot size may be regulated by the content of the deposition media, such as the amount of first and/or second substrates, or a peroxide compound in the deposition media.

Thus, in one embodiment the number of the enzyme units per molecule of binding agent used for formation of a target site may influence the size of a dot. It is found that the dot size may be directly correlated to the number of the enzyme moieties per complex comprising one or more binding agents and one single unit of a target: Larger dots are observed when binding agents used for formations the target sites comprise a larger number of enzyme moieties per molecule (under otherwise the same deposition conditions (i.e. same incubation time, same composition of the deposition media) compared to the dots obtained with use of the same binding agents, but comprising less enzyme moieties per molecule.

To produce a visible dot corresponding to one single deposit under conditions of the invention, it is sufficient that the target site comprises a single, i.e. one enzyme moiety, e.g. a binding agent involved in formation of a target site comprises a single HRP moiety; however, in embodiments when two or more enzyme moieties are present at the same target site, the dot associated with this target site is larger than the dot in the first case. Accordingly, in one embodiment, a binding agent associated with one single target site may comprise one single moiety of HRP, in another embodiment, the binding agent may comprise two or more moieties of HRP, e.g. 2, 3, 4, 5, 6, 7, 8, 9 or 10. In one embodiment, the number of the enzyme moieties per binding agent is at least 2, preferably from 3 to 10, such as from 4 to 8 moieties.

It was surprisingly found that using binding agents that involved in formation of target sites of the invention wherein the number of enzyme moieties is at least 2 per molecule of binding agent, it is possible to produce dots of approximately equal size, under otherwise the same conditions, i.e. same conditions of the visualization procedure. Accordingly, in one embodiment, the invention relates to a method, wherein a sample comprising a immobilized target is incubated to one or more binding agents, wherein at least one of the binding agent comprises at least two enzymes with oxidoreductase activity. Thus, individual units of the target in this embodiment are visualized as individual substantially identical dots, i.e. as dots of the same size. In one embodiment the pool of molecules of a binding agent comprising an enzyme with peroxidase activity may be heterogeneous in that said molecules of comprise different number of the enzyme moieties per molecule, such as e.g. between 2 and 10 molecules, between 11 and 20 molecules, etc. In another embodiment, invention relates to the method, wherein every molecule of the pool of molecules of binding agent comprising an enzyme with peroxidase activity comprises the substantially identical number of the enzyme moieties per molecule of the binding agent, such as 1-3, 2-4-, 3-5, 4-6, 5-7, 6-8, 7-9, 8-10, 9-11, 10-12 etc. enzyme moieties per binding agent molecule.

In another embodiment the size of a dot is regulated by the amount of the first substrate in a deposition media, e.g. by the amount of DAB. Large dots, i.e. the dots which diameter is equal or larger than 0.4 microns, or equal or larger than 1 micron, or equal or larger than 2 or 3 microns, such as 4 or 5 microns, wherein the amount of deposited reporter (per dot) is not less than 1000 molecules, may be formed when the amount of DAB in the deposition media (in otherwise the same conditions of the visualization procedure, i.e. same binding agent, same reporter, same amount of the reporter, same concentration of the peroxide, same incubation time, etc) is in the range from about 0.01 mM about 1 mM, e.g. between 0.05 mM and 0.75 mM, such from around 0.075 mM to around 0.5 mM, such as. around 0.1 mM, e.g. 0.15 mM, or around 0.3 mM, e.g. 0.28 mM, etc. Dots of a smaller size, i.e. less than 0.4 microns, may be observed when both the higher and lower amounts of DAB in deposition media are used.

Composition and structure of the conjugate molecules of the inventions influence the capability of said molecules to be deposited as the second substrate of the invention (discussed above), and therefore they influence size of the deposits and apparent size of a dot. Further, a label of the conjugate may influence the appearance of a dot. For example, in embodiment when the conjugate molecule comprises a fluorescent label, the nature of the fluorofore group of the label will influence the appearance of the dot, e.g. under identical conditions conjugates comprising Lissamine (red fluorofore group) produce more intense dots than similar conjugates comprising Fluorescein (green fluorofore group). Further, higher amounts of the second substrate in the deposition medium, under otherwise the same conditions, may lead to formation of larger deposits.

The size of a dot may also be regulated by the time used for deposition of the second substrate. Longer incubation time in a deposition media allows depositing a larger amount of conjugate molecules at single target sites, increasing thereby the size of a single deposit and sequentially the size of a single dot. Increasing incubation time from 30 seconds to 10 minutes, in otherwise the same conditions, i.e. the same binding agent, same media, etc, may allow to the enzyme producing deposits that can be observed as single dots of a diameter around 5 micrometer. However, a further increase in duration of the incubation does not increase the size of a single deposit. However, longer times of the incubation in the deposition media do not decrease the size of single deposits, and if desirable, longer incubation times, e.g. up to 20 or 30 minutes or longer may be used. Thus, in different embodiments the duration of the deposition step of the method may vary from about 30 seconds to about 20 minutes, e.g. 1, 2, 3, 4, 5, 10, or 15 minutes, e.g. in one embodiment, the incubation time may be about 30 seconds, in another embodiment the time may be about 2 minutes. In one embodiment it is preferred that conjugate molecules are deposited during 5-10 minutes.

The amount of a peroxide compound in the deposition media may also be used as a factor for the regulation of size of the reporter deposit and, accordingly, the dot size. To obtain single dots that are up to 5 micrometers in diameter, the amount of a peroxide compound, such as e.g. hydrogen peroxide, in the deposition media should be less than 2 mM, preferably the amount does not exceed 1.5 mM. Higher amounts of a peroxide compound lead to formation of dots of a smaller size.

All the factors discussed above are termed in the present context "primary factors" as they influence formation of the initial, i.e. primary deposit of the second substrate. As mentioned, such primary deposits may be observed immediately after the deposition has taken place, e.g. in case conjugate molecules of the second substrate comprise a fluorescent label. In other embodiments, the primary deposits are not directly observable, however they may be visualized in one or more detection steps (termed in the present context "secondary visualization procedure") following the deposition step, e.g. in case the conjugates comprise a label that is a member of a specific binding pair, e.g. a hapten. Several factors of the secondary visualization procedure may also influence the visual size and appearance of the deposit as a dot, adding thereby to flexibility of the visualization system of the present invention. These factors are termed "secondary factors" accordingly.

The deposits of reporter molecules comprising a label that is a member of a specific binding pair may be visualized performing following detection steps (c') and (c") which directly or indirectly follows the deposition step:

(c') incubating a sample comprising discrete deposits of second substrate at single target sites with one or more binding agents capable of directly or indirectly binding to a detectable label of the deposited second substrate, wherein at least one of the binding agents comprises one or more detectable labels selected from radioactive, fluorescent or luminescent substances, members of specific binding pairs, or enzymes, thereby forming a complex comprising the deposited reporter and said at least one binding agent, (c") detecting in the sample the binding agent comprising the detectable label, thereby visualizing one or more reporter deposits at one or more individual target sites, and thereby visualizing one or more individual units of the target in the sample.

The term "indirectly" in the present context means that it may be one or more optional steps between the step (b) and (c'), e.g. a washing step.

By using reporter recognizing binding agents that comprise multiple enzyme moieties (as detectable labels) that can utilize chromogenic or fluorescent substrates, e.g. HRP or alkaline phosphotase (AP), it is possible to "stain" the deposits and produce distinct visibly detectable dots. In this case, the original size of a single, deposit may be "increased" or "decreased" by producing a distinct visually detectable dot of a certain size. In one embodiment, using a binding agent labeled with HRP or another oxidoreductase enzyme, and optimal conditions of the deposition (discussed above) the step of deposition may be repeated one or more times, thereby increasing the size of a detectable deposit at a single target site after every repetition. In another embodiment, using a binding agent labeled with HRP or another oxidoreductase enzyme, and sub-optimal conditions of the deposition (discussed above), the deposition step may be repeated yielding in deposits of a smaller size and, accordingly, smaller size of the corresponding detectable dots. In one embodiment, the deposition step may be repeated using conjugate molecules as second substrate which are different from the conjugate molecules used for the primary deposition, e.g. comprising another label, e.g. Lissamin label instead of Fluorescein label. In other embodiment, deposition time or deposition media conditions may be optimized to produce smaller or larger secondary deposits at the primary single target sites.

Thus, the visualization system used in of the present invention is a flexible and powerful amplification system. The double regulation system provide en extra flexibility which may be particular advantageous in some embodiments, e.g. in an embodiment when it is desirable to visualize large primary deposits as dots of smaller size. Dots of a smaller size may allow a more precise target unit positioning in the sample and also may allow detection of a larger dynamic range of target.

The double regulation described above may also be desirable in embodiments when two or more different targets are to be detected, or in embodiments when a target is present in the sample in a broad dynamic concentration range, or in embodiments when the primary deposit provides a weak detectable signal, etc. Visualization and quantification of targets present in a sample in a broad dynamic concentration range, i.e. there is a gradient of target concentration in the sample, may be challenging. At the lowest end of the range the number of the target site related dots may be insufficient to provide statistically valid information about the presence of the target throughout the entire sample, whereas at the highest end of the dynamic range, visualization of single units of the target may be challenged by the presence of a number of overlapping dots that cannot be visually distinguished separately from each other. Use of the primary and/or secondary factors described above to decrease an apparent size of the dots corresponding to large primary deposits may allow overcoming these problems and visualize and quantify targets present in samples in broad dynamic ranges.

Methods of detection of primary deposits of the second substrate may be different depending on type of the sample, features of the deposited molecules, etc. Any suitable method of the art may be used, e.g. in histological samples the deposits may be detected by using any standard IHC staining e.g. HRP-DAB staining, ELISA visualization or immunoblot staining may be used in other embodiments, etc.

EXAMPLES

The following is a description of non-limiting working examples illustrating the disclosed invention, in particular, a description of two alternative methods (I) and (II) of quantification of a target visualized according to the invention in a histological sample. The theoretical considerations are part of the description and not bounding. The described embodiments are exemplary and not limiting.

Example 1

Quantification of a Target in a Histological Sample (Method I)

Theoretic Considerations: Determination of Kd1, Kd2 and Pr (Method I)

In order to define a number of single entities of a target in a sample and, in particularly, total number of said units, e.g. single target protein molecules, several complex equilibrium experiments may be performed, employing:

1. Several Reference samples of a test material with identical, but unknown, levels of an immobilized protein molecules, Pr. (e.g. serial sections of a single block of homogeneous Her2 reference cells lines);
2. A primary antibody, Ab1 (e.g. a high affinity monoclonal Rabbit-anti-HER2) with unknown dissociation constant, Kd1 that binds to said protein,
3. An Enzyme labeled secondary antibody, Ab2 with unknown dissociation constant, Kd2, that binds to said primary antibody.
4. Technologies for visualizing almost every single molecule of said secondary antibodies as discrete visually distinguishable dots (termed herein "single molecule dots" or "SMD") (e.g. as described in PCT/DK2010/000137 or herein).

According to the present invention the level of immobilized target in a sample, e.g. a protein, can be expressed as counted SMD per nucleus (e.g. in reference cell lines samples), or per area or volume of a tissue sample, etc; the number of molecules can via Avogadro's Number be translated into concentration of said molecules in the sample.

It is generally accepted that theoretical framework for antibody protein interaction is a complex equilibrium. The antibody will reach equilibrium with the target protein:

$$Ab1 + Pr \leftrightarrow Ab1{:}Pr \qquad \text{F1}$$

Governed by the dissociation constant, Kd1 of the antibody:

$$\frac{[Ab1] \times [Pr]}{[Ab1{:}Pr]} = Kd1 \qquad \text{F2}$$

Under such equilibrium conditions, total protein, PrTotal and total antibody, Ab1Total will be distributed between free protein and complex and free antibody and complex $$Pr\text{Total} = Pr + Ab1{:}Pr \qquad \text{F3}$$

$$Ab1\text{Total} = Ab1 + Ab1{:}Pr \qquad \text{F4}$$

From F2 follows:

$$[Pr] = \frac{[Ab1{:}Pr] \times Kd1}{[Ab1]} \qquad \text{F5}$$

Substituting F5 into F3 gives:

$$Pr\text{Total} = \frac{[Ab1{:}Pr] \times Kd1}{[Ab1]} + [Ab1{:}Pr] \qquad \text{F6}$$

F6 can then be rearranged as the following:

$$Pr\text{Total} = [Ab1{:}Pr] \times \frac{Kd1 + [Ab1]}{[Ab1]} \qquad \text{F7}$$

The first experimental challenge lies in determining when this first equilibrium has been reached. [Ab1:Pr] can be detected and determined by a subsequent second equilibrium experiment with enzyme labeled Ab2 followed by SMD visualization. The first series of experiments, Exp1, can be used to establish that a sequential application of a constant concentration of Ab1 to samples with a constant amount of immobilized protein will eventually result in a constant amount of Ab1:Pr being detected in a subsequent second visualization step using enzyme labeled Ab2 and SMD detection.

The need to use multiple sequential additions of Ab1 arises from the fact that a single addition of Ab1 to a sample with immobilized protein will result in Ab1:Pr complex formation, and thus in a decrease in both Ab1 and Pr concentration. The first equilibrium may apparently be reached, but sequential additions of Ab1 to identical reference samples until a constant level of Ab1:Pr is detected must be used to access when a true equilibrium reflecting the concentration of Ab1 has been reached, i.e. when further additions of Ab1 will no longer result in an increase in Ab1:Pr being detected. A single or a few additions of Ab1 will result in equilibriums reflecting the total amount of protein in the immobilized samples rather than the concentration of Ab1. Ab1 will be depleted due to complex formation and the effective concentration in equilibrium will be significantly lower than the concentration of Ab1 applied.

Formula 4 reflecting the effects of lowered concentration of free antibody can be ignored, if multiple additions of antibody confirm that depletion or slow kinetics is not a case.

Experimental set-up to confirm the above theory may be designed as the following: A constant concentration of Ab1 is sequentially applied to samples with constant concentration of immobilized protein. The Ab1:Pr complexes formed are subsequently detected using an enzyme labeled secondary antibody and SMD visualization. Thus, a true equilibrium reflecting the concentration of Ab1, not the amount of immobilized protein, can be established. (The experiment confirming this theory is described below in Experiment 3a, which shows that, after four to five sequential 10 min-incubations reference samples with Ab1 no further increase in Ab1:Pr complexes is detected).

The theory behind the second complex equilibrium step is identical to the theory regarding the first (discussed above).

The second equilibrium is established between the enzyme labeled secondary antibody and the immobilized primary antibody protein complex:

$$Ab1{:}Pr + Ab2 \leftrightarrow Ab2{:}Ab1{:}Pr \qquad \text{F8}$$

Governed by the dissociation constant, Kd2 of the labeled secondary antibody:

$$\frac{[Ab2] \times [Ab1{:}Pr]}{[Ab2{:}Ab1{:}Pr]} = Kd2 \qquad \text{F9}$$

$$Ab1{:}Pr\text{Total} = Ab1{:}Pr + Ab2{:}Ab1{:}Pr \qquad \text{F10}$$

$$Ab2\text{Total} = Ab2 + Ab2{:}Ab1{:}Pr \qquad \text{F11}$$

From F9 follows:

$$Ab1Pr\text{Total} = \frac{[Ab2{:}Ab1{:}Pr] \times Kd2}{[Ab2]} \qquad \text{F12}$$

Substituting F12 into F10 gives:

$$Ab1{:}Pr\text{Total} = \frac{[Ab2{:}Ab1{:}Pr] \times Kd2}{[Ab2]} + [Ab2{:}Ab1{:}Pr] \qquad \text{F13}$$

F13 can then be rearranged into F14

$$Ab1{:}Pr\text{Total} = [Ab2{:}Ab1{:}Pr] \times \frac{Kd2 + [Ab2]}{[Ab2]} \qquad \text{F14}$$

This second equilibrium can only be established, if the concentration of Ab1:Pr remains essentially constant during the second equilibrium experiment, i.e. that no significant dissociation between protein and primary antibody takes place during washing steps and incubation with enzyme labeled secondary antibody. If this condition is observed, it is possible to substitute Ab1:PrTota of Formula 14 for [Ab1:Pr] of Formula 7.

This gives the next equation (Formula 15):

$$PrTotal = [Ab2{:}Ab1{:}Pr] \times \frac{Kd1 + [Ab1]}{[Ab1]} \times \frac{Kd2 + [Ab2]}{[Ab2]} \quad \text{F15}$$

Formula 15 can be regarded as the theoretical foundation of the absolute count experiments, i.e. experiments where the total number of target molecules in a sample is determined, because it describes a relationship between Kd1 and Kd2, which can be determined in equilibrium experiments in connection with the antibody titrations, and the total protein concentration and complexes of the protein with the antibodies that are visualized as dots.

These experiments may be performed as the following: A constant concentration of Ab1 is sequentially applied to samples with constant concentration of immobilized protein. The Ab1:Pr complexes formed are subsequently detected using an enzyme labeled secondary antibody and SMD visualization. The enzyme labeled secondary antibody (a constant amount thereof) is likewise sequentially applied multiple times. The experiment confirming this theory (described in Experiment 3b) has shown that after four to five sequential 10 min-incubations of enzyme labeled Ab2 with reference samples previously equilibrated with primary antibody no further increase in formation of Ab2:Ab1:Pr complexes was detected, neither a decrease (potentially resulting from a significant protein-Ab1 dissociation during washing steps and establishment of the second equilibrium) was detected. Thus, a true equilibrium reflecting the concentration of immobilized protein, [Ab1] and enzyme labeled [Ab2] can be established confirming the equation of Formula 15.

For the same reasons as discussed for Formula 4, now Formula 11 may be ignored. The effects of lowered concentration of free secondary enzyme labeled antibody can be ignored if multiple additions of this antibody confirm that depletion or slow kinetics is not a problem.

Tissue samples with unknown protein concentration level may be routinely incubated with primary antibodies in order to determine said unknown protein concentration. This step may be followed by steps of incubation with enzyme labeled secondary antibody followed by, yet, extra steps of visualization.

As a rule, in routine IHC staining procedures only single incubations with primary and secondary antibodies are used, and a physical agitation, either uncontrolled (due to gravity, evaporation or wicking) or controlled by active stirring of reagents on the slide, is an established practice. However, using mixing and/or relative high concentrations of both primary and secondary antibody, pseudo equilibrium conditions may be reached by a single reagent application, resulting in reproducible results (this is how the well-known histological staining systems work now, e.g. Envision system). Consecutive additions of an antibody reagent (primary or enzyme labeled secondary) results in relative stable equilibriums, and thus can also act as a safeguard against antibody depletion and allow, in contrary to the traditional IHC staining, the precise evaluation of the amount of the target in an IHC sample.

As described in Experiments below, the necessity of use of low amounts of high affinity primary antibody arises from the low value of Kd1 of the Her2 clone tested in combination with the need to use concentrations below Kd1 in order to measure Kd1. For routine use concentration well above Kd1 may be used, reducing the need for multiple additions. In case of the secondary antibody, it is the need to reduce dot overlap that prevents use of higher concentration. At higher concentrations the overlapping dots may prevent an accurate dot count, at least when counting is done manually.

When the staining conditions leading to forming non-overlapping SMDs are observed, the SMD can be counted as Pr, and, if PrTotal can be kept constant (e.g. in case of use of sequential sections of same reference material), experiments with varying [Ab1] and constant [Ab2] will allow determining Kd1; PrTotal and Kd2 will still remain unknown, but constant. This allows rearrangement of Formula 15 into Formula 16:

$$\text{Dots} = \text{Constant} \times \frac{[Ab1]}{Kd1 + [Ab1]} \quad \text{F16}$$

The Constant (C) reflects the value of PrTotal of the sample and the fraction of Ab1:Pr complexes that are detected in the second equilibrium reaction with constant [Ab2]. And it is the absolute number of Dots that can be detected under those conditions. The equation of F16 means that at high and increasing [Ab1] the number of Dots will approach, but never reach a constant level. At low and decreasing [Ab1] the number of Dots, which is a hyperbolic function of [Ab1], will approach a linear function of [Ab1].

The number of Dots as function of [Ab1] is a hyperbolic function, and Formula 16 is used to determine Kd1 by fitting experimental data correlating Dots with [Ab1] in experiments with constant reference material and constant [Kd2]. However, using sequential additions of Ab1 at concentrations close to Kd1 reproducibly allow accurate determination of Kd1 via an excellent fit to Formula 16.

Experimental set-up that allows determination of Kd2 is slightly more complex. The challenge is that concentrations of enzyme labeled secondary antibody that are close to Kd2 invariably will lead to formation of dots the number of which will be too high to count due to overlap problems. Use of a very low concentration of primary antibody and/or use of reference material with a low protein concentration would not be a solution, as a background from high concentrations of secondary antibody will give a very high background noise due to unspecific bound secondary antibodies, thus would not accurately reflect the protein concentration. This is further compounded by difficulties of establishing the equilibrium at very low primary antibody concentrations. An approach to overcome these challenges is to use both primary and secondary antibody in relative high concentrations, in case of the secondary antibody with concentrations around Kd2, and visualizing the bound secondary antibody by conventional IHC. By conventional IHC is meant that the enzyme labeled secondary antibodies are used to generate a brown deposit of 3,3'-diaminobenzidine (DAB), e.g. by using the Envision system, rather than SMD visualization. The intensity of such conventional DAB deposits is not linear and does not correctly reflect the quantity of molecules of a target in the sample, however the intensity of two deposits may be visually compared and determined to be of approximately of the same intensity. Indeed, this is how the IHC-staining results are at present interpreted: they are evaluated by comparing the intensity of the brown deposit in test samples and reference samples and follow the graphic or descriptive guidelines for the interpretation.

Using identical reference material, PrTotal (of F15) can be kept constant. If [Ab1] and [Ab2] are also constant, and Ab2:Ab1:Pr is visualized by conventional IHC as a brown deposit, the staining will be of constant intensity. Evidently, the intensity has to be within the dynamic range of conventional IHC so that variations in Ab2:Ab1:Pr are reflected in variable intensity of the brown deposit. IHC slides are normally scored on a scale: +0 (no color at all), +1 (weak intensity), +2 (moderate intensity), and +3 (highest intensity/brownish-black). In order to accurately reflects [Ab1:Ab2:Pr], the score should be within the +0.5 to +2.5 range, so that upwards or downwards variation is detected, and, preferably, within the +1 to +2 range, where the intensity variation as function of [Ab1:Ab2:Pr] is most pronounced and the background noise is minimal.

Having established a reference system in the desired dynamic range (i.e. within +1 to +2 and [Ab2] around [Kd2]) Experiment 3d (described below) is carried out using a lower constant concentration of Ab1, $[Ab1]_2$ with variable and increasing concentration of Ab2 relative to the initial reference experiment By increasing [Ab2], the concentration of [Ab2:Ab1:Pr] will at some point reach a level identical to the prior established reference level, resulting in an identical intensity of brown deposit. When the intensity of the brown DAB deposit is of identical intensity to the deposit formed with $[Ab1]_1$ and $[Ab2]_1$ it is to be concluded that:

$[Ab2:Ab1:Pr]_1 = [Ab2:Ab1:Pr]_2$

Thus, the identical staining levels have been reached by two different combinations of [Ab1] and [Ab2] and constant PrTotal. It follows to the equation:

$$\frac{Kd1 + [Ab1]_1}{[Ab1]_1} \times \frac{Kd2 + [Ab2]_1}{[Ab2]_1} = \frac{Kd1 + [Ab1]_2}{[Ab1]_2} \times \frac{Kd2 + [Ab2]_2}{[Ab2]_2}$$

As Kd1 is known, as well as $[Ab1]_1$ and $[Ab1]_2$ from experimental conditions, the equation may be reduced to Formula 17 (C1 and C2 are Constants):

$$C_1 \times \frac{Kd2 + [Ab2]_1}{[Ab2]_1} = C_2 \times \frac{Kd2 + [Ab2]_2}{[Ab2]_2} \qquad \text{F17}$$

Dividing by $C_1$ gives:

$$\frac{Kd2 + [Ab2]_1}{[Ab2]_1} = C_3 \times \frac{Kd2 + [Ab2]_2}{[Ab2]_2} \qquad \text{F18}$$

Formula 18 may be rearranged to allow isolation of Kd2:

$(Kd2 \times [Ab2]_2) + ([Ab2]_1 \times [Ab2]_2) = (C_3 \times Kd2 \times [Ab2]_1) + (C_3 \times [Ab2]_1 \times [Ab2]_2)$, which can be reduced to:

$$Kd2 = \frac{(1 - C_3) \times ([Ab2]_1 \times [Ab2]_2)}{(C_3 \times [Ab2]_1) - [Ab2]_2} \qquad \text{F19}$$

Where $C_3$ (which is equal to C2/C1, see above) is defined by:
5

$$C_3 = \frac{(Kd1 + [Ab1]_2) \times [Ab1]_1}{[Ab1]_2 \times (Kd1 + [Ab1]_1)} \qquad \text{F20}$$

$C_3$ relates to two hyperbolic functions on top of each other reflects a constant level of the brown staining that is derived from two different sets of experimental conditions: first, a reference level is established by reaching a first equilibrium reflecting $[Ab1]_1$ and $[Ab2]_1$; then, the same reference level is reached by using $[Ab1]_2$ and $[Ab2]_2$. Kd1 is known, Kd2 can thus be determined.

A reference level of the conventional staining intensity may be produced using $[Ab1]_1$ and $[Ab2]_1$. Using a different concentration of Ab1, $[Ab1]_2$ allows titration of [Ab2] until a level of identical staining intensity is reached by $[Ab2]_2$. This allows determination of Kd2 from Formula 19.

Returning to the original Formula 15, having determined Kd1 and Kd2, any SMD staining experiment fulfilling the proviso of reaching equilibrium in both steps and allowing an accurate SMD dot count, will allow determination of PrTotal in the reference sample(s) used.

Any reference sample, wherein PrTotal has been determined in this way, obtains a status of "absolute reference".

The absolute number of proteins (or any other immobilized target compound) in the immobilized sample has been counted and may be expressed in absolute terms such as molecules per area/volume/cell etc. depending on the nature of the immobilized sample.

EXPERIMENTALS

Abbreviations
MBHA 4-Methylbenzhydrylamine
NMP N-Methyl Pyrolidon
HATU 2-(1h-7-azabenzotriazole-1-yl)-1,1,3,3 tetramethyl uronium hexafluorophosphate; methenamminium
DIPEA DiIsopropyl EthylAmine
DCM Dichloro Methane
TFA TriFluoroacetic Acid
TFMSA TriFluor Methyl Sulphonic Acid
Flu Fluorescein
Dex Dextran
HPLC High Performance Liquid Chromatography
equi. Equivalent
L30 1,10,16,25-tetraaza-4,7,13,19,22,28-hexaoxa-11,15,26,30-tetraoxo-triacontane
L60, L90, L120, L150 different polymers of L30, comprising 2, 3, 4 or 5 L30 reapeats
CIZ 2-chloroZ=2-chloro Benzyloxycarbonyl
FITC FlouresceinIsoThioCyanate
HRP Horse Radish Peroxidase
GaM Goat anti-Mouse antibody
DNP 2,4 dinitro-fluorbenzene (DiNitroPhenyl)
ACim 4-amino-Cinnamic acid
LPR Liquid Permanent Red (Dako K0540)
Sin sinnapinic acid (4-hydroxy-3,5-dimethoxy cinnamic acid)
Caf caffeic acid (3,4-dihydroxy cinnamic acid)
Alpha-CHC apha-ciano-4-hydroxycinnamic acid
PNA-X peptide nucleic acid oligomer (N-(2-aminoethyl)-glycine) comprising different substituents coupled to the central nitrogen
A adenine-9-acetic acid,
C cytosine-1-acetic acid,
D 2,6-diaminopurine-9-acetic acid,
G guanuine-9-acetic acid,
Gs 6-thuioguanine-9-acetic acid,
P 2-pyrimidinone-1 acetic acid,
T thymine-1-acetic acid,
Us 2-thiouracil-1-acetic acid.
Dpr 2,3 diamino-propioninc acid, Phe phenylalanine,
Tyr tyrosine,
Trp tryptophane,
Lys lysine,
Cys cysteine,
betaala betaalanine, N,N diacetic acid
FFPE formaldehyde fixed paraffin embedded
SMD single molecule detection
Cross-linker a first substrate of an enzyme with oxidoreductase activity
Reporter a second substrate with an enzyme with peorxidase activity
RDM Reporter Deposition Medium
BAM Binding Agent Medium Materials and Protocols 1. Second Substrate (Reporter):
Sin-Lys(Sin)-Lys(Sin)-L150-Lys(Flu) (0328-018/D21047/D21067)

Synthesis is performed solution phase following solid phase synthesis of intermediates carrying free N-terminal amino groups and free lysine side chains amino groups. Alpha-N-Boc-(epsilon-N2-Cl-Z)-lysine was used to introduce lysine residues giving free epsilon-N-amino groups following cleavage from resin. The solution phase labeling is basically an extension of solid phase techniques, utilizing that the relative high molecular weight intermediates can be almost quantitatively precipitated with diethyl ether from TFA or NMP solution.

Boc-(Lys(2-Cl-Z))3-L150-Lys(Fmoc) is prepared on solid phase. The Fmoc group is removed, followed by fluorescein labeling as described above. The intermediate NH2-((Lys(NH2))3-L150-Lys(Flu) results from cleavage from resin. It is precipitated with diethyl ether, dissolved in TFA, precipitated then dissolved in NMP and made basic with DIPEA. This solution is mixed with an equal volume of 0.2 M sinnapinic acid (4-hydroxy-3,5-dimethoxy cinnamic acid) in NMP activated by HATU and DIPEA. After 10 min the labeling is complete and the crude product is further "scrubbed" by addition of ethylene diamine to a concentration of 10% for 5 minutes. Following precipitation with diethyl ether, the product is further dissolved in TFA and precipitated with diethyl ether three times to remove low molecular weight debris. Prior to "scrubbing" with ethylene diamine, mass spectroscopy shows two kinds of adducts (and combinations thereof): +(176)n indicating extra ferulic acids (phenolic esters on other ferulic acids and fluorescein) and +98 (N,N'-tetramethyl uronium adducts, likewise on unprotected phenolic groups). These are completely removed by the ethylene diamine treatment, and active esters and ferulic acid oligomers are likewise decomposed.

Other molecules as the second substrate/reporter suitable for the purposes of present invention are described in PCT/DK2010/000137 and incorporated herein by reference i.e. reporter conjugate molecules described on pages 86-100 of WO2011047680 (PCT/DK2010/000137).

2. Binding Agents:

2.1. Goat Anti-Rabbit Antibody Conjugated with Dex70 Conjugated with HRP (L348.111, Fractions 10-11.)

11 nmol 70 kDA MW dextran was reacted with 484 nmol HRP in 316 microliters of buffer A (100 mM NaCl, 25 mM NaHCO$_3$, pH 9.5) for 3 h at 40 C. Thereafter 44 nmol Goat-anti-Rabbit 196 microL water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising Goat-anti-Rabbit (GaR) and HRP. The product was divided into 4 fractions based on conjugate size: The first two fraction containing product (Frac. 8-9) eluded as a first peak, presumably containing some cross linked conjugates, then followed by a broad shoulder that was divided into fractions 10-11 (homogeneous large conjugates) and fractions 12-21 (smaller variable conjugates) and finally unconjugated enzymes and antibodies in fractions 22-42. Measurements on individual product fractions, as well as fractions containing non-conjugated antibody and HRP, showed a total conjugate recovery of 87%. Assuming direct proportionality between incorporated HRP and Dextran showed that fractions 10-11 contained 10.9 HRPs and 0.96 antibodies per Dextran. Only these two fractions were used for experiments.

2.2. Anti-HER2-Antibody Conjugated with Dex70 Conjugated with HRP (D21100, Fractions 9-10)

4.6 nmol 70 kDA MW dextran was reacted with 202 nmol HRP in 125 microliters of buffer A (100 mM NaCl, 25 mM NaHCO$_3$, pH 9.5) for 3 h at 30 C. Thereafter 18 nmol antiHer2 in 489 microL of water was added to the dextran-HRP conjugate and the mixture was allowed to react for further 21 h at 30 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising antiHer2 and HRP. The product was divided into 4 fractions based on conjugate size: The first two fraction containing product (Frac. 7-8) eluded as a first peak, presumably containing some cross linked conjugates, then followed by a broad shoulder that was divided into fractions 9-10 (homogeneous large conjugates) and fractions 11-19 (smaller variable conjugates) and finally unconjugated enzymes and antibodies in fractions 20-41. Measurements on individual product fractions, as well as fractions containing non-conjugated antibody and HRP, showed a total conjugate recovery of 68%. Assuming direct proportionality between incorporated HRP and Dextran showed that fractions 9-10 contained 9.1 HRPs and 0.6 antibodies per Dextran. Only these two fractions were used for experiments.

2.3. antiFITC Antibody Conjugated with Dex70 Conjugated with HRP (AMM 353-022 Fractions 8-11.)

11 nmol 70 kDA MW dextran was reacted with 484 nmol HRP in 316 microliters of buffer A (100 mM NaCl, 25 mM NaHCO$_3$, pH 9.5) for 3 h at 40 C. Thereafter 66 nmol antiFITC in 196 microL of water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising antiFITC and HRP. The product was divided into 3 fractions based on conjugate size: The first fractions (8-11) containing product eluded as a first peak, then followed by a broad shoulder (smaller variable conjugates, frac. 12-27) and finally unconjugated enzymes and antibodies in fractions 28-45. Measurements on individual product fractions, as well as fractions containing non-conjugated antibody and HRP, showed a total conjugate recovery of 90%. Assuming direct proportionality between incorporated HRP and Dextran showed that fractions 10-11 contained 11.7 HRPs and 0.80 antibodies per Dextran. Only these two fractions were used for experiments.

2.4 Other binding agents suitable for the purposes of present invention are described in PCT/DK2010/000137 and incorporated herein by reference, i.e. binding agent molecules described on pages 100-106 of WO2011047680 (PCT/DK2010/000137).

3. First Substrate

DAB, ferulic acid and alpha-ciano-4-hydroxycinnamic acid (alpha-CHC) were used as the first substrate at the following conditions:

|  | DAB | Ferulic acid | Alpha-CHC |
|---|---|---|---|
| Optimal amount (Range) | 0.14 mM (0.1 mM-less than1 mM) | 1.5 mM (0.5 mM to 5 mM) | 5 mM (1.5 mM and 15 mM) |
| Optimal H$_2$O$_2$ amount | 1.5 mM | 0.9 mM | 0.6 mM |
| Optimal deposition time | 5-10 min | 10-15 min | 10-15 min |
| Optimal second substrate | Contains Fer or Sin | Contains Sin | Contains Fer |
| Dot diameter | 3-4 microns | 3-4 microns | 2-3 microns |

Compared to DAB, dots of a similar diameter with ferulic acid were obtained when incubation time was doubled; with alpha-ciano-4-hydroxycinnamic acid the incubation time was as for DAB, however the dots were smaller (2-3 microns in diameter compared to 3-4 microns for DAB).

4. Other Reagents

DAB chromogen solution (Dako K3465)
LPR chromogen solution (Dako K0640)
Haematoxilin counterstain (Dako S3301)
Wash buffer (Dako S3306)
Target retrieval solution (Dako S1699)
Mounting media Dako Fairmount (S3025)

5. Test Material

As a test material serial sections of pellets of formalin fixed paraffin embedded cell lines sk45, df45, df23 expressing Her2 were used (these cell lines will further be referred to as the 0+, the 1+ and the 3+ cell line, correspondingly). These cell lines are the 0+, 1+ and 3+ control material for FDA approved Dako HercepTest for breast cancer. Pellets of the cell lines were embedded in a single block of paraffin to provide sections where the every cell lines present. The choose of the test material reflects availability of the material (e.g. each single block provides hundreds of serial sections, the presence of three different cell samples on each test slide allows inter correlation between the results of one staining procedure of three different test samples).

6. Pretreatment of Test Material:

Slides with FFPE sections of blocks containing the three cell lines (further referred as "slides") were deparaffinized by emersion in xylene (2×5 min) followed by 96% ethanol (2×2 min) and 70% ethanol (2×2 min). Then, the slides were washed with deionized water and transferred to Target retrieval solution, either the high pH solution (Dako S2375), diluted 10× (examples 1 and 2 with anti cytokeration) or low pH solution (Dako S1700) (see examples 10.3-10.8 below). The slides were then heated to boiling in a microwave oven (approx 5 min) and gently boiled for 10 min.

Afterwards the slides were allowed to cool for min 20 min and then were transferred to a wash buffer (Dako S3006) diluted 10×.

7. Primary Antibodies:

Pan specific anti-cytokeratin antibody (Dako M3515, monoclonal mouse) was used both as concentrate and diluted solution. Antibody dilutions were made based on total protein concentration (indicated on each vial) and considering the molecular weight of the antibody (150 kDa/mol). This antibody is further referred as "anti-cytokeratin".

Anti-Her2 antibody was a monoclonal rabbit antibody (Dako clone 25-11-3). Dilutions were made based on calculated total protein concentration in a concentrated solution and the molecular weight of the antibody of (150 kDa/mol). The antibody is referred herein as "anti-HER2".

8. Media

Binding Agent Medium (BAM)
0.1% 4-aminoantipurine, 0.2% Procline 2% BSA, 0.2% Casein, 2% PEG, 0.1% Tween20, 0.1 M NaCL, 10 mM HEPES, pH 7.2. (ABCPT-buffer)

Reporter Deposition Medium (RDM):
50 mM imidazole HCl pH 7.5, 0.1% Nonidet P40, 0.1%, benzalkonium chloride, 0.005% (1.5 mM) hydrogen peroxide, 9. Instruments.

Dako Autostainer Classic. This instrument is a totally open and freely programmable automated IHC instrument where reagents and incubation times can be used and set at will. The instrument performs four basic actions 1. Aspirate reagent.
2. Blow wash buffer off horizontally placed slide.
3. Dispense reagent onto slide. (Known as sip and spit.)
4. Wash a slide by flushing it with wash buffer.

A typical program for a single slide is described below in protocol 1. For all SMD experiments the initial peroxidase block and the dot forming steps were kept invariable:

10. Staining Protocol 1

Peroxidase block, 5 min in Dako S2023
Wash
(a) Formation of target sites:
Primary antibody,
Wash
HRP-Labeled secondary antibody,
Wash.
(b) Formation of reporter deposits at target sites
Incubation of samples (a) 10 minutes with 0.28 mM DAB and 5 µM reporter (D21047) in RDM.
Wash
c) Detection of reporter deposits at single target sites
Anti-FITC-AP, 10 min, 20 nM D20036 in BAM
Wash
LPR, 10 min, Dako K0640
Wash
d) Haemotoxylin counterstain
Haematoxylin, 5 min
Wash with deionized water
f) Mounting Additional washes may be introduced into the automated protocol. The automated scheduler will keep overall protocol time at a minimum, by reducing duration of washing steps to a minimum; however, duration of washing steps will depend on loading of the instrument. If a single slide is programmed to be stained, a single washing step might be reduced to 20 seconds, while a full load of 48 slides significantly increase washing time. To keep this time variation minimal, 10 slides in average were stained in each run. Accordingly, washing step duration was kept approximately 2 min per step. Multiple washes following reporter deposition and incubation of the deposits with anti-FITC-AP assures a minimal LPR background staining. Despite of massive amplification (it is estimated that each red Dots derived from a single antibody-dextran-HRP molecule bound to the target comprise in average 100 billion molecules of LPR) there can virtually no background be detected.

Extra washing might be recommended in order to reach the highest level of amplification and lowest background staining, while reporter and reporter binding agent are used in relative high amounts.

11. Evaluation of Staining

Figure 3:
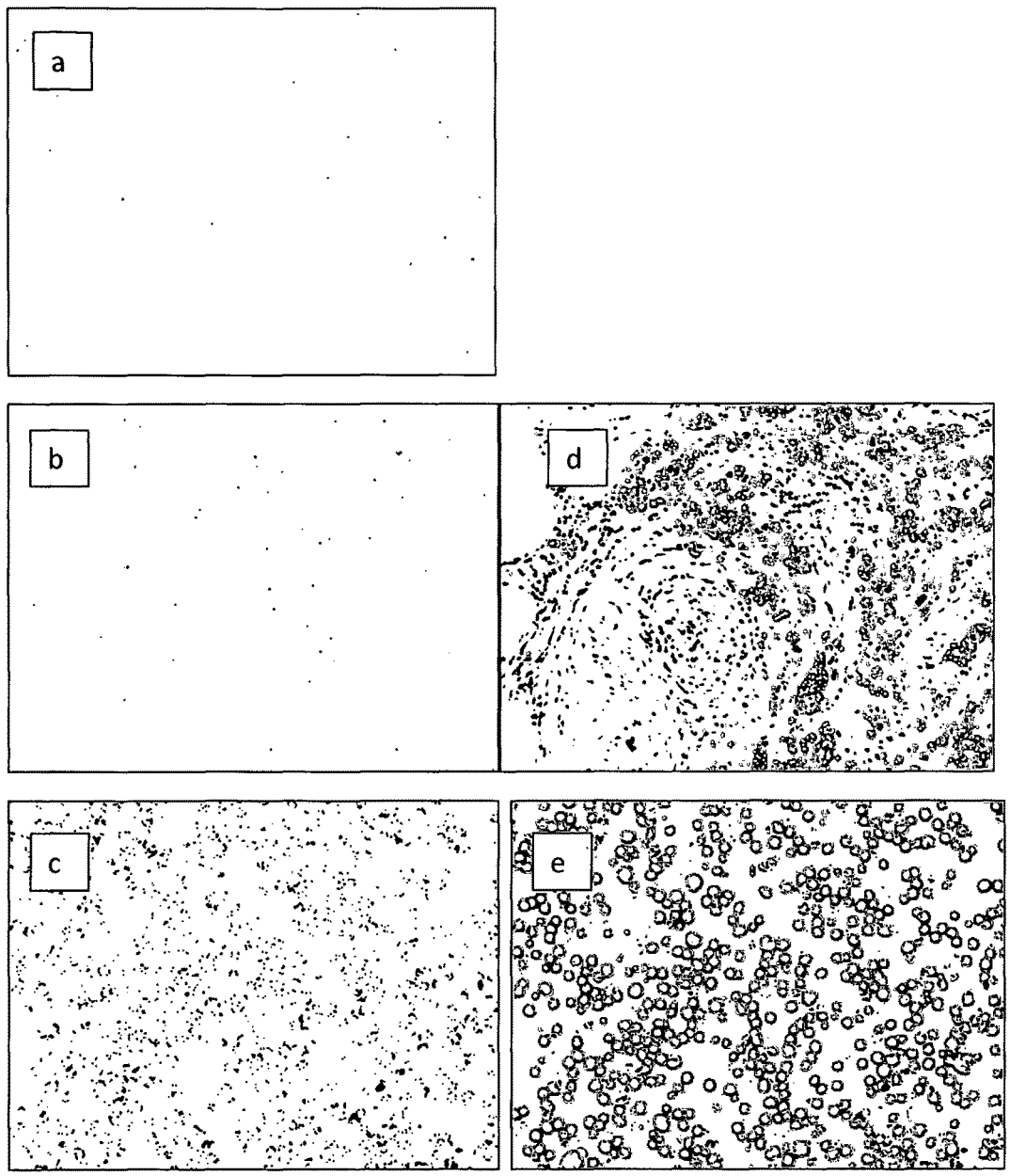
FIG. 3 shows the results of immunostaining of Her2 positive cells according to the visualization method of the invention: a. Single color segmentation of 10× image of 0+Herceptest control cell line. 21 Dots (black) per image identified; b. Single color segmentation of 10× image of 1+ Herceptest control cell line: 36 Dodts (black) per image identified; c. Single color segmentation of 10× image of 3+ Herceptest control cell line: 2567 Dots (black) per image identified; d. Two color segmentation of 10× image of Mamma carcinoma. Dots are white, nuclei black, background grey; e. Two color segmentation of 10× image of 3+ Herceptest control cell line. Dots are black, nuclei white, background grey (the same sample as c).

Dot counting was initially performed manually, by visual inspection of SMD stained slides and their images. Automated image analysis was performed using the freeware JMicrovision vs. 1.27. In an exemplary embodiment, LPR red Dots produced as described and haematoxylin stained nuclei were automatically counted. Automated counts were verified by visual inspection and manual counts. Segmentation and object abstraction could be based on hue alone in Hue, Saturation, Intensity, (HSI) color space, i.e. both intensity and saturation set to full 0-255 range. Dot hue was set to 188 (violet)-255 and 0-16 (orange), nuclear hue to 76 (green) to 163 (blue). Dot-nuclear contrast was enhanced by over exposing red (1.2), neutral green (1.0) and under exposure of blue (0.56) during image capture performed on an Olympus BX51 microscope fitted with a DP50 5.5 Mpixel camera and CellD image capture software. FIG. 3 demonstrates the processed images of the cells and the results of the dot count.

Presuming that one molecule anti-cytokeratin (cAb) is associated with one dot, the theoretical number of dots (Ndot) may be calculated using the following formula $$Nd = \frac{[cAb_c] \times Ndot_{max}}{Kd + [cAb]_c} \quad \text{(Formula 1)}$$

Wherein [cAb] is the concentration of anti-cytokeratin antibody, and Kd is the dissociation constant of the anti-cytokeratin antibody, i.e. cAb, and $Ndot_{max}$ is a constant.

The constant named $Ndot_{max}$ means maximal number of dots and in the present content means that the number of dots approaches the maximum value when the used concentration of an antibody is significantly above its Kd value, i.e. when the anti-cytokeratin antibody are used in a concentration that is far beyond the Kd value.

This formula is derived from the formula for the dissociation constants for the primary and secondary antibodies with the prerequisite that the absolute concentration of protein in every test sample (i.e. samples of cells +0, +1 and +3, 8 slides of each cells line with different concentrations of the antibody as indicated in the table below) is constant and the concentration of the secondary antibody is kept unvarying between slides.

The table (1) shows the number of experimentally obtained and theoretically calculated dots for every sample 1-8 for all three test cell lines:

| Slide | Concentration of primary antibody nM | Dots counted and calculated, total of 3 images in +0 cell line counted | calculated | Dots counted and calculated, total of 3 images in +1 cell line counted | calculated | Dots counted and calculated, total of 3 images in +3 cell line counted | calculated |
|---|---|---|---|---|---|---|---|
| 1 | 2.25 | 165 | 170 | 318 | 316 | 376 | 389 |
| 2 | 5 | 293 | 292 | 445 | 542 | 627 | 667 |
| 3 | 10 | 384 | 411 | 731 | 765 | 879 | 941 |
| 4 | 13.3 | 487 | 458 | 920 | 851 | 1043 | 1048 |
| 5 | 20 | 502 | 518 | 968 | 962 | 1140 | 1185 |
| 6 | 25 | 581 | 547 | 1026 | 1015 | 1333 | 1250 |
| 7 | 30 | 669 | 567 | 1159 | 1054 | 1546 | 1297 |
| 8 | 40 | 629 | 595 | 1269 | 1106 | 1663 | 1361 |

12. Experiments 12.1. Determination of Kd of Anti-Cytokeratin Antibody 8 slides with FFPE sections +0, +1 and +3 cell lines were pretreated and stained as described above (see pretreatment and protocol 1).

The primary antibody (anti-cytokeratin), was applied for 20 min in varying concentrations as described in the table:

| Slide number | Concentration of M3115 in BAM |
|---|---|
| 1 | 40 nM |
| 2 | 33 nM |
| 3 | 25 nM |
| 4 | 20 nM |
| 5 | 13 nM |
| 6 | 10 nM |
| 7 | 5 nM |
| 8 | 2.5 nM |

The slides were then mounted with aqueous Faramount. 3 images of each cell line pellet on each slide were captured, red colored dots were manually counted in each image and the number of counted dots was compared to a theoretically calculated number of dots in the samples.

Figure 4:
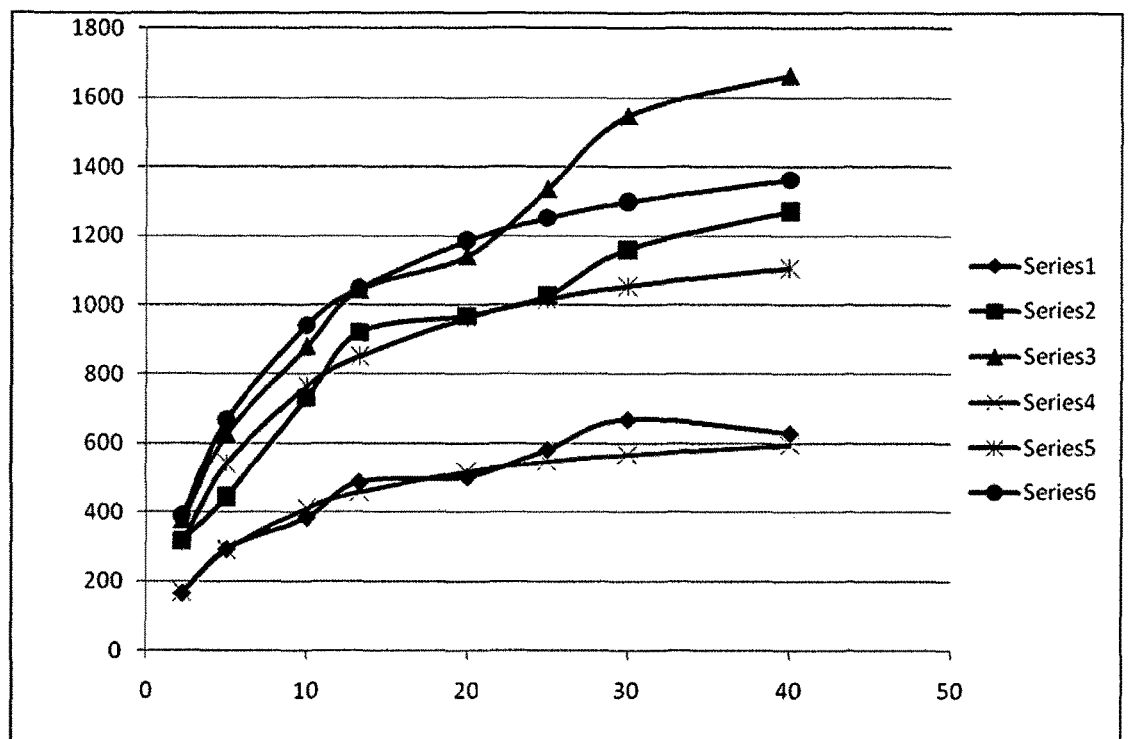
FIGS. 4-7 are graphic presentations of the results of Tables 1-4 of Experiments 12.1, 12.3a, 12.3b and 12.3c, accordingly (for details see the corresponding description).

Results of the SMD visualization experiments given in table 1 are also shown graphically in FIG. 4, wherein the curves of series 1, 2 and 3 corresponds to the results of experimental count of dots of +0, +1, and +3 cell samples, and series 4, 5 and 6 corresponds to the results of the theoretical calculation of dots of +0, +1, and +3 cell samples.

By fitting the curves generated from the formula to the curves generated from the experimental data, approximate values of Kd1 and $Ndot_{max}$ can be determined. Thus, Kd1 was set to 7 nM, for all three calculated series, $Ndot_{max}$ to 700 (+0), 1300 (+1) and 1600 (+3).

A Kd value of 7 nM is in good agreement with experimental count across all three cell lines. In case of the +1 and +3 cell lines, calculated values are slightly below measured values for high concentrations of antibody. Anti-cytokeratin antibody M 3515 has a broad specificity and it recognizes several different cytokeratin subtypes. Theoretically, for each cytokeratin subtype the antibody may have a slightly different Kd since the surroundings the antigen may be different and it may influence the antibody binding. This explains a "non-perfect fit" with the hyperbolic curve. Furthermore, that some unspecific binding might take place at concentrations well above the Kd value.

Conclusion

The performed quantification can be considered to be precise because the results from experiments where different slides and different cell lines were used can be directly compared, i.e. dot staining pattern provides an easy and rapid digitalized quantitative evaluation of samples, i.e. by counting the visually distinct dots, e.g. 600 dots are easily distinguishable from 300 dots in another sample.

The Kd value of the used secondary antibody (D20168) is not known, and it has not been shown that an equilibrium is reached in this step of affinity binding, however control experiments did show that further incubation with primary antibody (prolonged incubation time and additional portions of antibodies) did not lead to significant increase in signal. Thus, if a constant fraction of primary antibodies is recognized by the secondary antibody during the experiment, the latter has no influence on the Kd measurement. Using multiple applications of secondary antibodies twice as many dots can be produced. In these applications maximal number of dots per slide ($Ndot_{max}$) is also doubled, but these does not influence measurement the Kd.

12.2. Determination of Kd of a Second Binding Agent (Goat-Anti-Mouse-Dextran-HRP Conjugate (D20168).)

This experiment was performed using conventional IHC stains (Dako Envision system).

Slides were pretreated as described, and subjected to the following staining protocol 2:
1. Peroxidase block, 5 min
Wash
2. Anti-Cytokeratin, 20 min in incubation media 1
Wash
3. HRP-labeled secondary antibody (D20168), 20 min in incubation media 1
Wash
4. DAB chromogen solution, 10 min
Wash
5. Haematoxilin stain, 5 min
Wash with water
Wash
Wash with de ionized water.

12 samples of each of the three cell lines (+0, +1 and +3) were divided in two series, wherein six slides of the first series were incubated with of 2.5 nM anti-cytokeratin antibody and further incubated with 6 different concentrations of D20168 (100 nM, 50 nM, 25 nM, 15 nM, 10 nM and 5 nM), and six slides of the second series were incubated with 10 nM anti-cytokeratin antibody and further incubated with 6 different concentrations of D20168 (100 nM, 50 nM, 25 nM, 15 nM, 10 nM and 5 nM). The slides of both series were than stained with DAB (as chromogen) and Haemotoxilin according to the above protocol.

For all three cell lines staining intensity increased with increasing concentration, but leveled off within the dynamic range of the IHC staining (below a score of +2.5).

As expected, using a higher concentration of primary antibody resulted in higher intensities of staining. The staining of the slide treated with 2.5 nM anti-cytokeratin and 100 nM D20168 (further referred as slide A) (of each cell line) was compared to the staining of slides with 10 nM anti-cytokeratin (within each cell line). Two independent mock observers were used to estimate the intensity of staining. They found that for all three cell lines the intensity of staining of the slide A was identical to the intensity of staining of the slide treated with 10 nM anti-cytokeratin and 15 nM D20168 (slide B). Because of the reference material was constant (same cell line control slides) and approximately the same staining intensity was observed in slides treated with different amounts of the primary and secondary antibody. it was concluded that the number of Cytokeratin-anti-Cytokeratin-D20168 complexes present in slides A and B (within one cell line) was the same. Accordingly, the following equation could be used to calculate Kd (i.e. Kd2) of the secondary antibody of D20168:

$$Kd2 = \frac{(1 - C_3) \times ([Ab2]_1 \times [Ab2]_2)}{(C_3 \times [Ab2]_1) - [Ab2]_2}$$

Wherein $C_1$, $C_2$ and $C_3$; $[Ab1]_1$=2.5 nM, $[Ab1]_2$=10 nM, $[Ab2]_1$=100 nM, $[Ab2]_2$=15 nM, and wherein $C_3$ defined from the following equation:

$$C_3 = \frac{C_2}{C_1} = \frac{(Kd1 + [Ab1]_2) \times [Ab1]_1}{[Ab1]_2 \times (Kd1 + [Ab1]_1)}$$

Thus, Kd2 of D20168 was calculated to be 25 nM.

12.3a. Establishment of Equilibrium Conditions for Primary HER2 Antibody.

Due to a low Kd (i.e. high affinity) value for the HER2 antibody clone tested, initial attempts to determine the Kd value by means similar to example 1 might give results that would not fit well with equilibrium conditions: a single application of a very low concentrations (100 pM) of the primary antibody may lead to formation of incomplete equilibrium. Therefore, in order to defined and secure conditions of the equilibrium conditions for the HER2 antibodies, sequential additions of the primary antibody were applied to the samples of all three lines. Slides treated with the lowest concentration (100 pM) of the antibody, where antibody depletion and incomplete equilibrium problems were expected to be most severe, were as well treated with two sequential additions of high concentrations of the secondary antibody, to compensate depletion in of the primary antibody step.

The staining was done according to protocol 1 with the specific concentrations, incubation times and number of sequential additions for the primary and secondary antibodies, as the following.

100 pM HER2 antibody, 1-6 sequential incubations, 10 minutes each:

| Slide number | Number of additions |
| --- | --- |
| 1 | 1 |
| 2 | 2 |
| 3 | 3 |
| 4 | 4 |
| 5 | 5 |
| 6 | 6 |

One wash followed each addition (prior to the following addition);

5 pM HRP-Labeled Goat-anti-Rabbit (L348-111 frac. 9-10), two sequential incubations, 10 min each.

Figure 5:
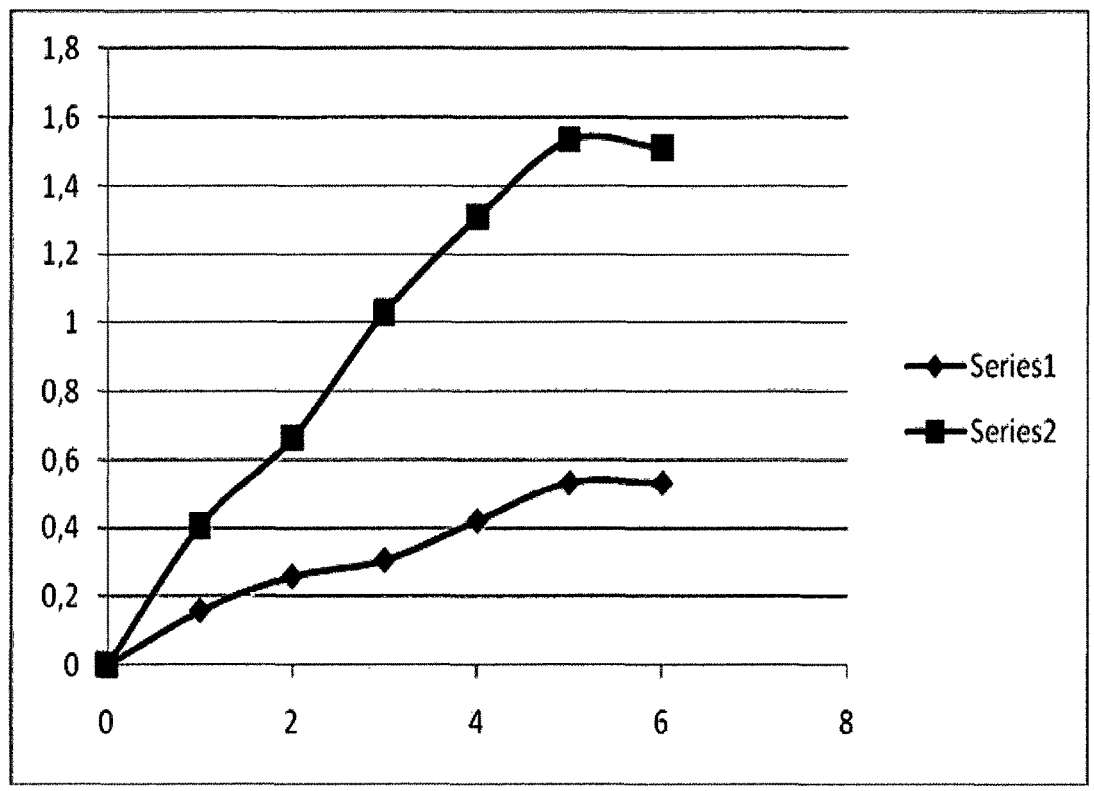

Three images (10× magnification) of each +0 and +1 cell line samples were taken and the number of SMD dots per nucleus was counted. The +3 cell line samples were disregarded due to a very intensive staining which did not allow an accurate count the dots. The results are presented in Table, 2 below (shown graphically in FIG. 5):

| Additions of anti-HER2 | Dot/nuclei(0+) (Series 1 of FIG. 5) | Dot/nuclei(1+) (Series 2 of FIG. 5) |
|---|---|---|
| 1 | 0.158 | 0.407 |
| 2 | 0.258 | 0.665 |
| 3 | 0.305 | 1.031 |
| 4 | 0.42 | 1.309 |
| 5 | 0.532 | 1.536 |
| 6 | 0.532 | 1.513 |

From the results of the experiment it was concluded that at least 5 additions of the HER2 primary antibody solution, were the amount of the antibody is 100 pM, is required to avoid depletion and establish true equilibrium condition in the tested samples.

12.3b. Establishment of Equilibrium Conditions for Secondary Antibody.

To define the equilibrium conditions for the secondary antibody, a high concentration of the HER2 primary antibody was used in the first step of the procedure which would expected to give a high level of bound primary antibody to the target, and a series of applications of low concentration of the secondary antibody (L348-111, fractions. 9-10), where depletion of the antibody would be expected to be most sever, was performed in the second step of the procedure.

The staining was done according to protocol 1 with the specific concentrations, incubation times and number of additions for the primary and secondary antibodies described below:

500 pM HER2 antibody, 2 sequential additions, 10 min each;
Wash
5 pM L348-111, 1-5 sequential additions, 10 min each:

| Slide number | Number of additions |
|---|---|
| 1 | 1 |
| 2 | 2 |
| 3 | 3 |
| 4 | 4 |
| 5 | 5 |

One wash was applied after each addition, prior to the following addition.

Three images (10× magnification) of each +0 and +1 cell sample were taken and the number of SMD dots per nucleus was counted. The +3 cell line samples were disregarded due to a very intensive staining which did not allow an accurate count the dots.

Figure 6:
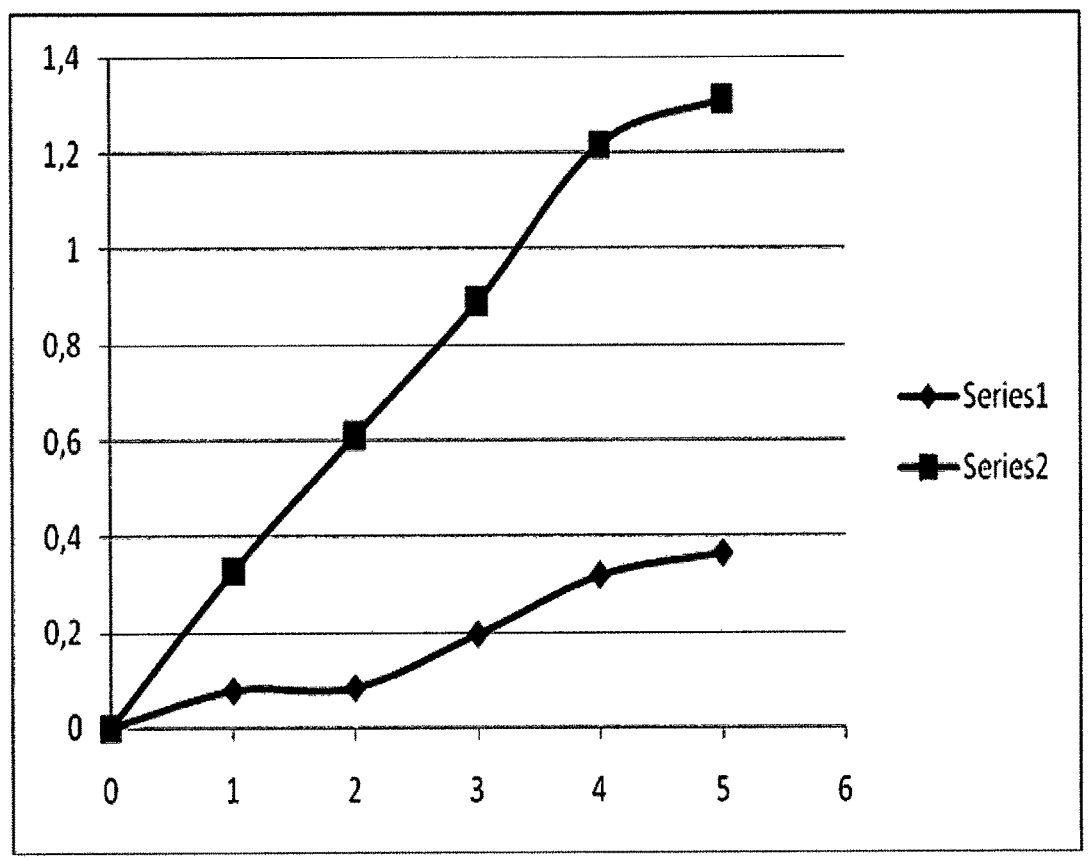

The results are presented in Table 3 (shown graphically in FIG. 6):

| Additions of Secondary antibody | Dots/nucleus (0+) (Series 1 of FIG. 6) | Dot/nucleus (1+) (Series 2 of FIG. 6) |
|---|---|---|
| 1 | 0.077 | 0.327 |
| 2 | 0.083 | 0.609 |
| 3 | 0.195 | 0.889 |
| 4 | 0.318 | 1.216 |
| 5 | 0.364 | 1.31 |

From the results of the experiment, it was concluded that at least 5 additions of 1.5 pM L348-111 frac. 9-10 was required to reach the equilibrium.

12.3c Determination of the Kd Value of the Anti-HER2.

From examples 3a and 3b it has been known that 6 sequential additions of 100 pM HER2 antibody and subsequently 5 additions of 5 pM L348-111 were required in order to reach the equilibrium conditions and measure the Kd values. Accordingly, SMD staining of 12 slides of samples of the tree cell lines was performed according to protocol 1 with the specific concentrations, incubation times and number of additions for the primary and secondary antibodies as described below:

6 concentrations of the HER2 antibody, 6 sequential additions, 10 minutes each:

| Slide number | Concentration of HER2 |
|---|---|
| 1 and 2 | 100 pM |
| 3 and 4 | 200 pM |
| 5 and 6 | 300 pM |
| 7 and 8 | 400 pM |
| 9 and 10 | 500 pM |
| 11 and 12 | 1 nM |

One wash step was applied after each addition and prior to the following;

5 pM L348-111, 5 sequential additions, 10 min each.

Three images (10× magnification) of samples of each +0 and +1 cell lines were taken and the number of SMD dots per nucleus was counted. The +3 were disregarded due to very intensive staining, likewise, the slides incubated with the highest concentration of the primary antibody (1 nM).

Figure 7:
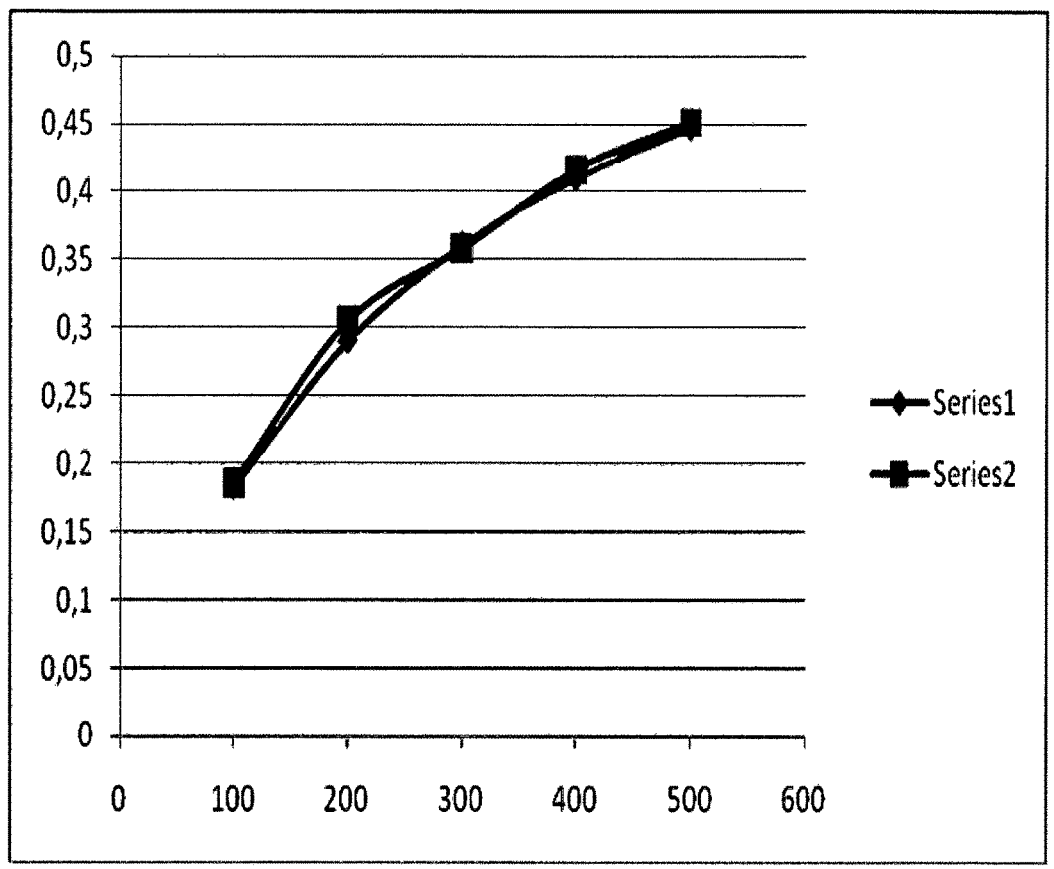

The results of the experiment with samples of the +0 cell line are presented in Table 4 below (and shown graphically in FIG. 7):

| Concentration of Anti-HER2 | Theoretically calculated number of dots Kd 280, max 0.7 dot/nucleus (Series 1 of FIG. 7) | Dot/nucleus experimentally counted in 0+ cell line (Series 2 of FIG. 7) |
|---|---|---|
| 100 | 0.183246 | 0.186 |
| 200 | 0.290456 | 0.305 |
| 300 | 0.360825 | 0.358 |
| 400 | 0.410557 | 0.416 |
| 500 | 0.44757 | 0.451 |
| 1000 | 0.546022 | 0.69 |

Use of very low concentrations of both primary and secondary antibodies (100-500 pM and 5 pM) correspondingly), combined with multiple sequential additions is necessary to reach the equilibrium conditions as demonstrated in experiments 3a and 3b. The 6 times addition of primary antibody at a concentration well above Kd (1 nM) should led to some background, which is expected, however the fit obtained from the 5 double determinations around Kd is very good. Using an iterative process of adjusting the Kd and the $Ndot_{max}$ of Formula I (see Experiment 10.1) was an alternating way: the data was fitted to a Kd value of 282 pM and a maximum dot count of 0.70 dots per nucleus at (hypothetical) target saturation.

12. 3d. Determination of Kd of L348-111 (Goat-Anti-Rabbit-Dextran-HRP Conjugate).

This experiment was performed using conventional IHC stains. Slides were pretreated as described, and subjected to the following staining protocol 3:

1. Peroxidase block, 5 min
Wash
2. Anti-HER2 in incubation media 1, 6 additions, 10 min each;

Wash
3. L348-111 in incubation media 1, 3 additions, 10 min each;
Wash
4. DAB stain, 10 min
Wash
5. Haematoxilin stain, 5 min
Wash with water
Wash
Wash with de ionized water.

For each of the three cell line, three slides were stained (in triplicate) with 100 pM anti-HER2 and 50 nM L348-111. The other six slides were stained with 500 pM anti-HER2 and with decreasing concentrations of L348-111 (50 nM, 25 nM, 17 nM, 11 nM, 7.5 nM and 5 nM correspondingly). Two independent observes of the staining results found that for all three cell lines the intensity of the triplicate stain (100 pM anti-HER2 and 50 nM L348-111) was identical to the slide treated with 500 pM anti-HER2 and 11 nM L348-111. As the reference material was constant (same cell line control slides) and a constant staining intensity was observed, it could be concluded that the same number of HER2-anti-HER2-L348-111 complexes were present. Accordingly, the following formula was used to calculate the Kd of the secondary antibody:

$$Kd2 = \frac{(1-C_3) \times ([Ab2]_1 \times [Ab2]_2)}{(C_3 \times [Ab2]_1) - [A2b]_2}.$$

Wherein $[Ab1]_1$ and $[Ab1]_2$ are two different concentrations of the primary antibody, and $[Ab2]_1$ and $[Ab2]_2$ are different concentrations of the secondary antibody.

Calculating $C_3$ from the following equitation:

$$C_3 = \frac{C_2}{C_1} = \frac{(Kd1 + [Ab1]_2) \times [Ab1]_1}{[Ab1]_2 \times (Kd1 + [Ab1]_1)},$$

And using the values of $[Ab1]_1$=100 pM, $[Ab1]_2$=500 pM, $[Ab2]_1$=50 nM, $[Ab2]_2$=11 nM, Kd2 of L348-111 was found to be equal to 28 nM.

In the equilibrium titration of example 3c the results were fitted to 0.70 dots per nucleus (at conditions of saturation with primary antibody and use of L348-111 at 1.5 pM concentratoion). Accordingly, using the following equation it is possible to calculate the total amount of HER2 (PrTotal) present in +0 cells:

$$PrTotal = [Ab2:Ab1:Pr] \times \frac{Kd1 + [Ab1]}{[Ab1]} \times \frac{Kd2 + [Ab2]}{[Ab2]},$$

wherein [Ab2:Ab1:Pr] is the concentration of complexes HER2-anti-HER2-L348-111, Kd1 is the constant dissociation of anti-HER2, and Kd2 is the constant dissociation of L348-111, $[Ab1]_1$ and $[Ab1]_2$ two different concentrations of the anti-HER2, and $[Ab2]_1$ and $[Ab2]_2$ are two different concentrations of L348-111.

Setting [Ab2:Ab1:Pr] at 0.70 SMD dots/nucleus, the first fraction to 1 and Kd2 to 28 nM and [Ab2] to 1.5 pM, the value of PrTotal is calculated to be 13.000 molecules/nucleus.

This value is in a good agreement with the data of the field (see, for example, David G. Hicks, D. G. and Schiffhauer, L. Assessment of HER2 Status by Immunohistochemistry: Routine Use of Controls for IHC Testing-Laboratory Medicine. 2011; 42(8):459-467) that the 0+ cell line express 21,600±6700 copies of the Her2 receptor on the surface of these cells.

Example 2

Quantification of a Target in a Histological Sample (Method II)

1. Theoretical Considerations

The method (II) for estimation of the total (absolute) number of target molecules in cells has a number of similar approaches compared to the method (I), however it has also some differences.

One of the problems associated with the previously described method is that equilibrium conditions should be established for both primary antibody and labeled secondary antibody. In case of high target concentrations this can be a problem as depletion of binding agents during incubations will occur and it will thus require multiple and prolonged incubations with the binding agents. The present method utilizes that using very high concentration of binding agents a "top" level of binding (which means that essentially all binding sites in the sample will be saturated with the corresponding binding agent) can be established without having the depletion problems. Evidently never 100%, but 90-99% binding of a protein target with a high affinity primary antibody, and 50-75% binding of the primary antibody with labeled secondary antibody may be reached. Within these ranges, experiments with a varying but high concentration of reagents can be used to establish more precise binding levels.

Further, using a mixture containing a high concentration of unlabeled secondary antibody and low concentration of labeled (the same) secondary antibody, equilibrium conditions can be reached, while only a small fraction of the primary antibodies bound to the target will be labeled.

The present method further utilizes the possibility provided by the present visualization method that labeled secondary antibody may be visualized in several ways, depending on degree of amplification. In case of low amounts of the target bound primary antibody, a labeled secondary (or a mixture of labeled and unlabeled) antibody can be used to produce countable dots. In case of high amounts of the target bound primary antibody, the same reagent (or mixture) can be used to produce a conventional stain. The experiment thus may comprise several steps:

1. Incubations with high concentrations of binding agents are used to establish equilibrium conditions leading to recognition of a high and known fraction of targets. Such experiments are carried out with both primary and labeled secondary antibody. Such conditions will further be referred as "top level" conditions.
2. Then, a mixture of labeled secondary and unlabeled secondary antibody that recognizes an unknown fraction of primary antibodies is prepared and used for incubation of a tissue sample with a high target expression that has been treated with a primary antibody at the top level conditions. The incubation is followed by visualization of the bound labeled secondary antibody with a conventional stain.
3. Using conventional staining, titration of the target bound primary antibody by the labeled secondary antibody at the top level conditions is performed. The important point is that equilibrium conditions need not be established between the target and the primary antibody. It is sufficient that using constant test material (the constant test material refers to a test material wherein the amount of the target is constant), a reproducible amount of the target is recognized. At some low concentration of primary antibody, a staining intensity is obtained that is identical to the level of staining that observed in step 2.
4. Using a method for visualizing single molecules as dots (as described in the present invention), a mixture of labeled and unlabeled secondary antibody is used to access a fraction of the target recognized by the same low concentration of the primary antibody as in step 3, relative to the fraction of the target recognized by the top level conditions of primary antibody.
5. Using the low level of primary antibody as of step 3, and the mixture of labeled and unlabeled secondary antibody as of step 2, single molecules are stained as dots and the number of dots per nucleus is evaluated.

From these experiments, the absolute number of targets can be determined. From experiments of steps 1 and 4, it is known which fraction of the target is recognized by the low concentration of the primary antibody. From experiments of steps 1 and 3, it is possible to deduce which fraction of the primary antibodies is recognized by the mixture of labeled and unlabeled secondary antibody used in experiment 2. We use the fact that the identical conventional staining levels are obtained in experiments of step 2 and 3 (which means that there is the identical number of the bound labeled secondary antibodies in the samples). Thus, we now know both the fraction of the target molecules recognized by the low concentration of the primary antibody, and the fraction of the primary antibodies recognized by the mixture of labeled and unlabeled secondary antibody of experiment in step 5. Multiplying these two factors gives the fraction of target molecules visualized as dots (see description of Experiment 1c below). As we further have counted the number of dots per nucleus, we know the number of target molecules present per nucleus. Thus, an absolute count has been performed.

2. Experiments

Materials and methods used in the following experiments, if not specifically disclosed, are as described above.

It is established that the Kd of the primary anti-Her2 antibody is 280 pM. (See experiment 3c) Using the antibody under equilibrium conditions (multiple additions until no further increase in signal is observed) at a concentration of 13.3 nM will result in labeling of 13.3 nM/(13.3 nM+0.28 nM) which is equal to approximately 97.9% of the primary target molecules.

Likewise, it is established that the Kd of the labeled secondary antibody is 28 nM. (See experiment 3d). Using the labeled secondary antibody under equilibrium conditions (multiple additions until no further increase in signal is observed) at a concentration of 25 nM will result in labeling of 25 nM/(25 nM+28 nM) which is equal to approximately 47.1% of the bound primary antibodies.

Experiment 2.1a.

As constant test material was used serial sections of pellets of formalin fixed paraffin embedded cell lines. The cell lines used were 3+ control material from Dako HercepTest.

Slides with FFPE sections of blocks containing the cell lines, from now on referred to as "slides" were de paraffinized by emersion in xylene (2×5 min) followed by 96% ethanol (2×2 min) and 70% ethanol (2×2 min). The slides were washed with de ionized water and transferred to low pH target retrieval solution (Dako S1700). The slides were then heated to boiling in a microwave oven (approx 5 min) and then gently boiled for 10 min. The slides were allowed to cool for min 20 min before being transferred to wash buffer, Dako S 2343.

The slides were then stained on the Autostainer using the following protocol:
Peroxidase block, Dako S2023, 5 min
Wash
Several sequential 10 minute additions of 13.3 nM anti-HER2 primary antibody
Wash
Several sequential 10 minute additions of 100 pM Goat-anti-Rabbit-Dextran-HRP (L348.111) mixed with 5 nM unlabelled Goat-anti-Rabbit.
Wash
DAB (Dako K5007), 10 min
Wash
Haematoxylin (Dako S3301), 5 min
Wash with water
Wash
Results:

Three 10 minute additions of 13.3 nM antiHER2 were sufficient to reach equilibrium conditions. A fourth addition did not lead to increased staining level. Two 10 minute additions of 100 pM Goat-anti-Rabbit-Dextran-HRP (L348.111) mixed with 5 nM unlabelled Goat-anti-Rabbit was sufficient to reach equilibrium conditions. A third addition did not lead to increased staining level. The maximum staining level reached corresponded to approx. +1. (Although this cell line is referred to as +3, the use of low concentration of labeled secondary antibody mixed with a high concentration of unlabeled secondary antibody leads to labeling of a small fraction of primary antibodies).

Experiment 2.1b.

Slides were pretreated as in Experiment 1a, and subjected to the following protocol (conventional DAB staining):
Peroxidase block, Dako S2023, 5 min
Wash
10 minutes anti-HER2 primary antibody in varying concentration in the range 30 to 50 pM.
Wash
Two sequential 10 minute additions of 25 nM Goat-anti-Rabbit-Dextran-HRP (L348.111). A control slide showed that a third addition did not lead to increased signal.
Wash
DAB (Dako K5007), 10 min
Wash
Haematoxylin (Dako S3301), 5 min
Wash with water
Wash
Results:

An incubation with 40 pM anti-HER2 for 10 minutes resulted in a staining intensity (+1) identical to the maximum staining level reached in experiment 1a. The 43 pM incubation resulted in a visibly higher staining intensity, whereas the 37 pM incubation gave a visibly lower staining intensity.

Experiment 2.1c

The slides were pretreated as in experiment 1a and subjected to the following protocol (SMD staining):
Peroxidase block, 5 min with Dako S2023
Wash
AntiHER2 primary antibody. Either 3 sequential 10 minute additions of 13.3 nM (slide 1) or one 10 minute addition of 40 pM (Slide 2-5)

Wash

Two sequential 10 minute additions of 500 femtoM Goat-anti-Rabbit-Dextran-HRP (L348.111) mixed with 5 nM unlabelled Goat-anti-Rabbit (slide 1-3) or two sequential 10 minute additions of 100 pM Goat-anti-Rabbit-Dextran-HRP (L348.111) mixed with 5 nM unlabelled Goat-anti-Rabbit (slides 4-5)

Wash

FITC-Reporter deposit: 10 min with incubation media 2 with 0.28 mM DAB and 10 microM D21067.

Three washes

Anti-FITC-AP: 10 min incubation, 20 nM D20036 in BAM

Three washes

LPR 10 min with Dako K0640 wash

Haematoxylin (Dako S3301), 5 min

Wash with water

Wash

The slides were subjected to image analysis. Images of the entire cell pellets were captured at 20× (appprox. 300×300 nm pixels) using a ScanScope (Aperio) slide scanner. The images were analyzed using JMicrovision vs. 1.27 software. Red dots were identified in Intensity, Hue, Saturation color space as (I=0-234, H=187-37, S=52-255), blue nuclei were identified as (I=0-201, H=148-221, S=0-190). A size threshold was further applied to dots, objects bigger than 30 pixels were counted as two dots, objects bigger than 45 pixels were counted as three dots. A lower threshold of 100 pixels was applied to nuclei to filter away debris and smaller fragments of nuclei.

Note that the partially overlapping color spaces allow identifying individual pixels as both part of a red dot and as part of a nucleus, consistent with the dark violet appearance of dots on top of nuclei.

RESULTS AND CONCLUSIONS

Results of the SMD staining of slides and dot calculation are shown in the Table below:

| Slide | Dots | Nuclei | Dots/nucleus |
|---|---|---|---|
| 1 | 56918 | 12388 | 4.59 |
| 2 | 151 | 13817 | 0.0109 |
| 3 | 177 | 13925 | 0.0127 |
| 4 | 52011 | 13618 | 3.82 |
| 5 | 61040 | 12939 | 4.72 |

Comparison of slide 1 to the average of slides 2 and 3 shows 388 times less bound primary antibody. As slide 1 represents around 97.9% (the value is derived from Kd1 of anti-Her2) of bound target molecules, application of 40 pM primary antibody for 10 minutes on the same test material (slides 2 and 3) gives rise to 1 in 396 target molecules being bound to the primary antibody (or 0.252%).

This data can now be used to analyze the results of Experiments 1a and 1b.

As mentioned, application of 40 pM primary antibody for 10 minutes results in labeling of 0.252% of the primary target. Subsequently, binding 47.1% (the value is derived from Kd of the secondary antibody) of the bound to the target primary antibodies to the secondary antibody results in 0.119% of the target being (indirectly) bound to the secondary antibody. This corresponds to Experiment 1c, i.e. using 40 pM primary antibody for 10 min. This must also be the case (as staining levels are identical) for Experiment 1b, where the 13.3 nM primary antibody incubation (97.9% of primary targets bound) was followed by the incubation with the mixture of 100 pM labeled secondary antibody with 5 nM unlabeled secondary antibody. Thus, it can be concluded that the use of this mixture leads to 0.119%/0.979=0.121% of the primary antibodies being bound to the labeled secondary; 0.121% of 0.252% of the target is equal to 3.06 ppm (parts per million). Accordingly, the 4.27 dots (in average) per nucleus observed in slides 4 and 5 count to 1.395.000 target molecule per nucleus (this follow from the following calculation: 4.27/0.00000306=1.395.000).

The precision of this evaluation can be made by comparing slide 2 and 3 with slides 4-5. There were observed 362 times more dots (in average) using the mixture with 100 pM labeled secondary (slides 2-3) antibody than with 500 fM (slides 4-5). As the mixture with 100 pM results in 0.121% primary antibodies being labeled, the mixture with 500 fM must lead to 362 times lower labeling the target with antibody, i.e. 0.121%/362=3.34 ppm. Using this figure to analyze slide 1 it can be calculated the level of labeling of target molecules in this slide: 97.9% of 3.34 ppm gives 3.27 ppm, and the observed 4.59 dots per nucleus corresponds to 1.402.000 target molecules per nucleus (4.59/0.00000327=1.402.000).

The invention claimed is:

1. A method for quantifying a target present in a sample, wherein said target is immobilized, comprising:

(a) incubating the sample with a first binding agent and a second binding agent, wherein:

(i) the first binding agent is capable of specifically binding to a single individual unit of the target and essentially saturating all binding sites in the sample, and (ii) the second binding agent is capable of specifically binding to the first binding agent and a predetermined portion of said second binding agent comprises an enzyme, and thereby forming discrete single target sites, each target site comprising a single individual unit of the target, the first binding agent and the second binding agent, wherein a portion of said discrete single target sites comprises the second binding agent comprising the enzyme;

(b) visualizing the discrete single target sites comprising the enzyme by:

(1) incubating the sample comprising one or more of said discrete single target sites in an aqueous solution (A) comprising:

a peroxide compound in an amount that is less than 2 mM, a first substrate of the enzyme associated with the discrete single target sites, and a second substrate of said enzyme, wherein said first substrate is 3,3'-diaminobenzidine or a derivative thereof, and wherein said second substrate is a conjugate molecule comprising (i) at least two compounds that are capable of serving as substrates of said enzyme, wherein at least one of the at least two compounds is a compound of the formula (II):

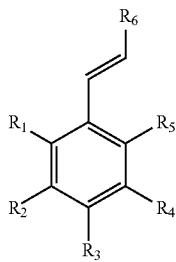
(II)

wherein:
R₁ is —H, —O—X, N(X)₂, or —S—X,
R₂ is —H, —O—X, —N(X)₂, or —S—X,
R₃ is —H, —OH, —NH₂, or —SH;
R₄ is —H, —O—X, —N(X)₂, or —S—X,
R₅ is —H, —O—X, N(X)₂, or —S—X,
R₆ is —CON(X)₂ or CO—X,
wherein:
H is hydrogen,
O is oxygen,
S is sulphur,
N is nitrogen, and
X is H, alkyl, or aryl,
and (ii) a detectable label, wherein the detectable label is selected from the group consisting of a fluorescent matter, a luminescent matter, a radioactive matter, a chromogenic matter, and a member of a specific binding pair, thereby forming discrete deposits of the second substrate at the discrete single target sites; and
(2) visualizing said discrete single target sites;
(c) quantifying the visualized discrete single target sites; and
(d) determining the amount of the target in the sample based on the quantity of the visualized discrete single target sites;
wherein the second binding agent comprises a mixture of at least one binding molecule labeled with the enzyme and at least one unlabeled binding molecule that are of the same species and have essentially the same affinity to the first binding agent, wherein a ratio between the labeled and unlabeled binding molecules is predetermined, and
wherein the discrete single target sites are visualized as visually distinct dots.

2. The method according to claim 1, wherein the first and second binding agents are members of specific binding pairs.

3. The method according to claim 1, wherein the enzyme is an enzyme with oxidoreductase activity.

4. The method according to claim 3, wherein the enzyme has peroxidase or phenoloxidase activity.

5. The method according to claim 4, wherein the enzyme is horseradish peroxidase, soybean peroxidase or laccase, or a functional analogue of said enzymes.

6. The method according to claim 1, wherein the amount of 3,3'-diaminobenzidine or the derivative thereof is from around 0.1 mM to less than 1 mM.

7. The method according to claim 1, wherein the at least two compounds are defined by formula (II).

8. The method according to claim 7, wherein the at least two compounds defined by formula (II) are identical compounds.

9. The method according to claim 7, wherein the at least two compounds defined by formula (II) are different compounds.

10. The method according to claim 1, wherein the at least two compounds are selected from the group consisting of cinnamic acid, ferulic acid, caffeic acid, amino cinnamic acid, sinapic acid, and derivatives thereof.

11. The method according to claim 1, wherein the conjugate comprises at least one tyrosine residue as a substrate of the enzyme.

12. The method according to claim 1, comprising the at least two compounds that are capable of serving as the substrates of the enzyme associated with the discrete single target sites that are separated from each other in the conjugate molecule by at most 30 consecutively connected atoms wherein the detectable label is separated from any of said substrates by at least 30 consecutively connected atoms.

13. The method according to claim 12, wherein the at least 30 consecutively connected atoms separating the detectable label from any of said substrates comprise 2 to 10 repeats of the following formula (III):

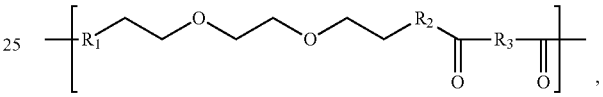

wherein R₁ and R₂ are selected from N and O, and R₃ is selected from methyl, ethyl, propyl, CH₂OCH₂, and (CH₂OCH₂)₂, and wherein the 30 consecutively connected atoms comprise no more than three consecutively repeating ethyloxy groups.

14. The method according to claim 1, wherein the method comprises a step (1') that precedes step (1), wherein the sample is incubated in an aqueous solution (B) which has the same composition as an aqueous solution (A) with the exception that it does not comprise a second substrate.

15. The method according claim 1, wherein each of the visually distinct dots has an apparent diameter that is around or greater than 0.4 micrometers.

16. The method according claim 1, wherein the method comprises at least one washing step between steps (a), (b), and/or (c).

17. The method according to claim 1, wherein the target is a biological or chemical target molecule, particle, molecular or cellular complex, molecular or cellular structure, virus, or microorganism, or a fragment of said target molecule, particle, complex, structure, virus, or microorganism.

18. The method according to claim 1, wherein the individual unit of a target is an individual single biological or chemical molecule, individual single particle, individual single molecular or cellular complex, individual single molecular or cellular structure, or individual single virus, or individual single microorganism, or an individual single fragment of said molecule, particle, complex, structure, virus, or microorganism.

19. The method according to claim 17, wherein the target is a protein or a fragment or a derivative thereof, and the first binding agent and the second binding agent are antibodies.

20. The method according to claim 19, wherein the protein is a plasma intracellular or nuclear membrane protein, a nuclear, organelle, or cytoplasmic protein.

21. The method according to claim 17, wherein the target is a biological marker.

22. The method according to claim 17, wherein the target is HER2 or a product thereof.

23. The method according to claim 1, wherein the sample is a biological, chemical, or environmental sample.

24. The method according to claim 1, wherein quantification of the visually distinct dots is performed manually, semi-manually, or automatically.

25. The method according to claim 1, wherein the method is for quantifying the absolute amount of the target in the sample.

26. The method according to claim 1, wherein the method is for quantifying a relative amount of the target in the sample.

27. The method of claim 25, wherein the sample is a histological sample.

28. The method of according to claim 27, wherein the amount of the target is determined per an area, per a volume of the sample, per an object, or per a reference marker comprised in the sample.

29. The method according to claim 28, wherein the object is a cellular structure or cellular organelle.

30. The method according to claim 29, wherein the object is the nucleus.

31. The method according to claim 28, wherein the reference marker is a protein, and the first binding agent and the second binding agent are antibodies.

\* \* \* \* \*